(12) United States Patent
Zachar et al.

(10) Patent No.: US 8,999,074 B2
(45) Date of Patent: Apr. 7, 2015

(54) FLUID INPUT MODULE FOR MULTI-LUMEN CATHETERS

(75) Inventors: Oron Zachar, Tel Aviv (IL); Elad Einav, Tel Aviv (IL); Gil Yigal, Gan Yavne (IL)

(73) Assignee: Airway Medix S.A., Warszawa (PL)

( * ) Notice: Subject to any disclaimer, the term of this patent is extended or adjusted under 35 U.S.C. 154(b) by 0 days.

(21) Appl. No.: 13/806,958

(22) PCT Filed: Aug. 26, 2012

(86) PCT No.: PCT/IL2012/000320
§ 371 (c)(1),
(2), (4) Date: Feb. 4, 2013

(87) PCT Pub. No.: WO2013/030821
PCT Pub. Date: Mar. 7, 2013

(65) Prior Publication Data
US 2014/0142496 A1 May 22, 2014

Related U.S. Application Data

(63) Continuation-in-part of application No. PCT/IB2012/051532, filed on Mar. 29, 2012.

(60) Provisional application No. 61/527,658, filed on Aug. 26, 2011, provisional application No. 61/539,998, (Continued)

(30) Foreign Application Priority Data

Sep. 28, 2011 (GB) .................................. 1116735.0
Nov. 16, 2011 (GB) .................................. 1119794.4

(51) Int. Cl.
*A61M 1/00* (2006.01)
*A61M 16/04* (2006.01)

(52) U.S. Cl.
CPC ......... *A61M 16/0463* (2013.01); *A61M 1/0023* (2013.01); *A61M 2209/10* (2013.01)

(58) Field of Classification Search
USPC ........ 134/166 C, 166 R; 128/207.15; 604/35, 604/99.01–99.04, 118, 119, 920
See application file for complete search history.

(56) References Cited

U.S. PATENT DOCUMENTS 3,211,150 A * 10/1965 John .......................... 604/97.02
4,351,328 A 9/1982 Bodai
(Continued)

FOREIGN PATENT DOCUMENTS

EP 0 692 273 4/2004
GB 2 482 618 A 2/2012
(Continued)

OTHER PUBLICATIONS

An International Search Report and a Written Opinion both dated Nov. 15, 2012, which issued during the prosecution of Applicant's PCT/IL2012/000320. (Continued)

*Primary Examiner* — Nathan R Price
(74) *Attorney, Agent, or Firm* — Sughrue Mion, PLLC

(57) ABSTRACT

A cleaning catheter (200) includes fluid-delivery and suction lumens (520, 530). A flow regulator (700) defines suction and fluid ports (830, 827). A mechanical user control element (320) is configured to mechanically and non-electrically set activation states of the flow regulator (700), and transition between first and third configurations via a second configuration. When the control element (320) is in the first configuration, the flow regulator (700) blocks fluid communication (a) between the suction port (830) and the suction lumen (530) and (b) between the fluid port (827) and the fluid-delivery lumen (520). When the control element (320) is in the second configuration, the flow regulator effects fluid communication between the suction port (830) and the suction lumen (530), and blocks fluid communication between the fluid port (827) and the fluid-delivery lumen (520). When the control element (320) is in the third configuration, the flow regulator (700) effects fluid communication (a) between the suction port (830) and the suction lumen (530) and (b) between the fluid port (827) and the fluid-delivery lumen (520).

1 Claim, 23 Drawing Sheets

Related U.S. Application Data filed on Sep. 28, 2011, provisional application No. 61/560,385, filed on Nov. 16, 2011, provisional application No. 61/603,340, filed on Feb. 26, 2012, provisional application No. 61/603,344, filed on Feb. 26, 2012, provisional application No. 61/609,763, filed on Mar. 12, 2012, provisional application No. 61/613,408, filed on Mar. 20, 2012, provisional application No. 61/635,360, filed on Apr. 19, 2012, provisional application No. 61/655,801, filed on Jun. 5, 2012, provisional application No. 61/660,832, filed on Jun. 18, 2012, provisional application No. 61/673,744, filed on Jul. 20, 2012, provisional application No. 61/496,019, filed on Jun. 12, 2011, provisional application No. 61/483,699, filed on May 8, 2011, provisional application No. 61/473,790, filed on Apr. 10, 2011, provisional application No. 61/468,990, filed on Mar. 29, 2011.

(56) References Cited

U.S. PATENT DOCUMENTS

| | | |
|---|---|---|
| 4,569,344 A | 2/1986 | Palmer |
| 4,762,125 A | 8/1988 | Leiman et al. |
| 5,003,657 A | 4/1991 | Boiteau |
| 5,029,580 A | 7/1991 | Radford et al. |
| 5,067,497 A | 11/1991 | Greear |
| 5,125,893 A | 6/1992 | Dryden |
| 5,269,756 A | 12/1993 | Dryden |
| 5,279,549 A | 1/1994 | Ranford |
| 5,709,691 A | 1/1998 | Morejon |
| 5,738,091 A | 4/1998 | Kee |
| 6,082,361 A | 7/2000 | Morejon |
| 6,227,200 B1 | 5/2001 | Crump |
| 6,318,368 B1 | 11/2001 | Morejon |
| 6,602,219 B2 | 8/2003 | Madsen |
| 6,612,304 B1 | 9/2003 | Cise |
| 6,805,125 B1 | 10/2004 | Crump |
| 6,923,184 B1 | 8/2005 | Russo |
| 6,935,339 B2 | 8/2005 | Neto |
| 7,051,737 B2 | 5/2006 | Kolobow |
| 7,273,473 B2 | 9/2007 | Owens et al. |
| 7,625,207 B2 | 12/2009 | Hershey |
| 7,669,600 B2 | 3/2010 | Morejon |
| 2005/0172971 A1 | 8/2005 | Kolobow |
| 2006/0099434 A1 | 5/2006 | Hoetger |
| 2007/0028924 A1 | 2/2007 | Madsen et al. |
| 2007/0038226 A1 | 2/2007 | Galdonik |
| 2007/0089748 A1 | 4/2007 | Madsen et al. |
| 2009/0178681 A1 | 7/2009 | Bracken |
| 2009/0260632 A1 | 10/2009 | Abnousi et al. |
| 2010/0137899 A1 | 6/2010 | Razack |
| 2010/0186748 A1 | 7/2010 | Morejon |
| 2010/0199999 A1 | 8/2010 | Vazales |
| 2011/0023885 A1 | 2/2011 | Vazales et al. |
| 2011/0180072 A1 | 7/2011 | Morejon |
| 2013/0035628 A1* | 2/2013 | Garrison et al. ............ 604/8 |

FOREIGN PATENT DOCUMENTS

| | | |
|---|---|---|
| GB | 2 482 618 B | 7/2012 |
| WO | 89/07466 | 8/1989 |
| WO | 94/03226 | 2/1994 |
| WO | 99/38548 | 8/1999 |
| WO | 2006/099434 | 9/2006 |
| WO | 2007/024288 | 3/2007 |
| WO | 2007/146613 | 12/2007 |
| WO | 2010/091309 | 8/2010 |
| WO | 2011/020985 | 2/2011 |
| WO | 2011/094517 | 8/2011 |
| WO | 2012/131626 | 10/2012 |

OTHER PUBLICATIONS

An International Search Report dated Oct. 16, 2012, which issued during the prosecution of Applicant's PCT/IB2012/051532.
Examination Report dated Nov. 3, 2011 which issued during the prosecution of GB Patent Application No. 1116735.0.
Search Report dated Nov. 2, 2011 which issued during the prosecution of GB Patent Application No. 2482618.
Novelty Search Report dated Sep. 16, 2011 which issued during the prosectuion of Swedish Patent Application No. 179871.

* cited by examiner

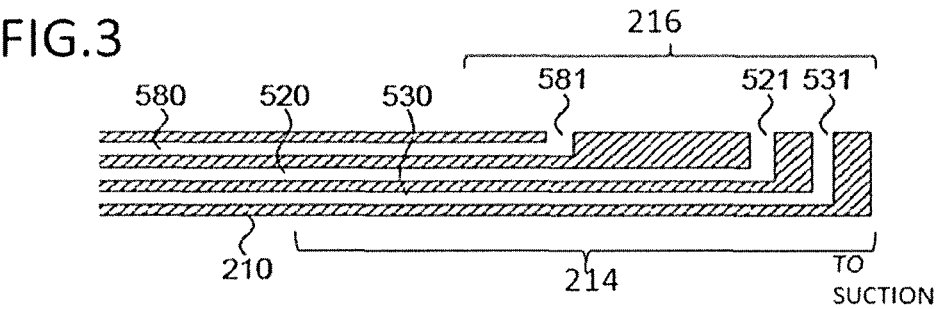
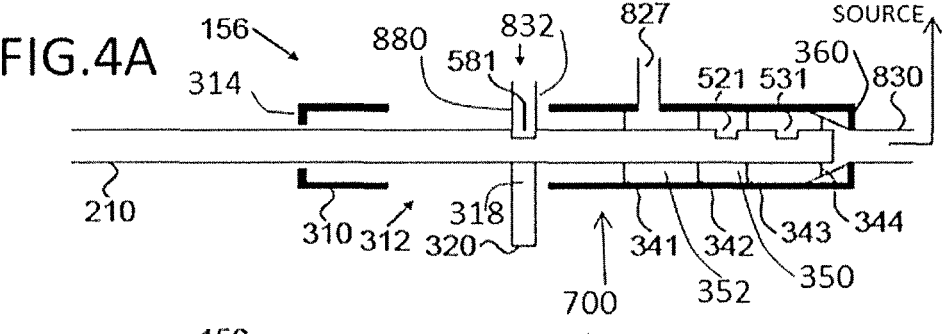
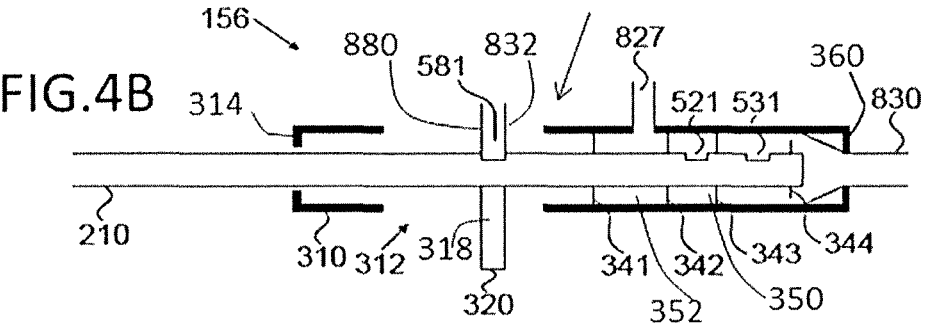
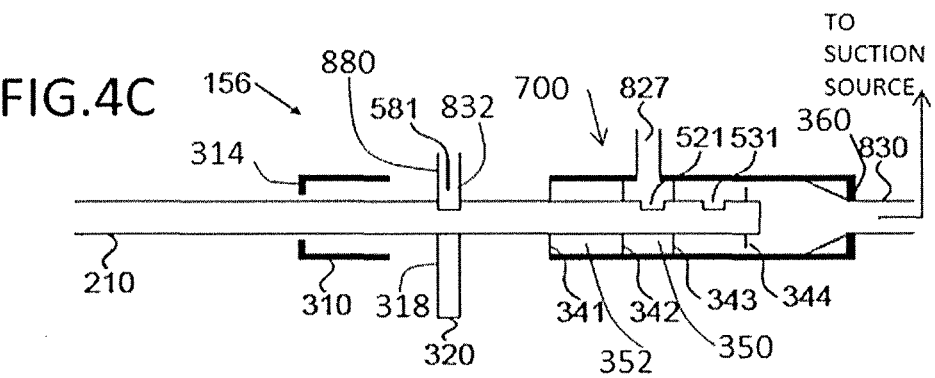

DISTAL ←—→ PROXIMAL

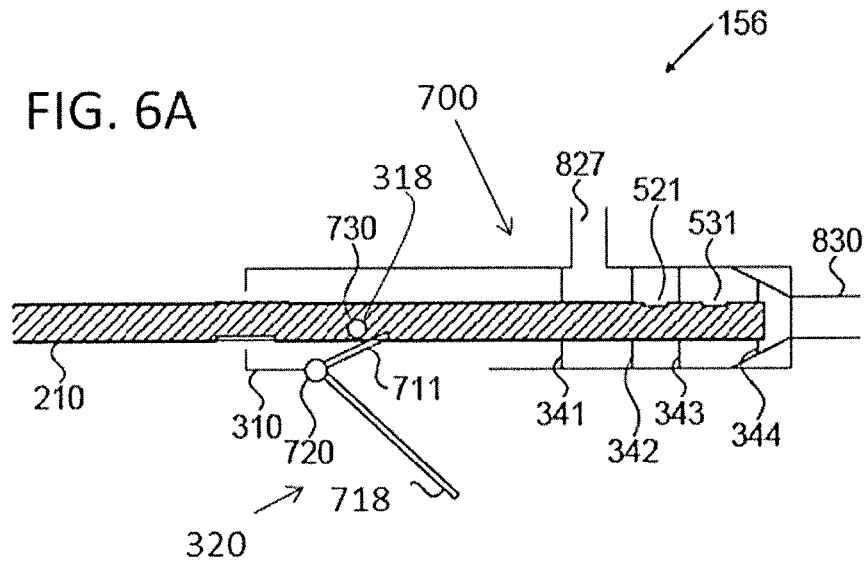
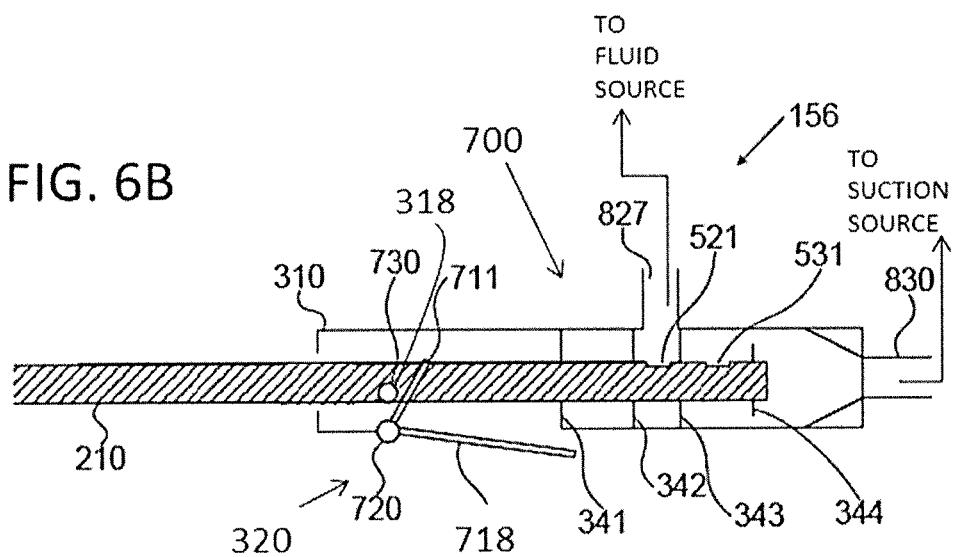

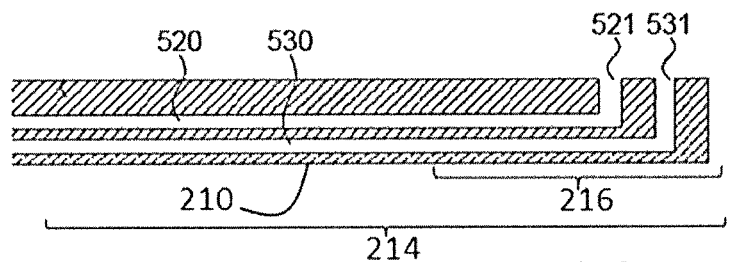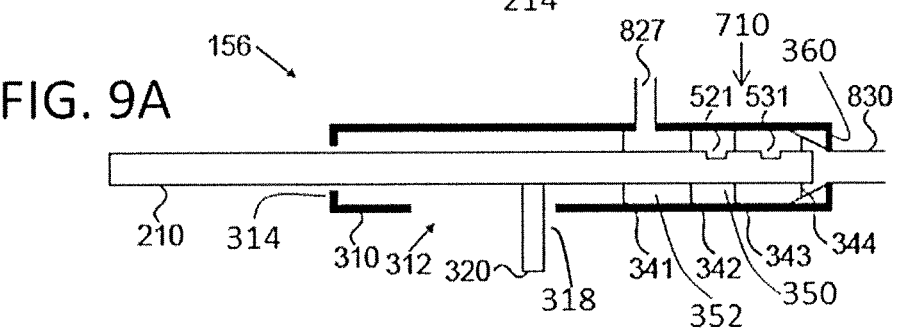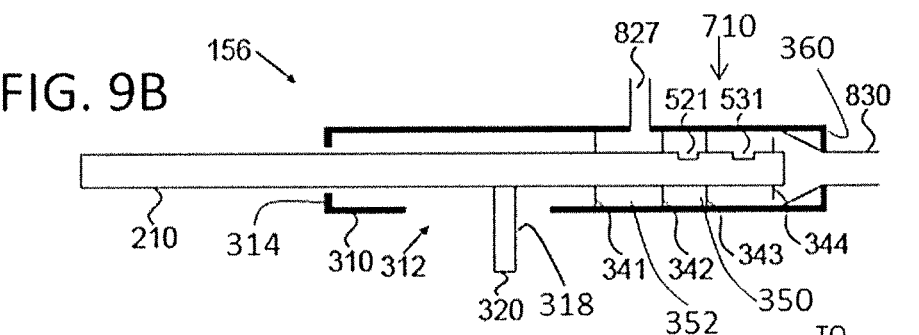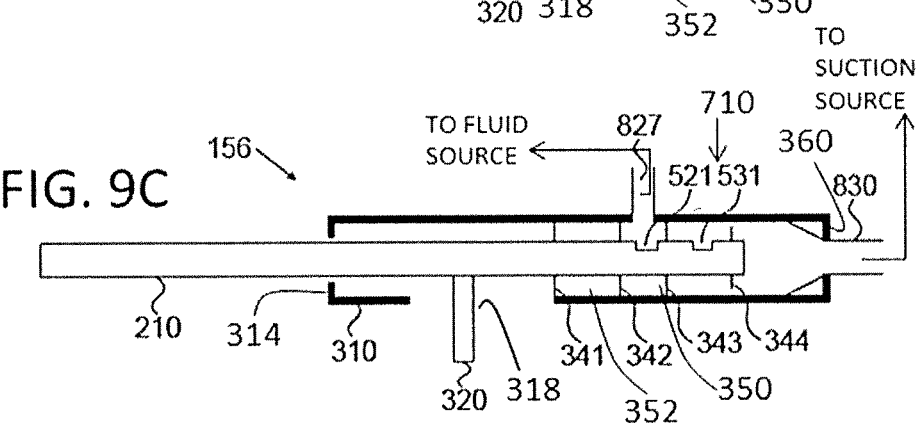

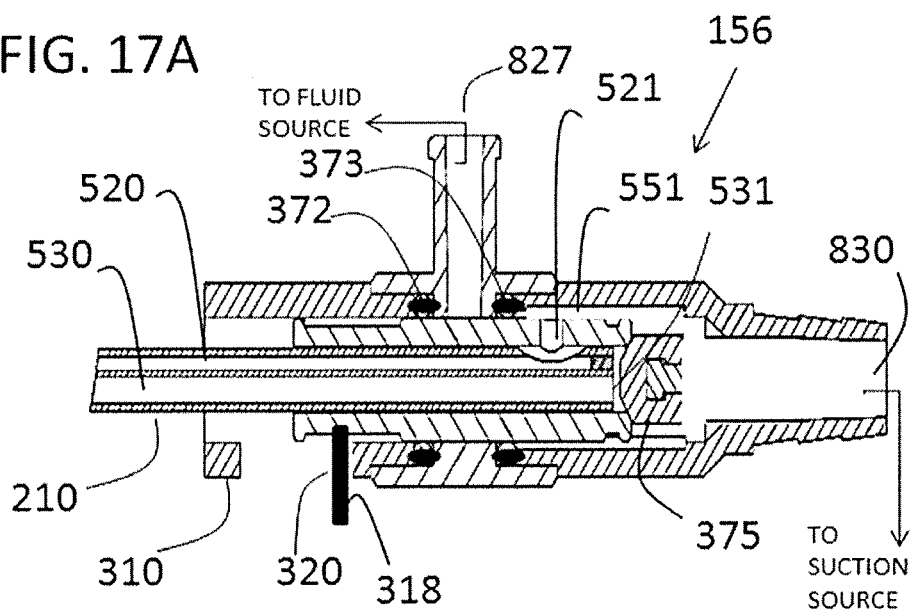
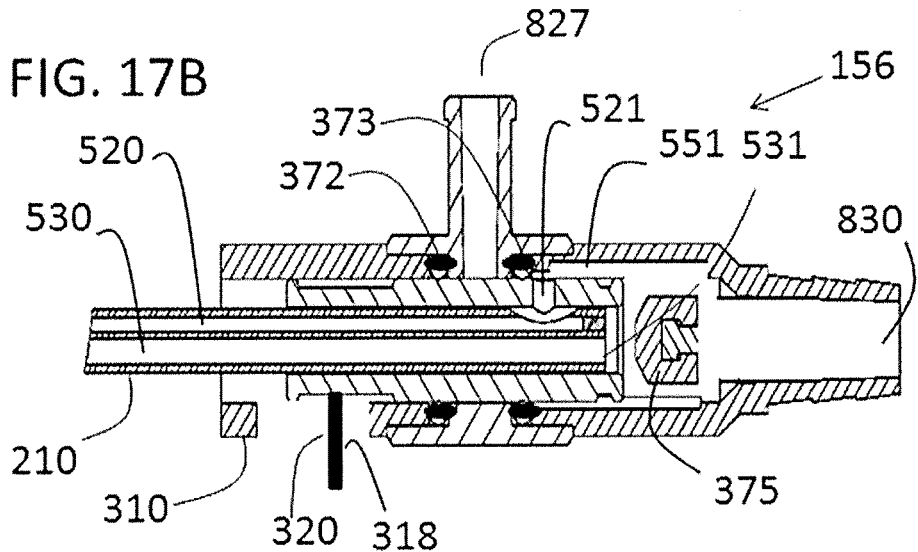

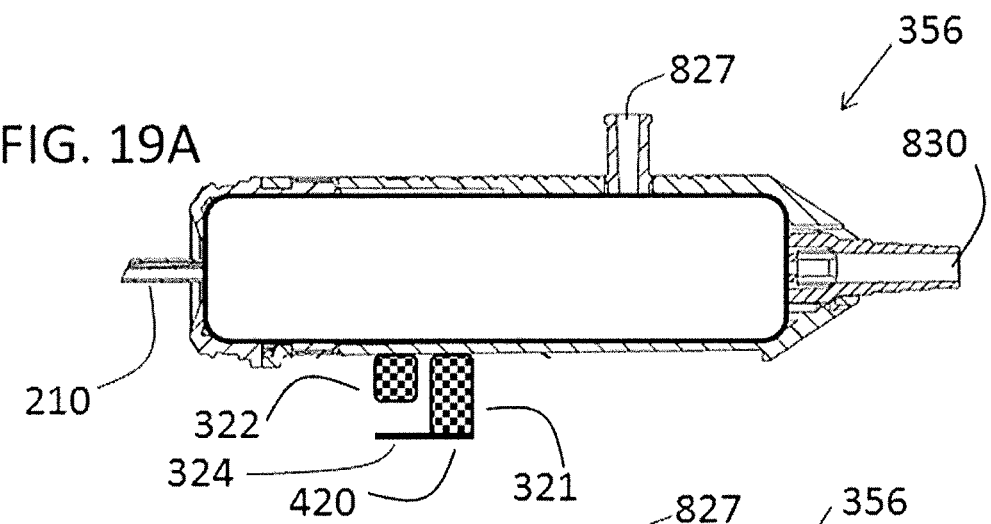
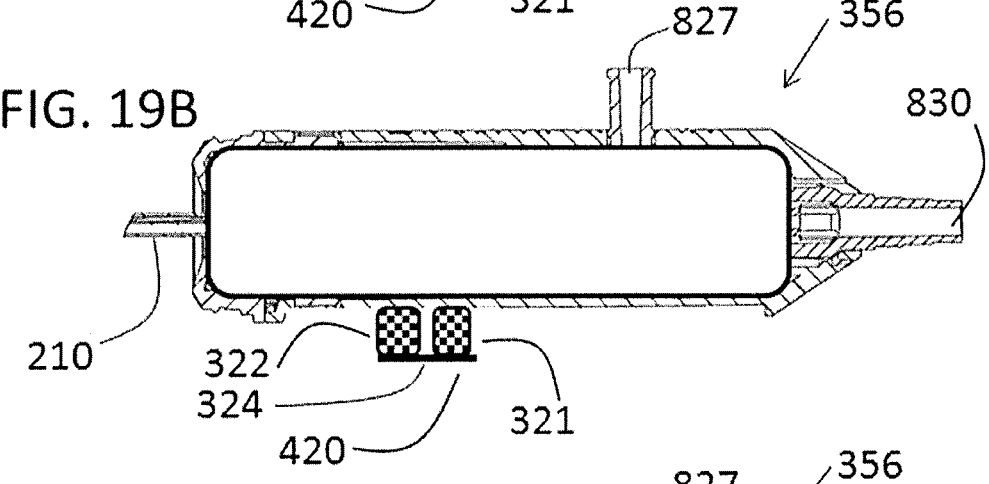
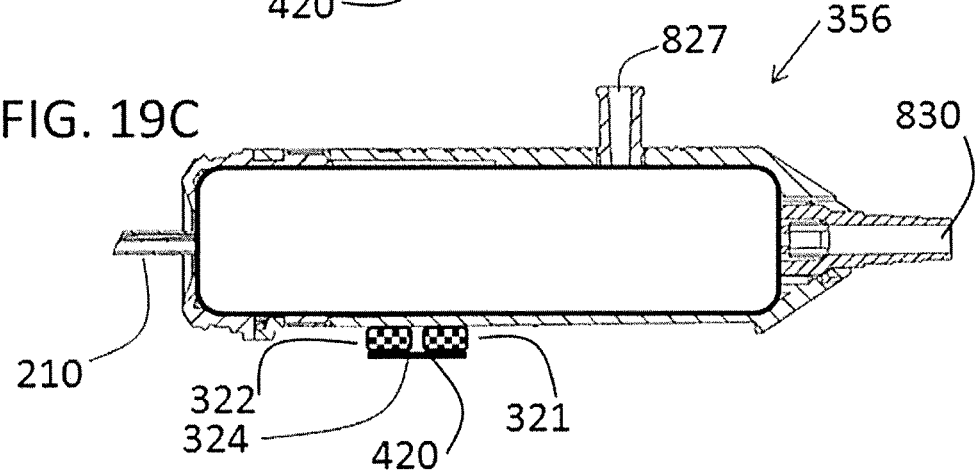

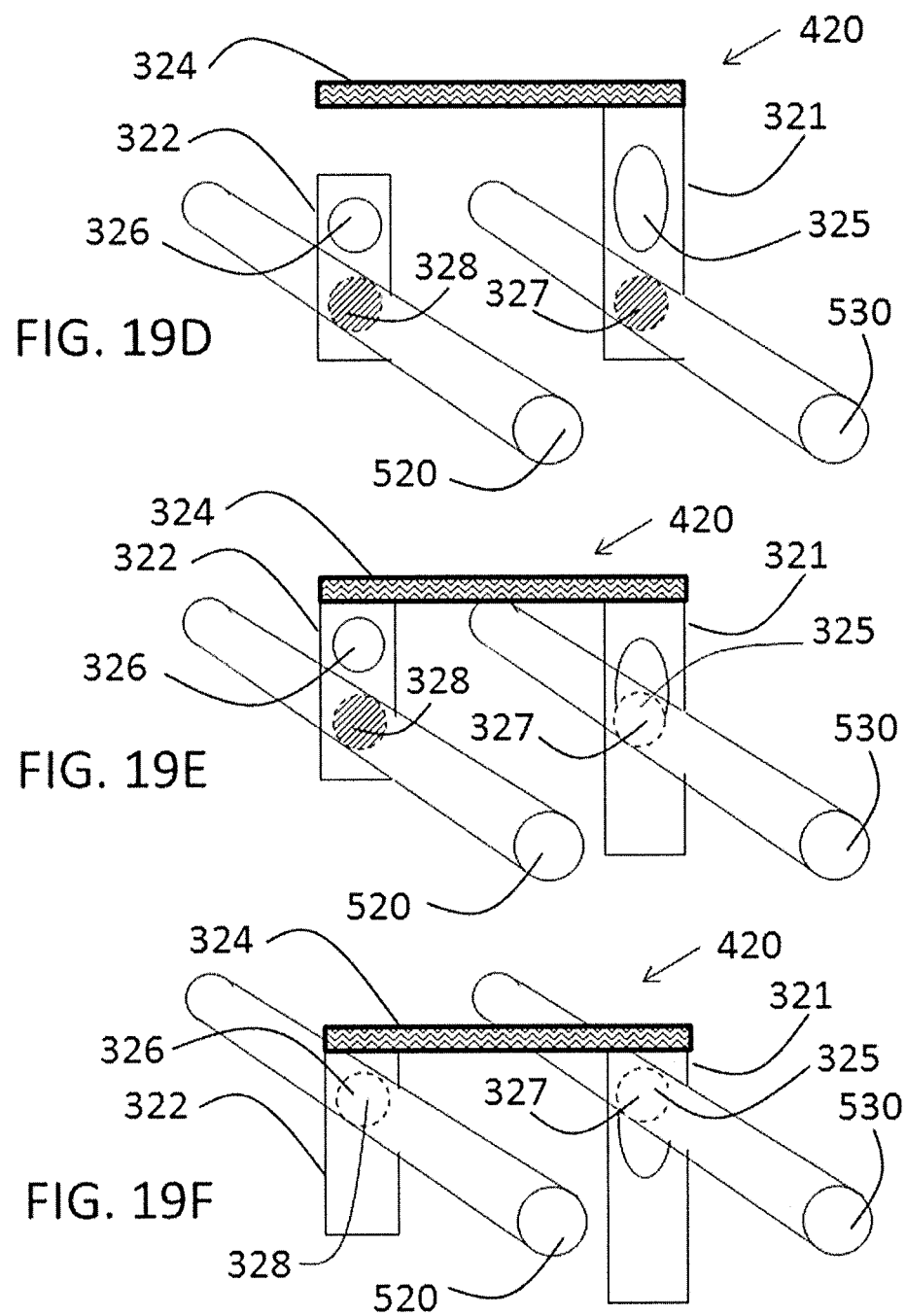

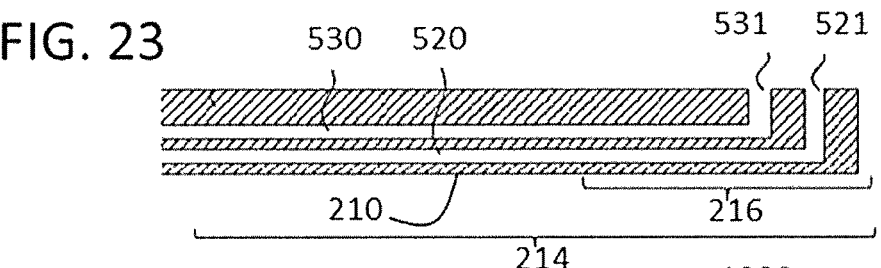
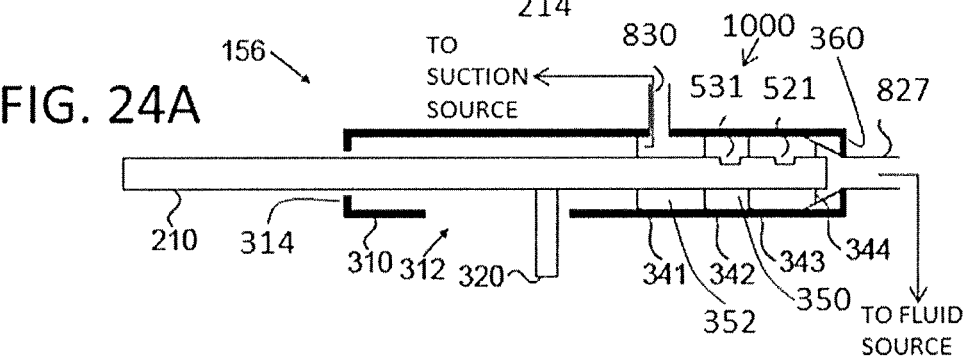
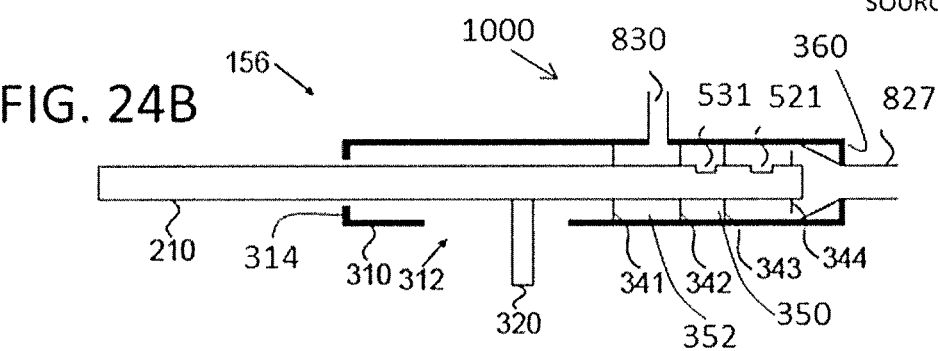
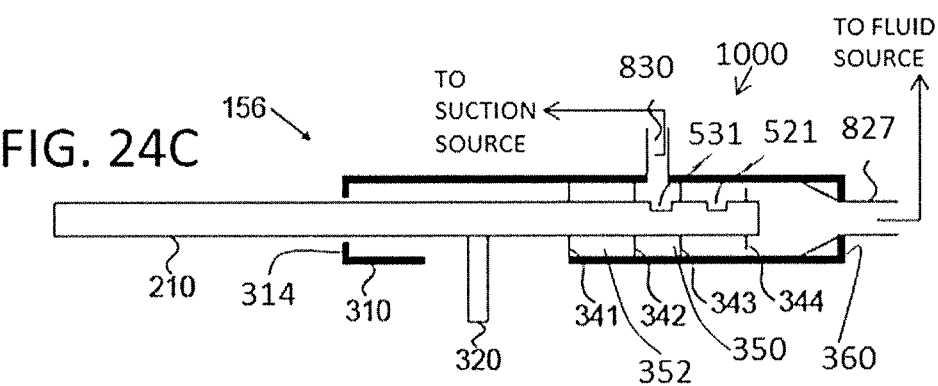

FLUID INPUT MODULE FOR MULTI-LUMEN CATHETERS

CROSS-REFERENCE TO RELATED APPLICATIONS

The present application claims priority from and is a continuation-in-part of:

International Application PCT/IB2012/051532, filed Mar. 29, 2012, which published as PCT Publication WO 2012/131626, and which claims priority from:
U.S. Provisional Application 61/539,998, filed Sep. 28, 2011;
UK Application GB 1116735.0, filed Sep. 28, 2011, which published as GB 2482618 A to Einav et al. and GB 2482618 B to Einav et al.;
UK Application GB 1119794.4, filed Nov. 16, 2011;
U.S. Provisional Application 61/468,990, filed Mar. 29, 2011;
U.S. Provisional Application 61/473,790, filed Apr. 10, 2011;
U.S. Provisional Application 61/483,699, filed May 8, 2011;
U.S. Provisional Application 61/496,019, filed Jun. 12, 2011;
U.S. Provisional Application 61/527,658, filed Aug. 26, 2011;
U.S. Provisional Application 61/560,385, filed Nov. 16, 2011;
U.S. Provisional Application 61/603,340, filed Feb. 26, 2012;
U.S. Provisional Application 61/603,344, filed Feb. 26, 2012;
U.S. Provisional Application 61/609,763, filed Mar. 12, 2012; and
U.S. Provisional Application 61/613,408, filed Mar. 20, 2012;
UK Application GB 1116735.0, filed Sep. 28, 2011; and
UK Application GB 1119794.4, filed Nov. 16, 2011; and
the present patent application claims priority from:
U.S. Provisional Application 61/527,658, filed Aug. 26, 2011;
U.S. Provisional Application 61/539,998, filed Sep. 28, 2011;
U.S. Provisional Application 61/560,385, filed Nov. 16, 2011;
U.S. Provisional Application 61/603,340, filed Feb. 26, 2012;
U.S. Provisional Application 61/603,344, filed Feb. 26, 2012;
U.S. Provisional Application 61/609,763, filed Mar. 12, 2012;
U.S. Provisional Application 61/613,408, filed Mar. 20, 2012;
U.S. Provisional Application 61/635,360, filed Apr. 19, 2012;
U.S. Provisional Application 61/655,801, filed Jun. 5, 2012;
U.S. Provisional Application 61/660,832, filed Jun. 18, 2012; and
U.S. Provisional Application 61/673,744, filed Jul. 20, 2012.

All of the above-listed regular and provisional applications are assigned to the assignee of the present application, and are incorporated herein by reference.

FIELD OF THE APPLICATION

The present invention relates generally to medical suction catheter devices, and specifically to catheter devices for aspiration of tracheobronchial secretions and/or cleaning of tracheal ventilation tubes.

BACKGROUND OF THE APPLICATION

Suction catheters are commonly used to aspirate tracheobronchial fluids in patients ventilated with endotracheal tube (ETT) and tracheostomy tube devices. A problematic aspect of the use of suction catheters is the presence of bacterial biofilm within the ETT lumen through which the suction catheter passes. Consequently, as the suction catheter is inserted, there is high risk of it carrying bacterial biofilm from the ETT lumen deeper into the bronchial tree where the suction catheter reaches, and thereby increasing the risk of lung infection. Moreover, buildup of substantial biofilm thickness reduces the effective free lumen of the ETT for air passage. Therefore, there is a need for maintaining cleaner ETT lumens between suction operations, and preventing buildup of significant biofilm thickness.

UK Publication GB 2482618 A to Einav et al., which is assigned to the assignee of the present application and is incorporated herein by reference, describes a multi-lumen catheter for multiple fluids conduction, including balloon inflation with air via an inflation lumen, suction via a suction lumen, and cleaning fluids delivery via a cleaning fluid-delivery lumen.

SUMMARY OF THE APPLICATION

Some applications of the present invention provide a multi-lumen catheter for cleaning an inner surface of a tracheal ventilation tube. Some techniques of the present invention enable single-handed simultaneous activation of suctioning and irrigation (fluid delivery) in closed suction systems for use with tracheal ventilation tubes. Closed suction systems allow catheters to be used repeatedly without being detached from the tube system including the ventilation air supply. Applications of the present invention generally provide simple user control of conduction of multiple fluids under positive and negative pressure (suction).

In some applications of the present invention, a closed suction cleaning system comprises an input module, which comprises a flow regulator for activating delivery of both suction and positive-pressure fluid. For some applications, the input module comprises a mechanical user control element having first, second, and third configurations corresponding to first, second, and third activation states of the flow regulator. For some applications, the first, second, and third configurations are first, second, and third spatial positions, respectively. Typically, the input module is configured to provide a predetermined serial order of the activation of suction and fluid delivery operations inherently built into and limited by the device mechanical structure. Typically, the input module is configured necessarily to begin fluid delivery after beginning suction delivery, and to cease fluid delivery before ceasing suction delivery.

Some applications of the present invention provide increased safety of operation, by automatically initiating delivery of suction before initiating delivery of cleaning fluid, and terminating the delivery of suction after terminating the delivery of cleaning fluid. In some configurations of the cleaning system, this desired order of operating states is inherently built into the mechanical user control element.

Activation of the mechanical user control element by a user automatically activates the different states of fluid and suction delivery in a predetermined desired order. This prevents possible error by the user, and simplifies activation by the user. As a result, in these configurations of the cleaning system, operational safely is inherent because there is no activation state in which cleaning fluid flow is enabled without suction also being activated. In contrast, in conventional cleaning system, activation of suction and activation of fluid delivery are typically performed independently by the user and are not correlated by the system in a particular manner.

Typically, the mechanical user control element comprises a single user-interface element (e.g., a handle or a button) for activating both suction and fluid delivery.

For some applications, the flow regulator controls both fluid delivery and inflation of an inflatable element of the multi-lumen catheter.

For some applications, the input module is configured such that a predetermined serial order of the activation of suction and balloon inflation operations is inherently built into and limited by the mechanical structure of the device.

For some applications, the cleaning system further comprises an expandable, e.g., inflatable, element near the distal end of the catheter. For some applications, inflation of the inflatable element is effected by fluid pressure communication with a fluid port of the input module, which fluid port is in fluid communication with a pressurized fluid source.

For some applications, deflation of the inflatable element is effected via suction fluid communication with a suction port of the input module, which suction port is in fluid communication with a suction source.

For some applications, the cleaning system is configured to enable selective activation of suction through orifices located both proximal and distal to the expandable element, or primarily (e.g., exclusively) proximal to the expandable element. For some applications, the cleaning system is configured to enable selective combined activation of suction through orifices located proximal to the expandable element with or without suction through orifices located distal to the inflatable element.

For some applications, the closed suction cleaning system comprises an elongated catheter main body and an input module having multiple connectors for connection with various fluid sources. The fluids sources typically include at least a suction source and a pressurized fluid source, and, optionally, an inflation source. The catheter main body typically comprises at least one suction lumen and one fluid-delivery lumen.

For some applications, the input module comprises a mechanical user control element, which is configured to control activation of the delivery of a plurality of fluids to the catheter in a predefined order of activation. The mechanical user control element typically mechanically and non-electrically sets the activation states of the flow regulator.

For some applications, the mechanical user control element is configured to assume at least first, second, and third configurations, and, typically, to transition between the first and the third spatial positions via the second configuration. For some applications, the first, second, and third configurations are first, second, and third spatial positions, respectively. The configurations (e.g., spatial positions) activate the flow regulator to assume respective corresponding distinct modes of fluids flow in the lumens of the catheter main body.

For some applications, the cleaning system may be used for two different purposes:
for cleaning the lumen of a tracheal ventilation tube—the user typically rapidly transitions the user control element from the first to the third configurations (e.g., spatial positions) via the second configuration (e.g., spatial position), for example, in less than one second, typically is less than 0.5 seconds. For cleaning the ventilation tube, there is generally no benefit to putting the flow regulator in the second activation state (suction without cleaning fluid flow), rather than transitioning directly from the first activation state (suction and cleaning fluid flow both blocked) directly to the third activation state (suction and cleaning fluid flow both enabled); and
for suctioning the trachea outside of and distal to the ventilation tube—the user transitions the user control element from the first to the second configurations (e.g., spatial positions), and leaves the flow regulator in the second activation state (suction without cleaning fluid flow) throughout most the trachea suctioning procedure.

The user may use the cleaning system for both of these purposes at different times during patient care. For example, the system may be used to clean the ventilation tube once every six hours, and for suctioning the lungs once every three hours. The user may choose to perform these two functions serially during a single session; the user first suctions the trachea by putting the user control element in the second configuration, and then immediately upon conclusion of this suctioning, transitions the user control element to the third configuration to activate cleaning of the lumen of the ventilation tube.

The cleaning system may implement one or more of the features described above, or any combination thereof.

In some applications of the present invention, the cleaning catheter comprises an elongate flexible main body, an inflatable, one or more suction orifices, and one or more fluid delivery orifices. The cleaning catheter is typically integrated into a closed suction system. The cleaning system described herein may implemented in combination with techniques described in UK Publication GB 2482618 A to Einav et al., which is assigned to the assignee of the present application and is incorporated herein by reference.

There is therefore provided, in accordance with an application of the present invention, apparatus for use with a tracheal ventilation tube, a pressurized fluid source, and a suction source, the apparatus including:
  a cleaning catheter, which is insertable into the ventilation tube, and which includes: (a) an elongate, flexible, tubular main body; (b) one or more fluid-delivery lumens arranged along the main body; and (c) one or more suction lumens arranged along the main body; and
  an input module, which is coupled to the cleaning catheter, and includes:
    a flow regulator, which (a) is shaped so as to define a suction port coupleable in fluid communication with the suction source, and a fluid port coupleable in fluid communication with the pressurized fluid source, and (b) which is configured to assume at least first, second, and third activation states; and
    a mechanical user control element, which is configured (a) to mechanically and non-electrically set the activation states of the flow regulator, (b) to assume at least first, second, and third configurations, and (c) to transition between the first and the third configurations via the second configuration,
  wherein the input module is configured such that:
  when the user control element is in the first configuration, the flow regulator is in the first activation state, in which the flow regulator blocks fluid communication (a) between the suction port and the one or more suction lumens and (b) between the fluid port and the one or more fluid-delivery lumens, when the user control element is in the second configuration, the flow regulator is in the second activation state, in which the flow regulator effects the fluid communication between the suction port and the one or more suction lumens, and blocks the fluid communication between the fluid port and the one or more fluid-delivery lumens, and when the user control element is in the third configuration, the flow regulator is in the third activation state, in which the flow regulator effects the fluid communication (a) between the suction port and the one or more suction lumens and (b) between the fluid port and the one or more fluid-delivery lumens.

For some applications, the first, the second, and the third configurations are first, second, and third spatial positions, respectively, and the mechanical user control element is configured to assume at least the first, the second, and the third spatial positions.

For some applications, the suction port is coupled in fluid communication with the suction source, and the fluid port is coupled in fluid communication with the pressurized fluid source.

For some applications, the suction port includes a male conical interface.

For some applications, the fluid port includes a Luer-Lok interface.

For some applications, the one or more fluid-delivery lumens are arranged along the main body at least partially within the main body.

For some applications, the one or more fluid-delivery lumens are arranged along the main body at least partially outside the main body.

For some applications, the one or more suction lumens are arranged along the main body at least partially within the main body.

For some applications, the one or more suction lumens are arranged along the main body at least partially outside the main body.

For some applications, the apparatus is for use with a ventilator, and the apparatus further includes a tube-connector assembly, which is configured to couple the ventilation tube in fluid communication with the ventilator, in a substantially air-tight manner.

For some applications, the apparatus further includes a pliable sleeve around at least a portion of the main body to inhibit contamination.

For any of the applications described above, the main body may be shaped so as to define one or more fluid-delivery orifices in fluid communication with an outer surface of the cleaning catheter, and one or more distal suction orifices, the one or more fluid-delivery lumens may be arranged to transport fluid received at respective one or more proximal portions of the one or more lumens from the pressurized fluid source, to the fluid-delivery orifices, and the one or more suction lumens may be arranged to convey suction from the suction source to the one or more distal suction orifices.

For some applications, a wall of the main body is shaped so as to define the one or more fluid-delivery orifices.

For some applications, the one or more fluid-delivery orifices have a total cross-sectional area in aggregate of between 0.04 and 1 mm2.

For some applications, the cleaning catheter further includes an expandable element, which is mounted to the main body at a location within 3 cm of at least one of the one or more distal suction orifices, and is expandable into contact with an inner surface of the ventilation tube.

For some applications, the location at which the expandable element is mounted to the main body is within 5 cm of a distal end of the main body.

For some applications, a wall of the inflatable element is shaped so as to define the one or more fluid-delivery orifices.

For some applications, the expandable element includes an inflatable element.

For some applications, the input module is configured such that the flow regulator, when in the first operating state, effects fluid communication between the inflatable element and the suction port, such that the inflatable element is deflated by the suction delivered via the suction port.

For some applications, the inflatable element includes a balloon.

For some applications, the inflatable element has a greatest diameter of between 6 and 12 mm when fully inflated and unconstrained.

For some applications, the cleaning catheter is configured such that an interior of the inflatable element is in fluid communication with at least one of the one or more fluid-delivery lumens, such that when the flow regulator is in the third activation state, the flow regulator effects fluid communication between the fluid port and the interior of the inflatable element, thereby inflating the inflatable element.

For some applications, the input module is configured such that the flow regulator, when in the second activation state, in addition to effecting the fluid communication between the suction port and the one or more suction lumens and blocking the fluid communication between the fluid port and the one or more fluid-delivery lumens, effects suction fluid communication between suction port and the one or more fluid-delivery lumens, thereby deflating the inflatable element.

For some applications, the input module is configured such that the flow regulator, when in the first activation state, in addition to blocking the fluid communication (a) between the suction port and the one or more suction lumens and (b) between the fluid port and the one or more fluid-delivery lumens, effects fluid communication between the suction port and the one or more fluid-delivery lumens, thereby deflating the inflatable element.

For some applications:

the flow regulator further includes a valve, which is in fluid communication with the suction port, and the input module is configured such that the flow regulator, when in the first activation state, in addition to blocking the fluid communication (a) between the suction port and the one or more suction lumens and (b) between the fluid port and the one or more fluid-delivery lumens: (a) when the valve is in an open position, effects fluid communication between the suction port and the one or more fluid-delivery lumens, thereby deflating the inflatable element, and (b) when the valve is in a closed position, blocks fluid communication between the suction port and the one or more fluid-delivery lumens.

For some applications, at least one of the fluid-delivery orifices is located within 10 cm of the expandable element.

For some applications:

the one or more suction lumens include (a) at least a first suction lumen and (b) at least a second suction lumen, the one or more distal suction orifices include (a) one or more first distal suction orifices, all of which first distal suction orifices are located proximal to the expandable element, and (b) one or more second suction orifices, all of which second distal suction orifices are located distal to the expandable element, the at least a first suction lumen is arranged to convey the suction from the suction source to the one or more first distal suction orifices, and the at least a second suction lumen is arranged to convey the suction from the suction source to the one or more second distal suction orifices.

For some applications, the input module is configured such that the flow regulator, when in at least one of the first, the second, and the third activation states, delivers the suction through the one or more second distal suction orifices at a strength that is weaker than 20% of the suction force applied through a largest one of the one or more first distal suction orifices, and, in at least another of the activation states, delivers the suction through the one or more second distal suction orifices at a strength that at a strength that is stronger than 20% of the suction force through the applied through the largest of the first distal suction orifices.

For some applications, the one or more fluid-delivery orifices are located within 3 cm of the expandable element.

For any of the applications described above, the mechanical user control element may include an axial-motion element, which is configured to assume at least first, second, and third axial positions along a single axis, when the mechanical user control element is in the first, the second, and the third configurations, respectively, and the second axial position is spatially between the first and the second axial positions along the axis.

For any of the applications described above, the main body may include a proximal-most input portion, which is inserted into and axially slidable with respect to the input module. For some applications, the input module is configured such that changes in configuration of the mechanical user control element cause corresponding changes in axial position of the input portion of the main body with respect to the input module. For some applications, the input module is configured such that the input portion assumes first, second, and third axial positions with respect to the input module, corresponding to the first, the second, and the third configurations of the mechanical user control element.

For any of the applications described above, the input module may further include a state protective selector, which is configured to provide a plurality of protective states, including:

a protective selector first state, in which the state protective selector locks mechanical user control element in the first configuration, a protective selector second state, in which the state protective selector allows the mechanical user control element to move only between the first configuration and the second configuration, and a protective selector third state, in which the state protective selector allows the mechanical user control element to reach the first, the second, and the third configurations.

There is further provided, in accordance with an application of the present invention, apparatus for use with a tracheal ventilation tube and a suction source, the apparatus including:

a cleaning catheter, which (a) is insertable into the ventilation tube, (b) is shaped so as to define one or more distal suction orifices, and (c) which includes:

an elongate, flexible, tubular main body; and an inflatable element, which is mounted to the main body at a location within 3 cm of at least one of the one or more distal suction orifices; and an input module, which is coupled to the cleaning catheter, and includes a flow regulator, which (a) is shaped so as to define a suction port coupleable in fluid communication with the suction source, and (b) is configured to assume at least first and second activation states, such that:

the flow regulator, when in the first activation state, effects fluid communication between the suction source and an interior of the inflatable element, thereby deflating the inflatable element, and the flow regulator, when in the second activation state, effects fluid communication between the suction source and the distal suction orifices, and does not effect the fluid communication between the suction source and the interior of the inflatable element.

The ordinal numbers of the states recited in claims do not necessarily correspond to the ordinal numbers of the states described in the specification. For example, the first activation state described in the previous paragraph may include certain features of the second activation state of the configuration of the cleaning system described hereinbelow with reference to FIG. 11B, and/or of the first activation state of the configuration of the cleaning system described hereinbelow with reference to FIG. 13A.

For some applications, the suction port is coupled in fluid communication with the suction source.

For some applications, the flow regulator, when in the first activation state, does not effect the fluid communication between the suction source and the distal orifices.

For some applications, the flow regulator, when in the first activation state, effects fluid communication between the suction source and the distal orifices.

For some applications, the cleaning catheter further includes one or more fluid-delivery lumens arranged along the main body, and the flow regulator, when in the first activation state, effects the fluid communication between the suction source and the interior of the inflatable element via at least one of the one or more fluid-delivery lumens, thereby deflating the inflatable element.

For some applications, the cleaning catheter further includes one or more suction lumens arranged along the main body, and the flow regulator, when in the second activation state, effects the fluid communication between the suction source and the distal suction orifices via the one or more suction lumens.

For some applications, the expandable element includes a balloon.

For some applications, the inflatable element is mounted to the main body is within 5 cm of a distal end of the main body.

For some applications, the inflatable element has a greatest diameter of between 6 and 12 mm when fully inflated and unconstrained.

For some applications, the apparatus is for use with a ventilator, and the apparatus further includes a tube-connector assembly, which is configured to couple the ventilation tube in fluid communication with the ventilator, in a substantially air-tight manner.

For some applications, the flow regulator, when in the first activation state, in addition to effecting fluid communication between the suction source and the interior of the inflatable element, effects fluid communication between the suction source and the distal suction orifices.

For some applications, the one or more fluid-delivery lumens are arranged along the main body at least partially within the main body. Alternatively or additionally, the one or more fluid-delivery lumens are arranged along the main body at least partially outside the main body. For some applications, the one or more suction lumens are arranged along the main body at least partially within the main body. Alternatively or additionally, the one or more suction lumens are arranged along the main body at least partially outside the main body.

For any of the applications described above, the apparatus may be for use with a pressurized fluid source, the cleaning catheter may further include one or more fluid-delivery lumens arranged along the main body, the main body may be shaped so as to further define one or more fluid-delivery orifices in fluid communication with the outer surface of the cleaning catheter, the flow regulator may be shaped so as to further define a fluid port coupleable in fluid communication with the pressurized fluid source, the flow regulator, when in the first activation state, in addition to effecting fluid communication between the suction source and the interior of the inflatable element, blocks fluid communication between the fluid port and the one or more fluid-delivery lumens, and the flow regulator, when in the second activation state, in addition to effecting the fluid communication between the suction source and the distal suction orifices, effects fluid communication between the fluid source and (a) the fluid-delivery orifices via at least one of the one or more fluid-delivery lumens, and (b) the interior of the inflatable element via at least one of the fluid-delivery lumens that are in fluid communication with the interior of the inflatable element, thereby inflating the inflatable element.

For some applications, the fluid port is coupled in fluid communication with the pressurized fluid source.

For some applications, at least one of the fluid-delivery orifices is located within 10 cm of the inflatable element.

For some applications, a wall of the main body is shaped so as to define the one or more fluid-delivery orifices.

For some applications, a wall of the inflatable element is shaped so as to define the one or more fluid-delivery orifices.

For some applications, the one or more fluid-delivery orifices have a total cross-sectional area in aggregate of between 0.04 and 1 mm2.

For some applications, the flow regulator, when in the second activation state, additionally effects fluid communication between the fluid source and the interior of the inflatable element via at least one of the one or more fluid-delivery lumens.

For any of the applications described above, the apparatus may further include a mechanical user control element, which is configured (a) to mechanically and non-electrically set the activation states of the flow regulator, (b) to assume at least first and second configurations, and the input module may be configured such that:

when the user control element is in the first configuration, the flow regulator is in the first activation state, and when the user control element is in the second configuration, the flow regulator is in the second activation state.

For some applications, the first and the second configurations are first and second spatial positions, respectively, and the mechanical user control element is configured to assume at least the first and the second spatial positions.

For some applications, the main body includes a proximal-most input portion, which is inserted into and axially slidable with respect to the input module.

For some applications, the input module is configured such that changes in configuration of the mechanical user control element cause corresponding changes in axial position of the input portion of the main body with respect to the input module.

For some applications, the input module is configured such that the input portion assumes first and second axial positions with respect to the input module, corresponding to the first and the second configurations of the mechanical user control element.

There is still further provided, in accordance with an application of the present invention, apparatus for use with a tracheal ventilation tube, the apparatus including a cleaning catheter having an outer surface, which (a) is insertable into the ventilation tube, (b) is shaped so as to define one or more fluid-delivery orifices in fluid communication with the outer surface of the cleaning catheter, and (c) includes:

an elongate, flexible, tubular main body; and an inflatable element, which is mounted to the main body, wherein the one or more fluid-delivery orifices are in fluid communication with an interior of the inflatable element.

For some applications, the expandable element is mounted to the main body at a location within 5 cm of a distal end of the main body.

For some applications, the cleaning catheter further includes one or more fluid-delivery lumens arranged along the main body, which are in fluid communication with the one or more fluid-delivery orifices and the interior of the inflatable element.

For some applications, a wall of the main body is shaped so as to define the one or more fluid-delivery orifices.

For some applications, a wall of the inflatable element is shaped so as to define the one or more fluid-delivery orifices.

For some applications, the one or more fluid-delivery lumens include exactly one fluid-delivery lumen, which is in fluid communication with the one or more fluid-delivery orifices and the interior of the inflatable element.

For some applications, the cleaning catheter includes exactly one fluid-delivery lumen at at least one axial location along the cleaning catheter proximal to a proximal-most one of the one or more fluid-delivery orifices.

For some applications, at least one of the fluid-delivery orifices is located within 10 cm of the inflatable element.

For some applications, all of the fluid-delivery orifices are located within 10 cm of the inflatable element.

For some applications, the expandable element includes a balloon.

For some applications, the inflatable element has a greatest diameter of between 6 and 12 mm when fully inflated and unconstrained.

For some applications, the apparatus is for use with a ventilator, and the apparatus further includes a tube-connector assembly, which is configured to couple the ventilation tube in fluid communication with the ventilator, in a substantially air-tight manner.

For some applications, the one or more fluid-delivery lumens are arranged along the main body at least partially within the main body.

For some applications, the one or more fluid-delivery lumens are arranged along the main body at least partially outside the main body.

For some applications, the apparatus further includes a pliable sleeve around at least a portion of the main body to inhibit contamination.

For some applications, the one or more fluid-delivery orifices have a total cross-sectional area in aggregate of between 0.04 and 1 mm2.

For any of the applications described above, the apparatus may be for use with a pressurized fluid source, and the one or more fluid-delivery orifices and the interior of the inflatable element may be arranged in intermittent fluid communication with the fluid source. For some applications, the cleaning catheter further includes one or more fluid-delivery lumens arranged along the main body, which are in fluid communication with the one or more fluid-delivery orifices and the interior of the inflatable element, and in intermittent fluid communication with the fluid source. For some applications, the apparatus further includes an input module, which is coupled to the cleaning catheter, and includes a flow regulator, which (a) is shaped so as to define a fluid port coupleable in fluid communication with the pressurized fluid source, and (b) is configured to assume at least one activation state, in which the flow regulator, effects fluid communication via the one or more fluid-delivery lumens between the pressurized fluid source and (i) the one or more fluid-delivery orifices and (ii) the interior of the inflatable element, thereby inflating the inflatable element. For some applications, the fluid port is coupled in fluid communication with the pressurized fluid source.

For any of the applications described above, the cleaning catheter may further include one or more suction lumens arranged along the main body, and the cleaning catheter may be shaped so as to further define one or more distal suction orifices that are in fluid communication with the one or more suction lumens.

There is additionally provided, in accordance with an application of the present invention, apparatus for use with a suction source, the apparatus including a cleaning catheter, which includes:

an elongate, flexible, tubular main body, which is shaped so as to define a distal-most suction orifice;

a suction lumen arranged along the main body at least partially within the main body in intermittent fluid communication with the suction source, a distal portion of the suction lumen is in fluid communication with the distal-most suction orifice, and an outer wall of the main body is shaped so as to define an opening extending through the outer wall of the main body into the suction lumen at an axial location proximal to the distal-most suction orifice; and an inflatable element, which is mounted to the main body at least partially along the opening; and a collapsible membrane, which is at least partially positioned along the opening within an interior of the inflatable element, so as to define an inflatable chamber between a wall of inflatable element and the collapsible membrane, wherein the collapsible membrane is positioned to at least partially occlude the suction lumen upon at least partial inflation of the inflatable chamber, thereby modulating a level of suction delivered to the distal-most suction orifice via the suction lumen.

For some applications, a distal tip of the main body is shaped so as to define the distal-most suction orifice.

For some applications, a lateral wall of the main body is shaped so as to define the distal-most suction orifice.

For some applications, the expandable element is mounted to the main body at a location within 5 cm of a distal end of the main body.

For some applications, the collapsible membrane is configured such that upon sufficient inflation of the inflatable chamber, the collapsible membrane penetrates into the at least one of the one or more suction lumens sufficiently to cross a central longitudinal axis of the at least one of the one or more suction lumens.

For some applications, the inflatable element has a greatest diameter of between 6 and 12 mm when fully inflated and unconstrained.

For some applications, the suction lumen includes exactly one suction lumen.

For some applications, the suction lumen includes a plurality of suction lumens.

For any of the applications described above, the main body may be shaped so as to further define one or more lateral suction orifices at one or more respective locations along the main body proximal to the inflatable element.

For any of the applications described above, the cleaning catheter may further include one or more fluid-delivery lumens arranged along the main body, and which are in fluid communication with the inflatable chamber.

For any of the applications described above, the apparatus may further include a pliable sleeve around at least a portion of the main body to inhibit contamination.

There is yet additionally provided, in accordance with an application of the present invention, apparatus for use with a suction source, the apparatus including:

a cleaning catheter, which includes (a) an elongate, flexible, tubular main body, which is shaped so as to define a distal-most suction orifice and one or more lateral suction orifices, and (b) an inflatable element, which is mounted to the main body axially between (i) the distal-most suction orifice and (ii) the one or more lateral suction orifices; and an input module, which is coupled to the cleaning catheter, and includes a flow regulator, which is configured to modulate relative levels of suction delivered by the suction source to (a) the distal-most suction orifice and (b) the one or more lateral suction orifices.

For some applications, the flow regulator is configured to modulate the relative levels of suction between at least two levels that include:

a relatively low distal-most level, in which a level of suction delivered to the distal-most suction orifice is less than 25% of a level of suction delivered to one of the one or more lateral suction orifices having a greatest cross-sectional area, and a relatively high distal-most level, in which the level of suction delivered to the distal-most suction orifice is greater than 25% of the level of suction delivered to the one of the one or more lateral suction orifices having the greatest cross-sectional area.

For some applications, the flow regulator is configured to modulate the relative levels of suction between the at least two levels that include:

the relatively low distal-most level, in which the level of suction delivered to the distal-most suction orifice is less than 10% of the level of suction delivered to the one of the one or more lateral suction orifices having the greatest cross-sectional area, and the relatively high distal-most level, in which the level of suction delivered to the distal-most suction orifice is greater than 10% of the level of suction delivered to the one of the one or more lateral suction orifices having the greatest cross-sectional area.

For some applications:

the cleaning catheter further includes a suction lumen arranged along the main body, in fluid communication with the distal-most suction orifice and the lateral suction orifices, and the flow regulator is configured to modulate the relative levels of suction by reversibly modulating a level of occlusion of the suction lumen at a portion thereof axially between (a) the distal-most suction orifice and (b) the one or more lateral suction orifices.

For some applications, the cleaning catheter further includes exactly one suction lumen arranged along the main body, in fluid communication with the distal-most suction orifice and the lateral suction orifices.

For some applications, the cleaning catheter further includes a plurality of suction lumens arranged along the main body, in fluid communication with one another and with the distal-most suction orifice and the lateral suction orifices.

For any of the applications described above:

the cleaning catheter may further include a suction lumen arranged along the main body at least partially within the main body in intermittent fluid communication with the suction source, a distal portion of the suction lumen may be in fluid communication with the distal-most suction orifice, and an outer wall of the main body is shaped so as to define an opening extending through the outer wall of the main body into the suction lumen at an axial location proximal to the distal-most suction orifice, the inflatable element may be mounted to the main body at least partially along the opening, the cleaning catheter may further include a collapsible membrane, which is at least partially positioned along the opening within an interior of the inflatable element, so as to define an inflatable chamber between a wall of inflatable element and the collapsible membrane, the collapsible membrane may be positioned to at least partially occlude the suction lumen upon at least partial inflation of the inflatable chamber, and the flow regulator may be configured to control a level of inflation of the inflatable chamber in order to modulate a level of suction delivered to the distal-most suction orifice via the suction lumen.

For some applications, a distal tip of the main body is shaped so as to define the distal-most suction orifice.

For some applications, a lateral wall of the main body is shaped so as to define the distal-most suction orifice.

For some applications, the expandable element is mounted to the main body at a location within 5 cm of a distal end of the main body.

For some applications, the collapsible membrane is configured such that upon sufficient inflation of the inflatable chamber, the collapsible membrane penetrates into the at least one of the one or more suction lumens sufficiently to cross a central longitudinal axis of the at least one of the one or more suction lumens.

For some applications, the cleaning catheter further includes one or more fluid-delivery lumens arranged along the main body, and which are in fluid communication with the inflatable chamber.

For some applications, the inflatable element has a greatest diameter of between 6 and 12 mm when fully inflated and unconstrained.

For some applications, the apparatus further includes a pliable sleeve around at least a portion of the main body to inhibit contamination.

There is also provided, in accordance with an application of the present invention, apparatus for use with a tracheal ventilation tube, a pressurized fluid source, and a suction source, the apparatus including:

a cleaning catheter, which is insertable into the ventilation tube, and which includes: (a) an elongate, flexible, tubular main body; (b) one or more fluid-delivery lumens arranged along the main body; and (c) one or more suction lumens arranged along the main body; and an input module, which is coupled to the cleaning catheter, and includes:

a flow regulator, which (a) is shaped so as to define a suction port coupleable in fluid communication with the suction source, and a fluid port coupleable in fluid communication with the pressurized fluid source, and (b) which is configured to assume at least first, second, and third activation states; and a mechanical user control element, which is configured (a) to mechanically and non-electrically set the activation states of the flow regulator, (b) to assume at least first, second, and third configurations, and (c) to transition between the first and the third configurations via the second configuration, wherein the input module is configured such that:

when the user control element is in the first configuration, the flow regulator is in the first activation state, in which the flow regulator blocks fluid communication (a) between the suction port and the one or more suction lumens and (b) between the fluid port and the one or more fluid-delivery lumens, when the user control element is in the second configuration, the flow regulator is in the second activation state, in which the flow regulator effects the fluid communication between the fluid port and the one or more fluid-delivery lumens, and blocks the fluid communication between the suction port and the one or more suction lumens, and when the user control element is in the third configuration, the flow regulator is in the third activation state, in which the flow regulator effects the fluid communication (a) between the suction port and the one or more suction lumens and (b) between the fluid port and the one or more fluid-delivery lumens.

For some applications, the first, the second, and the third configurations are first, second, and third spatial positions, respectively, and the mechanical user control element is configured to assume at least the first, the second, and the third spatial positions.

For some applications, the suction port is coupled in fluid communication with the suction source, and the fluid port is coupled in fluid communication with the pressurized fluid source.

For some applications, the suction port includes a male conical interface.

For some applications, the fluid port includes a Luer-Lok interface.

For some applications:

the main body is shaped so as to define one or more fluid-delivery orifices in fluid communication with an outer surface of the cleaning catheter, and one or more distal suction orifices, the one or more fluid-delivery lumens are arranged to transport fluid received at respective one or more proximal portions of the one or more lumens from the pressurized fluid source, to the fluid-delivery orifices, and the one or more suction lumens are arranged to convey suction from the suction source to the one or more distal suction orifices.

For some applications, a wall of the main body is shaped so as to define the one or more fluid-delivery orifices.

For some applications, the one or more fluid-delivery orifices have a total cross-sectional area in aggregate of between 0.04 and 1 mm2.

For some applications, the one or more fluid-delivery lumens are arranged along the main body at least partially within the main body.

For some applications, the one or more fluid-delivery lumens are arranged along the main body at least partially outside the main body.

For some applications, the one or more suction lumens are arranged along the main body at least partially within the main body.

For some applications, the one or more suction lumens are arranged along the main body at least partially outside the main body.

For some applications, the apparatus is for use with a ventilator, and the apparatus further includes a tube-connector assembly, which is configured to couple the ventilation tube in fluid communication with the ventilator, in a substantially air-tight manner.

For some applications, the apparatus further includes a pliable sleeve around at least a portion of the main body to inhibit contamination.

For any of the applications described above, the cleaning catheter may further include an expandable element, which is mounted to the main body at a location within 3 cm of at least one of the one or more distal suction orifices, and is expandable into contact with an inner surface of the ventilation tube.

For some applications, the location at which the expandable element is mounted to the main body is within 5 cm of a distal end of the main body.

For some applications, a wall of the inflatable element is shaped so as to define the one or more fluid-delivery orifices.

For some applications, the expandable element includes an inflatable element.

For some applications, the input module is configured such that the flow regulator, when in the first operating state, effects fluid communication between the inflatable element and the suction port, such that the inflatable element is deflated by the suction delivered via the suction port.

For some applications, the inflatable element includes a balloon.

For some applications, the inflatable element has a greatest diameter of between 6 and 12 mm when fully inflated and unconstrained.

For some applications, the cleaning catheter is configured such that an interior of the inflatable element is in fluid communication with at least one of the one or more fluid-delivery lumens, such that when the flow regulator is in the third activation state, the flow regulator effects fluid communication between the fluid port and the interior of the inflatable element, thereby inflating the inflatable element.

For some applications, the input module is configured such that the flow regulator, when in the second activation state, in addition to effecting the fluid communication between the fluid port and the one or more fluid-delivery lumens, and blocking the fluid communication between the suction port and the one or more suction lumens, effects suction fluid communication between suction port and the one or more fluid-delivery lumens, thereby deflating the inflatable element.

For some applications, the input module is configured such that the flow regulator, when in the first activation state, in addition to blocking the fluid communication (a) between the suction port and the one or more suction lumens and (b) between the fluid port and the one or more fluid-delivery lumens, effects fluid communication between the suction port and the one or more fluid-delivery lumens, thereby deflating the inflatable element.

For some applications:
the flow regulator further includes a valve, which is in fluid communication with the suction port, and
the input module is configured such that the flow regulator, when in the first activation state, in addition to blocking the fluid communication (a) between the suction port and the one or more suction lumens and (b) between the fluid port and the one or more fluid-delivery lumens: (a) when the valve is in an open position, effects fluid communication between the suction port and the one or more fluid-delivery lumens, thereby deflating the inflatable element, and (b) when the valve is in a closed position, blocks fluid communication between the suction port and the one or more fluid-delivery lumens.

For some applications, at least one of the fluid-delivery orifices is located within 10 cm of the expandable element.

For some applications:
the one or more suction lumens include (a) at least a first suction lumen and (b) at least a second suction lumen,
the one or more distal suction orifices include (a) one or more first distal suction orifices, all of which first distal suction orifices are located proximal to the expandable element, and (b) one or more second suction orifices, all of which second distal suction orifices are located distal to the expandable element,
the at least a first suction lumen is arranged to convey the suction from the suction source to the one or more first distal suction orifices, and
the at least a second suction lumen is arranged to convey the suction from the suction source to the one or more second distal suction orifices.

For some applications, the input module is configured such that the flow regulator, when in at least one of the first, the second, and the third activation states, delivers the suction through the one or more second distal suction orifices at a strength that is weaker than 20% of the suction force applied through a largest one of the one or more first distal suction orifices, and, in at least another of the activation states, delivers the suction through the one or more second distal suction orifices at a strength that at a strength that is stronger than 20% of the suction force through the applied through the largest of the first distal suction orifices.

For some applications, the one or more fluid-delivery orifices are located within 3 cm of the expandable element.

For any of the applications described above, the mechanical user control element may include an axial-motion element, which is configured to assume at least first, second, and third axial positions along a single axis, when the mechanical user control element is in the first, the second, and the third configurations, respectively, and the second axial position is spatially between the first and the second axial positions along the axis.

For any of the applications described above, the main body may include a proximal-most input portion, which is inserted into and axially slidable with respect to the input module. For some applications, the input module is configured such that changes in configuration of the mechanical user control element cause corresponding changes in axial position of the input portion of the main body with respect to the input module. For some applications, the input module is configured such that the input portion assumes first, second, and third axial positions with respect to the input module, corresponding to the first, the second, and the third configurations of the mechanical user control element.

For any of the applications described above, the input module may further include a state protective selector, which is configured to provide a plurality of protective states, including:
a protective selector first state, in which the state protective selector locks mechanical user control element in the first configuration,
a protective selector second state, in which the state protective selector allows the mechanical user control element to move only between the first configuration and the second configuration, and
a protective selector third state, in which the state protective selector allows the mechanical user control element to reach the first, the second, and the third configurations.

There is further provided, in accordance with an application of the present invention, a method for use with a tracheal ventilation tube, a pressurized fluid source, and a suction source, the method including:

coupling, in fluid communication with the suction source, a suction port of a flow regulator of an input module;

coupling, in fluid communication with the pressurized fluid source, a fluid port of the flow regulator;

inserting a cleaning catheter into the ventilation tube inserted in a trachea of a patient, which cleaning catheter is coupled to the input module and includes (a) an elongate, flexible, tubular main body, (b) one or more fluid-delivery lumens arranged along the main body, and (c) one or more suction lumens arranged along the main body; and activating a mechanical user control element to assume at least first, second, and third configurations, including transitioning between the first and the third configurations via the second configuration, so as to mechanically and non-electrically set the activation states of the flow regulator, such that:

when the user control element is in the first configuration, the flow regulator is in a first activation state, in which the flow regulator blocks fluid communication (a) between the suction port and the one or more suction lumens and (b) between the fluid port and the one or more fluid-delivery lumens, when the user control element is in the second configuration, the flow regulator is in a second activation state, in which the flow regulator effects the fluid communication between the suction port and the one or more suction lumens, and blocks the fluid communication between the fluid port and the one or more fluid-delivery lumens, and when the user control element is in the third configuration, the flow regulator is in a third activation state, in which the flow regulator effects the fluid communication (a) between the suction port and the one or more suction lumens and (b) between the fluid port and the one or more fluid-delivery lumens.

There is still further provided, in accordance with an application of the present invention, a method for use with a tracheal ventilation tube and a suction source, the method including:

coupling, in fluid communication with the suction source, a suction port of a flow regulator of an input module;

inserting a cleaning catheter into the ventilation tube inserted in a trachea of a patient, which cleaning catheter (a) is coupled to the input module, (b) is shaped so as to define one or more distal suction orifices, and (c) includes (i) an elongate, flexible, tubular main body, (ii) one or more fluid-delivery lumens arranged along the main body, (iii) one or more suction lumens arranged along the main body, and (iv) an inflatable element, which is mounted to the main body at a location within 3 cm of at least one of the one or more distal suction orifices;

activating the flow regulator to assume a first activation state, in which the flow regulator effects fluid communication between the suction source and an interior of the inflatable element via at least one of the one or more fluid-delivery lumens, thereby deflating the inflatable element; and activating the flow regulator to assume a second activation state, in which the flow regulator effects fluid communication between the suction source and the distal suction orifices via the one or more suction lumens, and does not effect the fluid communication between the suction source and the interior of the inflatable element.

There is additionally provided, in accordance with an application of the present invention, a method for use with a tracheal ventilation tube, the method including:

providing a cleaning catheter that is shaped so as to define one or more fluid-delivery orifices in fluid communication with an outer surface of the cleaning catheter, and includes an elongate, flexible, tubular main body, and an inflatable element, which is mounted to the main body, and the one or more fluid-delivery orifices are in fluid communication with an interior of the inflatable element; and inserting the cleaning catheter into the ventilation tube inserted in a trachea of a patient.

There is yet additionally provided, in accordance with an application of the present invention, a method for use with a suction source, the method including:

providing a cleaning catheter, which includes (a) an elongate, flexible, tubular main body, which is shaped so as to define a distal-most suction orifice and one or more lateral suction orifices, and (b) an inflatable element, which is mounted to the main body axially between (i) the distal-most suction orifice and (ii) the one or more lateral suction orifices; and modulating relative levels of suction delivered by the suction source to (a) the distal-most suction orifice and (b) the one or more lateral suction orifices.

For some applications, modulating includes modulating the relative levels of suction between at least two levels that include:

a relatively low distal-most level, in which a level of suction delivered to the distal-most suction orifice is less than 25% of a level of suction delivered to one of the one or more lateral suction orifices having a greatest cross-sectional area proximal to the inflatable element, and a relatively high distal-most level, in which the level of suction delivered to the distal-most suction orifice is greater than 25% of the level of suction delivered to the one of the one or more lateral suction orifices having the greatest cross-sectional area proximal to the inflatable element.

For some applications, modulating includes modulating the relative levels of suction between the at least two levels that include:

the relatively low distal-most level, in which the level of suction delivered to the distal-most suction orifice is less than 10% of the level of suction delivered to the one of the one or more lateral suction orifices having the greatest cross-sectional area, and the relatively high distal-most level, in which the level of suction delivered to the distal-most suction orifice is greater than 10% of the level of suction delivered to the one of the one or more lateral suction orifices having the greatest cross-sectional area.

For some applications:

the cleaning catheter further includes a suction lumen arranged along the main body, in fluid communication with the distal-most suction orifice and the lateral suction orifices, and modulating the relative levels of suction includes reversibly modulating a level of occlusion of the suction lumen at a portion thereof axially between (a) the distal-most suction orifice and (b) the one or more lateral suction orifices.

For some applications, providing the cleaning catheter includes providing the cleaning catheter further including exactly one suction lumen arranged along the main body, in fluid communication with the distal-most suction orifice and the lateral suction orifices.

For some applications, providing the cleaning catheter includes providing the cleaning catheter further including a plurality of suction lumens arranged along the main body, in fluid communication with one another and with the distal-most suction orifice and the lateral suction orifices.

For some applications, the method further includes, before modulating the relative levels of suction, inserting the cleaning catheter into a ventilation tube inserted in a trachea of a patient.

There is also provided, in accordance with an application of the present invention, a method for use with a tracheal ventilation tube, a pressurized fluid source, and a suction source, the method including:

coupling, in fluid communication with the suction source, a suction port of a flow regulator of an input module;

coupling, in fluid communication with the pressurized fluid source, a fluid port of the flow regulator;

inserting a cleaning catheter into the ventilation tube inserted in a trachea of a patient, which cleaning catheter is coupled to the input module and includes (a) an elongate, flexible, tubular main body, (b) one or more fluid-delivery lumens arranged along the main body, and (c) one or more suction lumens arranged along the main body; and activating a mechanical user control element to assume at least first, second, and third configurations, including transitioning between the first and the third configurations via the second configuration, so as to mechanically and non-electrically set the activation states of the flow regulator, such that:

when the user control element is in the first configuration, the flow regulator is in the first activation state, in which the flow regulator blocks fluid communication (a) between the suction port and the one or more suction lumens and (b) between the fluid port and the one or more fluid-delivery lumens, when the user control element is in the second configuration, the flow regulator is in the second activation state, in which the flow regulator effects the fluid communication between the fluid port and the one or more fluid-delivery lumens, and blocks the fluid communication between the suction port and the one or more suction lumens, and when the user control element is in the third configuration, the flow regulator is in the third activation state, in which the flow regulator effects the fluid communication (a) between the suction port and the one or more suction lumens and (b) between the fluid port and the one or more fluid-delivery lumens.

The present invention will be more fully understood from the following detailed description of embodiments thereof, taken together with the drawings, in which:

BRIEF DESCRIPTION OF THE DRAWINGS

FIG. 3 is a schematic illustration of a portion of a proximal portion of the main body of FIG. 2, in accordance with an application of the present invention;

FIGS. 4A-C are schematic illustrations of several states of a flow regulator of an input module of the cleaning system of FIG. 1A-C, in accordance with an application of the present invention;

FIGS. 6A-B are schematic illustrations of an input module and a portion of a main body of the cleaning system of FIGS. 1A-C, in accordance with an application of the present invention;

FIG. 8 is a schematic illustration of a portion of a proximal portion of a main body of the cleaning system of FIGS. 1A-C, in accordance with an application of the present invention;

FIGS. 9A-C are schematic illustrations of several states of a flow regulator of a input module of the cleaning system of FIGS. 1A-C, in accordance with an application of the present invention;

FIGS. 17A-C are schematic illustrations of another configuration of an input module of the cleaning system of FIGS. 1A-C, in accordance with an application of the present invention;

FIGS. 19A-C are schematic illustrations of an input module of the cleaning system of FIGS. 1A-C, in accordance with an application of the present invention;

FIGS. 19D-F are schematic illustrations of buttons of the input module of FIGS. 19A-C, in accordance with an application of the present invention;

FIG. 23 is a schematic illustration of a portion of a proximal portion of a main body of a closed suction cleaning system, in accordance with an application of the present invention; and FIGS. 24A-C are schematic illustrations of several states of a flow regulator of a input module of the cleaning system of FIG. 23, in accordance with an application of the present invention.

DETAILED DESCRIPTION OF APPLICATIONS

Figure 1A:
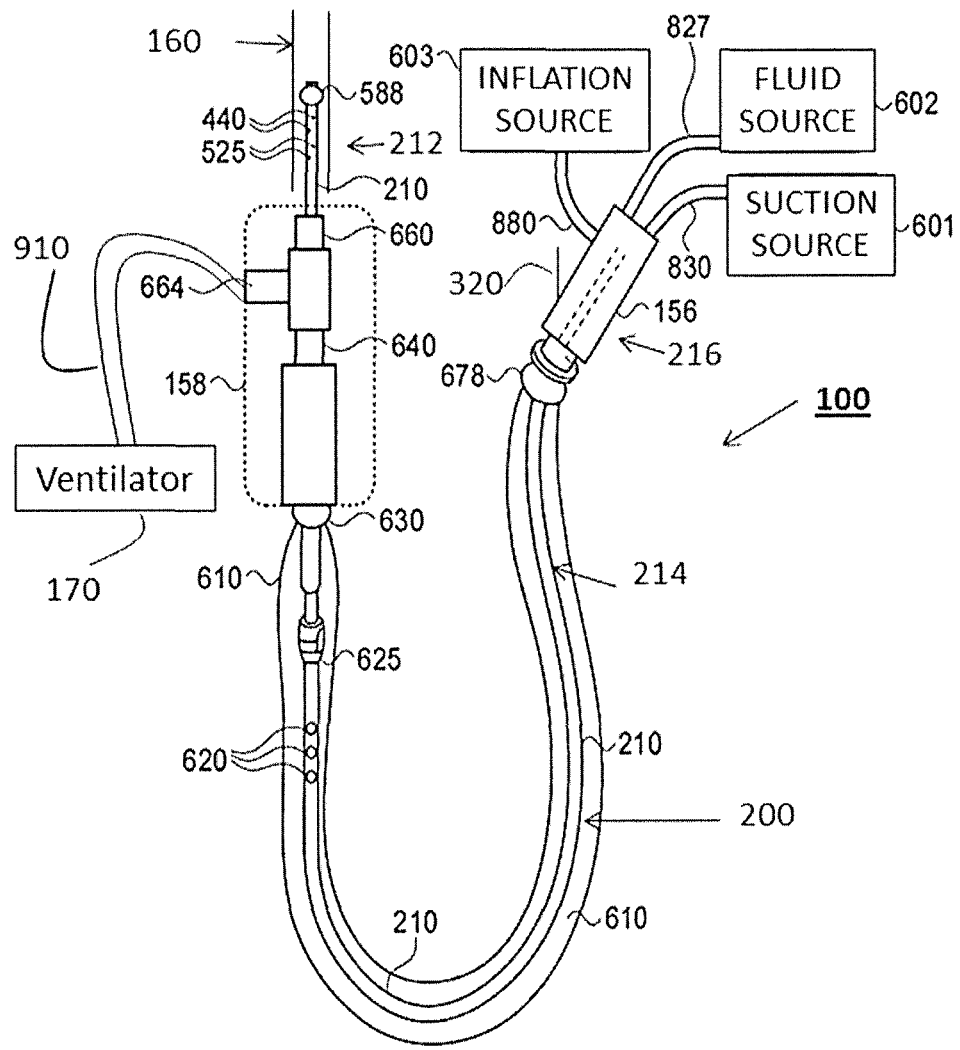
FIGS. 1A-D are schematic illustrations of a closed suction cleaning system, in accordance with respective applications of the present invention.

FIGS. 1A-D are schematic illustrations of a closed suction system cleaning system 100, in accordance with respective applications of the present invention. Cleaning system 100 is configured for use with a tracheal ventilation tube 160, a ventilator 170, a pressurized fluid source 602, a suction source 601, and, optionally, an inflation source 603, which may comprise, for example, a conventional syringe. Some of the configurations described herein, such as with reference to FIGS. 1A, 3, and 4A-C, and 5A-C, provide inflation source 603, while other configurations, such as described with reference to FIGS. 1B-D, 7A-B, 8 and 9A-C, 10 and 11A-C, 12 and 13A-B, 14 and 15A-B, 16A-C, 17A-C, 19A-C, 18A-C, 21A-B and 22A-C, and 23 and 24A-C, do not provide inflation source 603. Some applications of the present invention provide a closed suction cleaning system that is configured to be coupled to (e.g., is coupled to) pressured fluid source 602 and suction source 601, and not to an independent inflation source, such as a syringe. For some applications, cleaning system 100 comprises one or more of tracheal ventilation tube 160, ventilator 170, pressurized fluid source 602, suction source 601, and/or an inflation source 603, in any combination.

As used in the present application, including in the claims, a "tracheal ventilation tube" comprises an endotracheal tube (ETT) or a tracheostomy tube. Suction source 601 provides a pressure less than one atm, and pressurized fluid source 602 provides a pressure greater than one atm. As used in the present application, including in the claims, a "fluid" comprises liquid and/or gas, for example, a liquid-gas mixture that is predominantly liquid, such as a liquid with gas bubbles. The liquid may comprise water, such as saline solution or a disinfectant solution.

Cleaning system 100 comprises a distal ventilation tube connector assembly 158, a flexible, a cleaning catheter 200, and an input module 156. Cleaning catheter 200 comprises a main body 210. Cleaning catheter 200 includes a distal portion 212 located distal to ventilation tube connector 158, and a proximal portion 214 located proximal to ventilation tube 158. Distal portion 212 is configured to be inserted into ventilation tube 160. Proximal portion 214 includes a proximal-most input portion 216 of main body 210, which is configured to be inserted into input module 156. For some applications, proximal-most input portion 216 is axially slidable with respect to input module 156, while for other applications, the proximal-most input portion is axially fixed with respect to the input module. Respective lengths of distal and proximal portions 212 and 214 may depend on an extent to which a distal end is deployed within ventilation tube 160 and/or an extent to which the distal end is longitudinally displaced from ventilation tube connector assembly 158, for example, an extent to which main body 210 slides through ventilation tube connector assembly 158 in a distal direction.

Ventilation tube connector assembly 158 comprises: (a) a ventilator port 664, configured to be coupled in fluid communication with ventilator 170, (b) a ventilation tube port 660, configured to be coupled in fluid communication with a proximal end of ventilation tube 160, and (c) a main body inlet 640, which is configured to allow passage therethrough of elongate main body 210.

In some applications of the present invention, cleaning system 100 is operative to clean an interior of ventilation tube 160 when ventilation tube connector assembly 158 is directly or indirectly connected to both ventilation tube 160 and ventilator 900 so as to mediate a substantially air-tight connection (e.g., via an interior chamber(s) and/or conduit(s) of ventilation tube connector assembly 158) between the ventilator and an interior of the ventilation tube. In one non-limiting example, an interior region and/or outer shape of ventilation tube port 660 matches a proximal end of ventilation tube 160 to create a substantial air-tight seal. In another non-limiting example, a tube 910 or other conduit of a tube assembly may be connected to ventilator port 664 so that an interior of ventilator port 664 receives air from the ventilator and is in fluid communication with ventilator 900 in a substantially air-tight manner.

For some applications, cleaning catheter 200 further comprises an expandable element 588, mounted to flexible main body 210 near a distal end of flexible main body 210, e.g., within 5 cm, e.g., within 3 cm, of the distal end, and/or in a distal half of distal portion 212 of cleaning catheter 200, such as a distal third, a distal fifth, or a distal tenth of distal portion 212. Alternatively or additionally, expandable element 588 is mounted to flexible main body 210 within 3 cm of at least one of the one or more distal suction orifices 440. Expandable element 588 is expandable into contact with an inner surface 201 of ventilation tube 160. For some applications, expandable element 588 has a greatest outer diameter of at least 6 mm, no more than 12 mm, and/or between 6 and 12 mm when fully expanded (e.g., inflated) and unconstrained (i.e., not constrained by the ventilation tube or anything else), which is typically slightly greater than an inner diameter of ventilation tube 160, in order to provide sealing contact with inner surface 201 of the ventilation tube. For some applications, main body 210 has an outer diameter of at least 6 mm, no more than 12 mm, and/or between 6 and 12 mm. For some applications, the greatest outer diameter of expandable element 588 when fully expanded (e.g., inflated) and unconstrained (i.e., not constrained by the ventilation tube or anything else) equals at least 60%, no more than 120%, and/or between 60% and 120% of the outer diameter of main body 210.

When expanded, expandable element 588 typically provides two types of functionality: (i) flow obstruction functionality to significantly hinder fluid flow between locations on opposite longitudinal sides of the expandable element (as discussed below with reference to FIG. 21B, this may be useful for concentrating suction so that the suction is predominantly in a proximal portion 774 of the lumen of the ventilation tube 160 proximal to the expandable element 588), and/or (ii) a wiping functionality useful for cleaning inner surface 201 of ventilation tube 160. Typically, cleaning system 100 operates in a closed system environment.

For some applications, expandable element 588 comprises an inflatable element, such as a balloon, which is configured to expand upon being inflated. For other applications, expandable element 588 expands other than by inflation; for example, expandable element 588 may comprise a deformable element such as a gel, a foam, a fluid compartment, or a wire mesh or braid, which can be deformed to expand its width in the direction perpendicular to the main body longitudinal axis, either with or without an overall change in volume.

During one state of operation, cleaning system 100 cleans inner surface 201 of ventilation tube 160 when ventilation tube connector assembly 158 mediates a substantially airtight seal between (i) ventilator 900 and/or an interior of ventilator port 664 and (ii) an interior of ventilation tube 160 and/or an interior of ventilation tube port 660 (this substantially air-tight seal is referred to hereinbelow as the "ventilation machine-ventilator tube seal").

As is described below, concurrent with maintaining of this ventilation machine-ventilator tube seal, expandable element 588 may be positioned within ventilation tube 160 (e.g., in a distal portion of ventilation tube 160), for example by moving a distal end of main body 210 in a distal direction towards a distal end of ventilation tube 160. For example, expandable element 588 may be distally advanced when expandable element 588 is in a non-contact state (i.e., not in contact with inner surface 201 of ventilation tube 160). After expandable element 588 is thus positioned, expansion of the expandable element induces contact between an outer surface of expandable element 588 and the inner surface of ventilation tube 160 and/or obstructs (i.e., significant hinders) longitudinal flow between proximal and distal portions of the interior of ventilation tube 160. As is described below, this slidable boundary between the proximal and distal portions may be useful for facilitating the cleaning of the inner surface of ventilation tube 160, for example for substantially confining locations of negative pressure and/or fluid (e.g., pressurized fluid) introduced into an interstitial region outside of main body 210 and within ventilation tube 160 so that the suction or pressurized fluid is introduced predominantly in the proximal portion of ventilation tube 160.

For some applications, distal portion 212 of cleaning catheter 200 is shaped so as to define one or more fluid-delivery orifices 525. Alternatively or additionally, for some applications, one or more fluid-delivery orifices 525 are defined by a wall of expandable element 588, such as described hereinbelow with reference to FIGS. 7B and/or 21A-B. Fluid-delivery orifices 525 are in fluid communication with an outer surface of cleaning catheter 200 (including with an outer surface of main body 210) and an outer surface of expandable element 588 (typically a proximal side of the outer surface), including when distal portion 212 of cleaning catheter 200 is inserted into ventilation tube 160. For some applications, one or more fluid-delivery orifices 525 are defined by a wall of main body 210, such as described herein with reference to FIGS. 1A, 1B, 1D, and 7A. Alternatively or additionally, for some applications, distal portion 212 of cleaning catheter 200 comprises one or more distal suction orifices 440, typically through a lateral wall of distal portion 212. Typically, one or more distal suction orifices 440 are located along distal portion 212 at one or more respective locations proximal to inflatable element 588. Typically, at least one of fluid-delivery orifices 525 (such as all of one or more fluid-delivery orifices 525) is located within 10 cm of the expandable element 588, such as within 5 cm, e.g., within 3 cm of the expandable element. For some applications, fluid-delivery orifices 525 have a total cross-sectional area in aggregate of at least 0.04 mm2, no more than 1 mm2, and/or between 0.04 mm2 and 1 mm2.

For some applications, distal suction orifices 440 are supplied with negative pressure by suction source 601 and facilitate cleaning of the inner surface of ventilation tube 160. For some applications, material within the interior of ventilation tube 160 may be suctioned into distal suction orifices 440 and proximally transported out of ventilation tube 160, e.g., to a location that is proximal to ventilation tube connector assembly 158. As described below in detail, fluid communication between suction source 601 and/or pressurized fluid source 602 and suction and/or fluid-delivery orifices 440 and/or 525 may be provided by one or more connecting lumens within or along the main body 210. As used in the present application, including in the claims, "fluid communication" includes both positive and negative pressure fluid communication, and thus includes, for example, communication of a positive pressure or of a suction force.

For some applications, cleaning system 100 comprises a substantially impermeable and/or pliable sleeve 610 for protecting an outer surface of main body 210. In some embodiments, sleeve 610 envelops, surrounds, and/or protects at least some (e.g., at least a majority or at least a substantial majority, e.g., at least 75% or substantially all of (e.g., at least 90%)) of an outer surface of a ventilation-tube-connector-assembly-proximal portion 214 of elongate main body 210, typically in locations proximal to tube-connector assembly 158 and distal to suction port 830, and typically to inhibit contamination. For some applications, sleeve 610 provides this enveloping and/or protection functionality when a length of the ventilation-tube-connector-assembly-proximal portion 214 of main body 210 is at least 3 cm, e.g., at least 5 cm, at least 7 cm, or at least 10 cm.

For some applications, a length of proximal portion 214 may be modified by sliding, in a proximal or distal direction, main body 210 through ventilation tube connector assembly 158.

For some applications, a distal end of sleeve 610 is (i) directly or indirectly attached to and/or (ii) has a location that is fixed and/or longitudinally fixed relative to ventilation tube connector assembly 158. For some applications, a longitudinal position of a location of the distal end of sleeve 610 corresponds to a location on ventilation tube connector assembly 158 (e.g., at or near main body inlet 640) and/or is longitudinally displaced from a proximal end (e.g., corresponding to main body inlet 640) of ventilation tube connector assembly 158 by at most 5 cm, e.g., at most 3 cm, at most 2 cm, or at most 1 cm, and/or at most 50%, e.g., at most 30%, at most 20%, at most 10% of a length of ventilation-tube-connector-assembly-proximal portion 214 of main body 210.

For some applications, a location of the distal end of sleeve 610 is not fixed relative to main body 210. For example, main body 210 may be longitudinally slidable within the sleeve 610 at or near a location of the distal end. Alternatively or additionally, for some applications, a location of a proximal end of sleeve 610 is fixed and/or longitudinally fixed relative to a proximal end of main body 210. For some applications, sleeve 610 forms a substantially air-tight seal between the external environment and an outer surface of ventilation-tube-connector-assembly-proximal portion 214 of main body 210 and/or between the external environment and region of space outside of an outer surface of ventilation-tube-connector-assembly-proximal portion 214 of main body 210 and within sleeve 610.

Figure 1B:
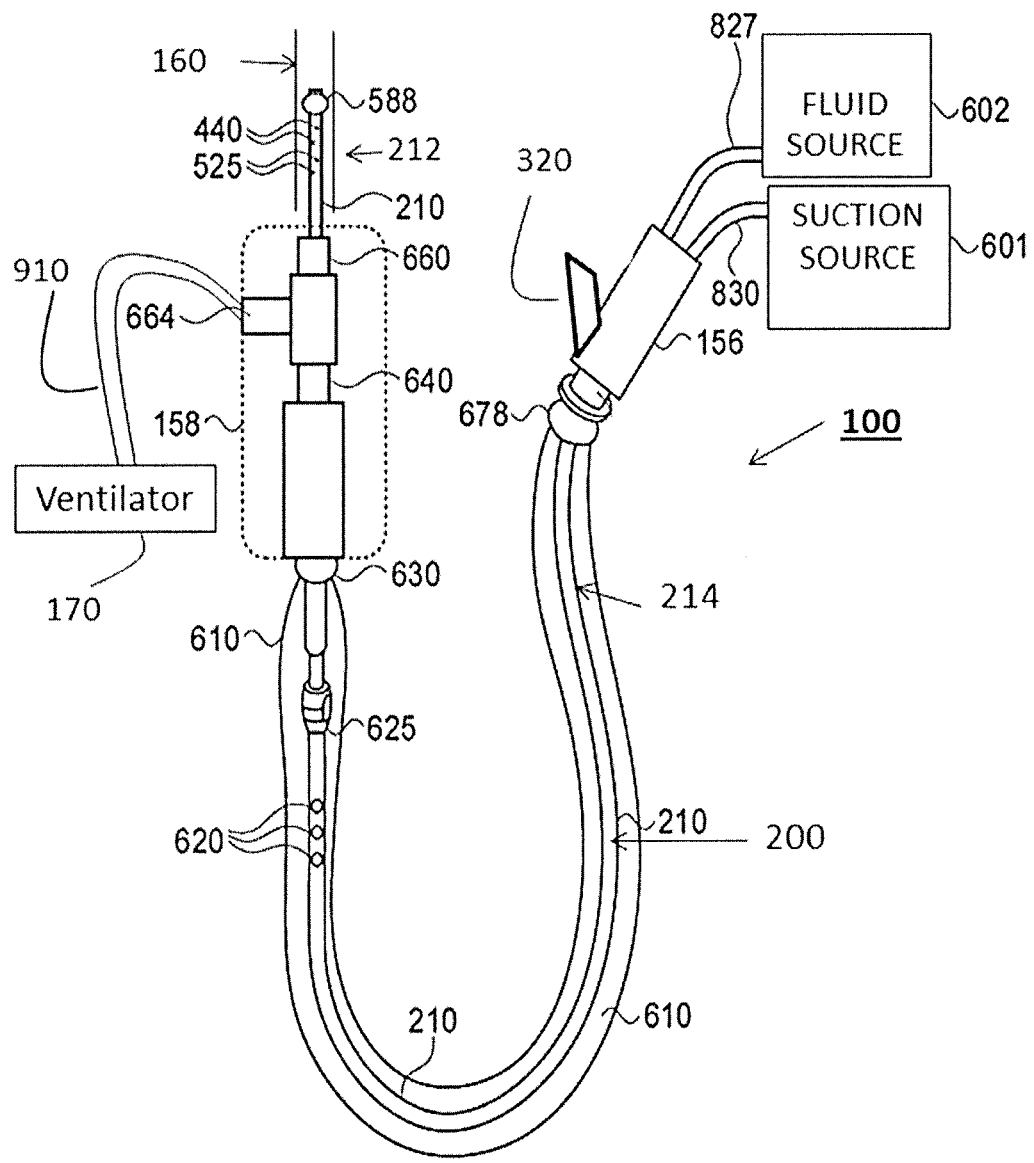
Figure 1C:
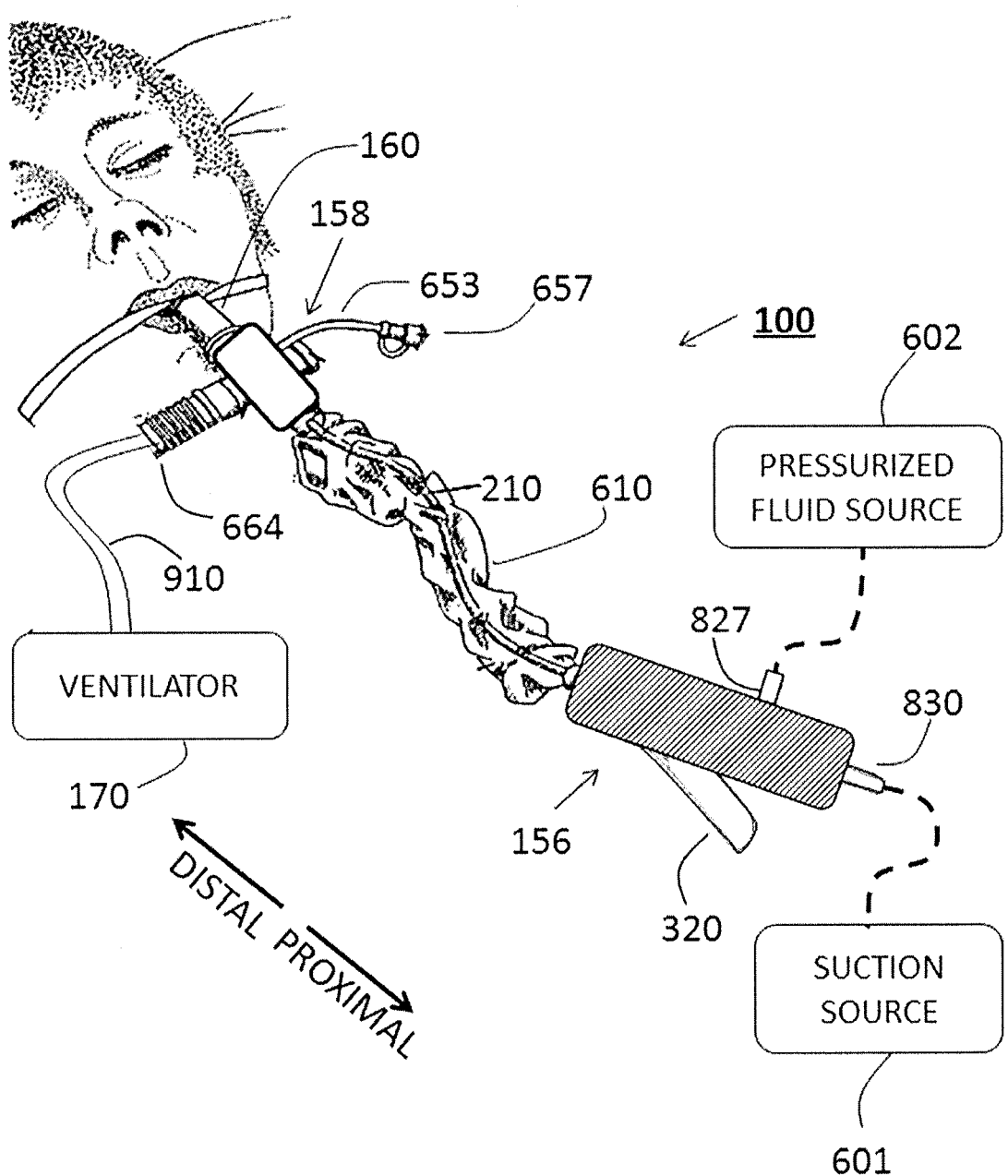
Figure 1D:
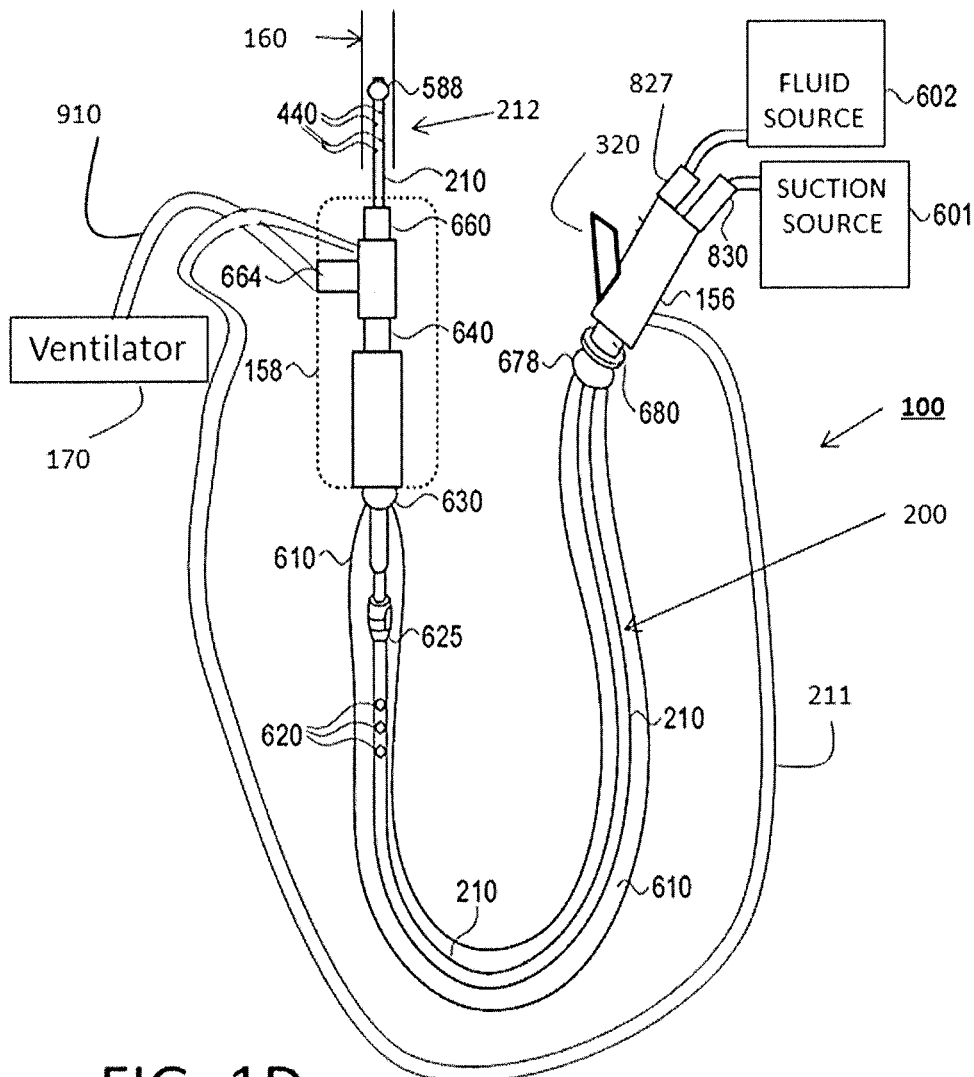

Reference is made to FIG. 1D. In this configuration of cleaning system 100, fluid-delivery orifices 525 are not provided, and one or more fluid-delivery lumens 520, described hereinbelow with reference to FIG. 2, may not be provided. Instead, a separate secondary tube 211, distinct from main body 210, is provided for delivering irrigation fluid to trickle down from the proximal (top) end of ventilation tube 160 when the distal end of distal portion 212 of cleaning catheter 200 is already inserted into the distal portion of the ventilation tube and suctioning is activated. Secondary tube 211 provides fluid communication between input module 156 and distal ventilation tube connector assembly 158, and allows delivery of irrigation fluid to be controlled by a flow regulator of input module 156. For some applications, inflation lumen 580, described hereinbelow with reference to FIG. 2, is provided for inflating expandable element 588.

Reference is made to FIGS. 1A, 1B, and 1C. For some applications, depth markings 620 are provided on catheter main body 210. For some applications, a stopper element 625 is attached to catheter main body 210. For some applications, an interface 630 is provided between a distal end of pliable sleeve 610 and connector assembly 158. For some applications, an interface 678 is provided between a proximal end of pliable sleeve 610 and input module 156.

Figure 2:
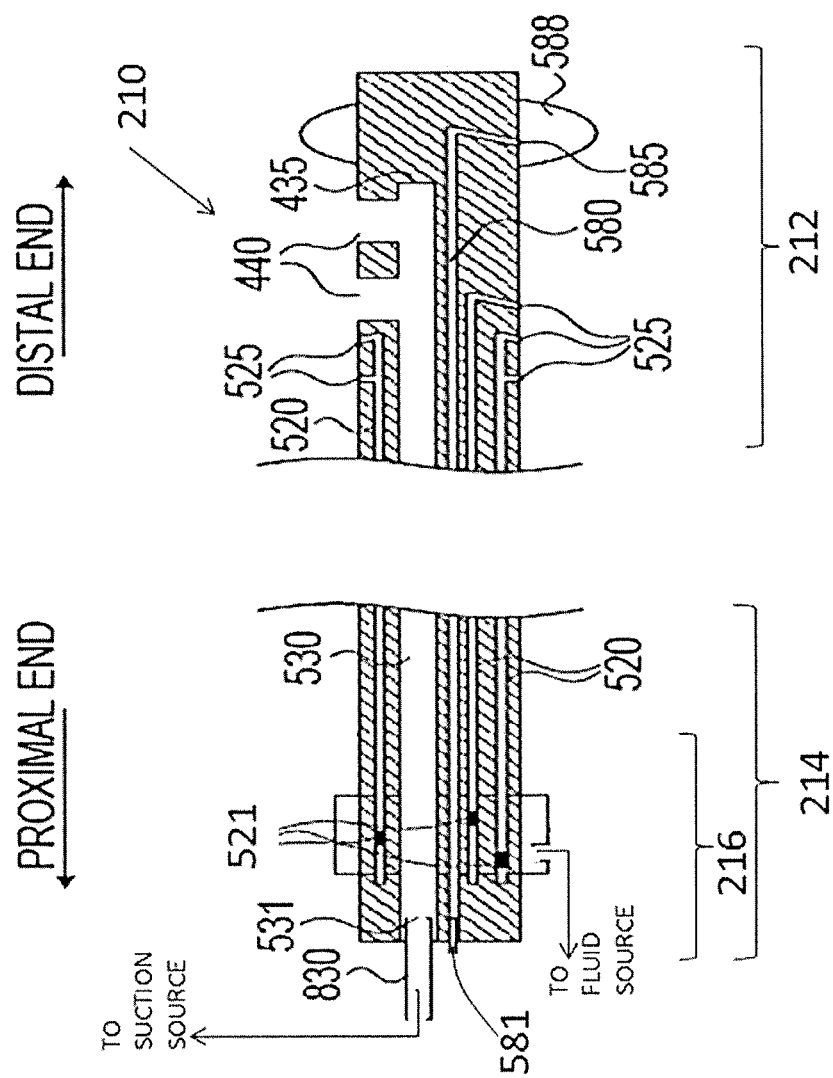
FIG. 2 is a schematic illustration of a main body of the cleaning system of FIGS. 1A-C, in accordance with an application of the present invention.

Reference is now made to FIG. 2, which is a schematic illustration of main body 210, in accordance with an application of the present invention. Main body includes one or more of the following lumens arranged along main body 210. For some applications, one or more of the lumens are arranged along main body 210 at least partially within the main body, e.g., integrally formed in the main body 210, formed in the wall of main body 210, or provided as a separate tube with main body 210. Alternatively or additionally, one or more of the lumens are arranged along main body 210 at least partially outside the main body, e.g., provided as a separate tube outside main body 210). The lumens include:

one or more fluid-delivery lumens 520, which provide fluid communication between at least one proximal fluid-delivery inlet 521 and one or more respective fluid-delivery orifices 525 (and, optionally, for some applications, expandable element 588, as described hereinbelow); typically, input portion 216 is shaped so as to define proximal fluid-delivery inlet 521, and distal portion 212 of cleaning catheter 200 is shaped so as to define fluid-delivery orifices 525;

one or more suction lumens 530, which provide fluid communication between at least one proximal suction inlet 531 and one or more distal suction orifices 440; typically, input portion 216 of main body 210 is shaped so as to define proximal suction inlet 531, and distal portion 212 of cleaning catheter 200 is shaped so as to define distal suction orifices 440. The one or more suction lumens are arranged in intermittent fluid communication with fluid source 601, as described in detail hereinbelow; for applications in which the one or more suction lumens comprise a plurality of suction lumens, the one or more suction lumens typically are arranged in fluid communication with one another (and are thus typically brought into fluid communication with fluid source 601 together rather than separately); and/or at least one inflation lumen 580, which provides fluid communication between at least one inflation inlet 581 and at least one inflation outlet 585 which is in fluid communication with an interior of expandable element 588; typically, input portion 216 is shaped so as to define inflation inlet 581, and distal portion 212 is shaped so as to define inflation outlet 585.

Reference is now made to FIG. 3, which is a schematic illustration of a portion of proximal portion 214 of main body 210, in accordance with an application of the present invention. FIG. 3 shows one or more fluid-delivery lumens 520, one or more suction lumens 530, and inflation lumen 580, which have been omitted from FIGS. 4A-C for clarity of illustration. For some applications, proximal suction inlet 531 is located proximal to proximal fluid-delivery inlet 521, and/or proximal fluid-delivery inlet 521 is located proximal to inflation inlet 581. For some applications, proximal fluid-delivery inlet 521 is located longitudinally between proximal suction inlet 531 inflation inlet 581. For some applications, as shown, proximal suction inlet 531 is defined by a lateral wall of main body 210, while for other applications, proximal suction inlet 531 is defined by a proximal end of main body 210, such as shown in FIGS. 5B-C, 17A-C, and 18A-C.

Reference is made to FIGS. 4A-C, which are schematic illustrations of several states of a flow regulator 700 of input module 156, in accordance with an application of the present invention. As mentioned above, in some configurations input portion 216 of proximal portion of main body 210 is configured to be inserted into and axially slidable with respect to input module 156. Input module 156 has a plurality of ports for connection with various fluid sources, including at least suction source 601 and pressurized fluid source 602. Input module 156 comprises flow regulator 700, a mechanical user control element 320, and a housing 310 encasing input portion 216 of main body 210. Mechanical user control element 320 is shown schematically in FIGS. 4A-C and in some of the other figures; actual implementations of cleaning system 100 typically include a more ergonomic design for comfortable interface with a human hand, such as the configuration shown in FIGS. 18A-C. Typically, input module 156 comprises exactly one mechanical user control element 320 having the properties described herein, and/or system 100 comprises exactly one mechanical user control element 320 having the properties described herein. The input module and/or system may comprise further user control elements that perform control functions in addition to those performed by mechanical user control element 320.

Input module 156 is configured to assume a plurality of activation states. Mechanical control unit 320 is typically configured to mechanically and non-electrically set the states of flow regulator 700. Input module 156 is configured to set the activation states enabling or blocking fluid communication between the various lumen inlets and the external fluid sources via respective ports. For some applications, transitions between states are effected by shifts in alignment of the lumen inlets with respect to various chambers of input module 156, which chambers are or are not in fluid communication with respective ports. The shifts in alignment are typically effected via axial motion of input portion 216 of catheter main body 210 within input module housing 310, along the longitudinal axes of input portion 216 and input module 156.

For some applications, one or more of lumen inlets 521, 531, and 581 are isolated from one another by one or more fluid separators 341, 342, 343, and 344, which function as separation sealing elements. For example, the separators may comprise respective o-rings. For some applications, the separators are fixed to an outer surface of input portion 216 of main body 210, and are slidable with respect to housing 310. For some applications, such as shown in FIGS. 4A-C, the sealing elements are directly fixed to the outer surface of input portion 216, while for other applications, such as shown in FIGS. 5B-C, described hereinbelow, the sealing elements are indirectly fixed to the outer surface of input portion 216. Alternatively, the separators are fixed to housing 310, and are slidable with respect to catheter main body 210, such as described hereinbelow with reference to FIGS. 17A-C and 18A-C.

For some applications, input module 156 includes one or more of the following ports:

a fluid port 827, which is coupleable in fluid communication with pressurized fluid source 602, and coupled in fluid communication with pressurized fluid source 602 during use of cleaning system 100;

a suction port 830, which is coupleable in fluid communication with suction source 601, and coupled in fluid communication with suction source 601 during use of cleaning system 100; and/or an inflation port 832, which is coupleable in fluid communication with inflation source 603, and coupled in fluid communication with inflation source 603 during use of cleaning system 100.

Typically, fluid port 827 comprises a screw-on fitting, such as a Luer-Lock interface. Typically, suction port 830 is shaped as a conventional suction port in accordance with hospital standards for coupling to standard hospital suctions sources. For example, suction port 830 may have a male conical interface, such as described hereinbelow with reference to FIGS. 18A-C. Typically, suction port 830 has a lumen size that corresponds with the lumen size of conventional tracheal suction lumens, which generally having a gauge of between 5 Fr to 18 Fr.

For some applications, pressurized fluid from fluid source 602 is delivered, via one or more fluid-delivery lumens 520 (shown in FIG. 3) and fluid-delivery orifices 525 (shown in FIGS. 1A-D), into an interstitial region inside of ventilation tube 160 and outside of the main body 210. For some applications, a stream of the delivered fluid passes through the interstitial region en route to inner surface 201 of ventilation tube 160, and is incident upon the inner surface of the ventilation tube. The stream of the delivered fluid may comprise, for example, a liquid stream, a gas stream, and/or a stream of a gas/liquid mixture, e.g., a mist stream or a stream of liquid including bubbles. Delivery of the fluid into the interstitial region and/or to the inner surface of the ventilation tube may be useful for cleaning the inner surface of the ventilation tube.

For some applications in which expandable element 588 is inflatable, pressurized fluid or gas delivered from inflation source 603 is delivered to expandable element 588 to inflate expandable element 588 (e.g., to form a slidable boundary, as described hereinbelow).

In the exemplary configuration of cleaning system 100 shown in FIGS. 4A-C, fluid source 602 (which provides pressurized fluid) and inflation source 603 are provided as two separate elements. Alternatively, in other configurations of cleaning system (such as that described hereinbelow with reference to FIGS. 12 and 13A-B), pressurized fluid source 602 is used to both inflate expandable element 588 and to deliver fluid via fluid-delivery orifices 525. In the configuration shown in FIGS. 3 and 4A-C, expandable element 588 comprises an inflatable element 588, such as a balloon.

In the configuration illustrated in FIGS. 3 and 4A-C, main body 210 is shaped so as to define at least three lumens: one or more fluid-delivery lumens 520 (e.g., exactly one fluid-delivery lumen 520), one or more suction lumens 530 (e.g., exactly one suction lumen 530), and at least one inflation lumen 580 (e.g., exactly one inflation lumen 580), and respective at least one proximal fluid-delivery inlet 521 (e.g., exactly one proximal fluid-delivery inlet 521), at least one proximal suction inlet 531 (e.g., exactly one proximal suction inlet 531), and at least one inflation inlet 581 (e.g., exactly one inflation inlet 581). For some applications, as shown in FIGS. 3 and 4A-C and some of the other figures, inlets 521, 531, and/or 581 are defined by a lateral wall of main body 210. Alternatively or additionally, for some applications, such as described hereinbelow with reference to FIGS. 17A-C, one or more of inlets 521, 531, and/or 581 are defined by a proximal end of the main body.

In this configuration, flow regulator 700 is configured to have three principal activation states, typically associated with three configurations of mechanical user control element 320. For some applications, the three configurations are three spatial positions, respectively. In the configuration illustrated in FIGS. 4A-C, the three states are actuated by axial motion of proximal portion 214 of elongated main body 210 relative to input module housing 310:

as shown in FIG. 4A, a first activation state, in which flow regulator 700 blocks fluid communication (a) between suction port 830 and proximal suction inlet 531, and thus one or more suction lumens 530 and (b) between fluid port 827 and proximal fluid-delivery inlet 521, and thus one or more fluid-delivery lumens 520 (but not necessarily blocked from inflatable element 588); however, fluid communication can be established between inflation port 832 and inflation inlet 581, and thus to inflatable element 588 via inflation lumen 580. For some applications, this first activation state may be considered to be a base, default activation state, which optionally is set by an elastic return force element, such as described hereinbelow with reference to FIGS. 5B-C. In this particular configuration, such inflation is typically manually enabled by the user. Inflation of inflatable element 588 before applying suction via the distal suction orifices 440 may serve to isolate the lungs from the suction;

as shown in FIG. 4B, a second activation state, in which flow regulator 700 effects suction fluid communication between suction port 830 and one or more suction lumens 530 via proximal suction inlet 531, and blocks flow of cleaning fluid between fluid port 827 and one or more fluid-delivery lumens 520; and as shown in FIG. 4C, a third activation state, in which flow regulator 700 effects both (a) suction fluid communication between suction port 830 and one or more suction lumens 530 via proximal suction inlet 531, and (b) cleaning fluid communication between fluid port 827 and one or more fluid-delivery lumens 520 via proximal fluid-delivery inlet 521.

As mentioned above, mechanical user control element 320 is configured to mechanically and non-electrically set the states of flow regulator 700. Typically, mechanical user control element 320 is configured to assume at least first, second, and third configurations, and, typically, is configured to transition between the first and the third configurations via the second configuration. For some applications, the first, second, and third configurations are first, second, and third spatial positions, respectively, and mechanical user control element 320 is configured to transition between the first and the third spatial positions via the second spatial position. For example, mechanical user control element 320 is shown in FIG. 4A in its first configuration (e.g., spatial position) (right-most position), in FIG. 4B in its second configuration (e.g., spatial position) (center position), and in FIG. 4C in its third configuration (e.g., spatial position) (left-most position). Input module 156 is configured such that:

when user control element 320 is in the first configuration (e.g., spatial position), flow regulator 700 is in the first activation state, as described above;

when user control element 320 is in the second configuration (e.g., spatial position), flow regulator 700 is in the second activation state, as described above; and when user control element 320 is in the third configuration (e.g., spatial position), flow regulator 700 is in the third activation state, as described above.

Typically, in this configuration, as well as in the other configurations described herein (except with reference to FIGS. 23 and 24A-B), cleaning system 100 may be used for two different purposes:

for cleaning the lumen of tracheal ventilation tube 160—the user typically rapidly transitions user control element 320 from the first to the third configurations (e.g., spatial positions) via the second configuration (e.g., spatial position), for example, in less than one second, typically is less than 0.5 seconds. For cleaning ventilation tube 160, there is generally no benefit to putting the flow regulator in the second activation state (suction without cleaning fluid flow), rather than transitioning directly from the first activation state (suction and cleaning fluid flow both blocked) directly to the third activation state (suction and cleaning fluid flow both enabled); and for suctioning the trachea outside of and distal to ventilation tube 160—the user transitions user control element 320 from the first to the second configurations (e.g., spatial positions), and leaves the flow regulator in the second activation state (suction without cleaning fluid flow) throughout most the trachea suctioning procedure.

The user may use cleaning system 100 for both of these purposes at different times during patient care. For example, the system may be used to clean ventilation tube 160 once every six hours, and for suctioning the lungs once every three hours. The user may choose to perform these two functions serially during a single session; the user first suctions the trachea by putting user control element 320 in the second configuration, and then immediately upon conclusion of this suctioning, transitions the user control element to the third configuration to activate cleaning of the lumen of ventilation tube 160.

Typically, mechanical user control element 320 comprises an axial-motion element 318, which is configured to assume at least first, second, and third axial positions along a single axis, when mechanical user control element 320 is in the first, the second, and the third configurations (e.g., spatial positions), respectively. The first, the second, and the third axial positions of axial-motion element 318 are shown in FIGS. 4A, 4B, and 4C, respectively. The single axis is parallel with a longitudinal axis of proximal portion 214 of main body 210. The second axial position, shown in FIG. 4B, is spatially between the first and the second axial positions along the axis. For configurations in which mechanical user control element 320 is configured such that the motion of all parts thereof is along the single axis (such as shown in FIGS. 4A-C. 5A-C, 9A-C, 11A-C, 13A-B, 15A-B, 16A-C, 17A-C), mechanical user control element 320 it its entirety functions as axial-motion element 318. For other configurations in which portions of mechanical user control element 320 move in directions other than along the single axis (such as described hereinbelow with reference to FIGS. 6A-B and 18A-C), only a portion of mechanical user control element 320 functions as axial-motion element 318.

It is noted that when mechanical user control element 320 assumes the at least first, second and third configurations (e.g., spatial positions) mentioned above, either (a) the entire mechanical user control element 320 assumes these configuration (e.g., spatial positions), such as shown in FIGS. 4A-C. 5A-C, 9A-C, 11A-C, 13A-B, 15A-B, 16A-C, 17A-C, or (b) only a portion of entire mechanical user control element 320 assumes these configuration (e.g., spatial positions), such as shown in FIGS. 6A-B and 18A-C (for example, in these configurations, axis 720 remains stationary as the remainder of mechanical user control element 320, including user control handle 718 and axial-motion element 318, assume these configuration (e.g., spatial positions)).

For some applications, input module 156 is configured such that changes in configuration (e.g., spatial position) of mechanical user control element 320 (typically axial-motion element 318 thereof) cause corresponding changes in axial position of input portion 216 of main body 210 with respect to input module 156. Typically, input module 156 is configured such that input portion 216 assumes first, second, and third axial positions with respect to input module 156 (e.g., with respect to suction port 830 and/or fluid port 827), corresponding to the first, the second, and the third configuration (e.g., spatial positions) of mechanical user control element 320. The first, second, and third axial positions of input portion 216 are typically along a single axis.

As mentioned above, FIG. 4A shows flow regulator 700 in the first (blocked) state. Input portion 216 of main body 210 is encased, yet axially movable (slidable), within housing 310 of input module 156. Catheter main body 210 is slidable through a distal wall 314 of housing 310. Inflation inlet 581 is fixedly attached to a connector 880, which, for example, may comprise a screw-on fitting, such as a Luer-Lock interface, and in operation connector 880 is connected to an inflation source (e.g., a syringe). Housing 310 is shaped so as to define suction port 830 and cleaning fluid port 827 (main body 210 does not define these ports).

As input portion 216 of main body 210 axially moves within the inner compartment of housing 310, transverse sealing separators 341, 342, 343, and 344 delineate distinct chambers within the housing. When flow regulator 700 is in the first activation state, as shown in FIG. 4A, separators 342 and 343 and the outer surface of elongated main body 210 delineate a first chamber 350 around proximal fluid-delivery inlet 521, and thereby block direct fluid communication within housing 310 between proximal fluid-delivery inlet 521 and proximal suction inlet 531, and inflation inlet 581. The separators are attached to the main body and snugly pressed against the inner surface of housing 310, so that the insulated chamber around proximal fluid-delivery inlet 521 is maintained even as the main body slides a certain distance along the longitudinal axis thereof with respect the housing.

Also as shown in FIG. 4A, in the first activation state, elongated main body 210 is positioned in its closest position to a proximal end 360 of housing 310, proximal-most separator 344 creates a seal which prevents direct fluid communication between suction port 830 of housing 310 and proximal suction inlet 531 of elongated main body 210. In this base position, cleaning fluid flow is blocked within a second sealed chamber 352 delineated by separators 341 and 342 and the outer surface of elongated main body 210.

When flow regulator 700 is in the second activation state, as shown in FIG. 4B, fluid communication is established between suction port 830 of housing 310 and proximal suction inlet 531 and into one or more suction lumens 530 in elongated main body 210, yet cleaning fluid flow remains blocked within second sealed chamber 352 delineated by separators 341 and 342 and the outer surface of elongated main body 210. This activation is achieved by sliding elongated main body 210 distally along the axial direction by a limited distance such that separator 342 does not yet cross into the space of cleaning fluid port 827. Typically, this sliding motion is induced by distally pushing on mechanical user control element 320, which is coupled to elongated main body 210 and passes through a slit 312 in housing 310 which allows axial motion of mechanical user control element 320.

When flow regulator 700 is in the third activation state, as shown in FIG. 4C, fluid communication is established in first chamber 350 between fluid port 827 of housing 310 and proximal fluid-delivery inlet 521 and one or more fluid-delivery lumens 520 of elongated main body 210. Suction port 830 of housing 310 remains in fluid communication with proximal suction inlet 531 and into one or more suction lumens 530 in elongated main body 210. Therefore, in this third activation state, flow regulator 700 effects both (a) cleaning fluid flow into one or more fluid-delivery lumens 520 and (b) suction in one or more suction lumens 530 of elongated main body 210. This activation is achieved by sliding elongated main body 210 more distally along the axial direction by a limited distance such that separator 342 crosses into or passes across the space of cleaning fluid port 827. Typically, the sliding motion is induced by distally pushing on mechanical user control element 320, which is coupled to elongated main body 210 and passes through slit 312 in housing 310.

Thus, three activation states can be actuated, typically associated with three configurations (e.g., spatial positions) of mechanical user control element 320. In the configuration illustrated in FIGS. 4A-C, the three states are actuated by axial motion of input portion 216 of elongated main body 210 relative to input module housing 310:

- the first activation state, in which inflatable element 588 can be inflated, but suction flow and cleaning fluid flow is blocked;
- the second activation state, in which suction flow is enabled between one or more suction lumens 530 and suction port 830 via proximal suction inlet 531 into one or more suction lumens 530, but cleaning fluid flow into one or more fluid-delivery lumens 520 remains blocked; and
- the third activation state, in which suction flow is enabled both between one or more suction lumens 530 and suction port 830 via proximal suction inlet 531 into one or more suction lumens 530, and cleaning fluid flow into one or more fluid-delivery lumens 520 from fluid port 827 of housing 310 via proximal fluid-delivery inlet 521.

Operational safely is inherent because there is no activation state in which cleaning fluid flow is enabled without suction also being activated.

Figure 5A:
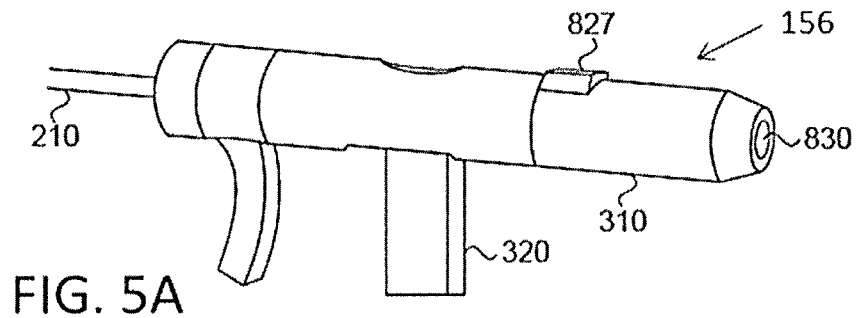
FIGS. 5A-C are schematic illustrations of an input module and a portion of a main body of the cleaning system of FIGS. 1A-C, in accordance with an application of the present invention.
Figure 5B:
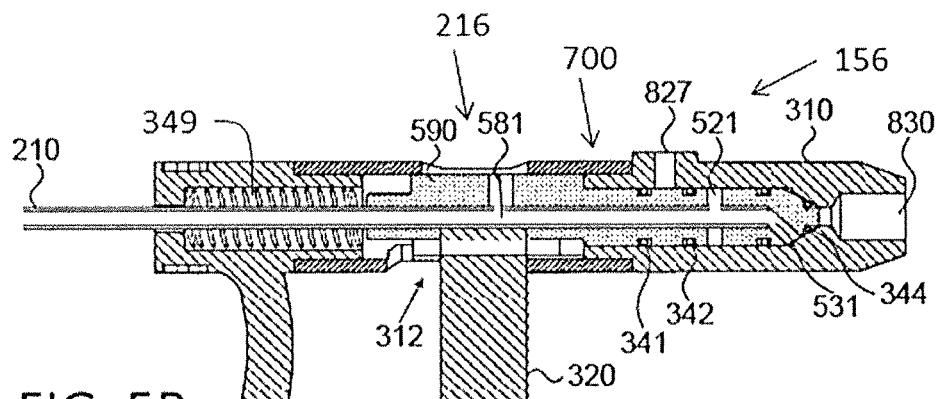
Figure 5C:
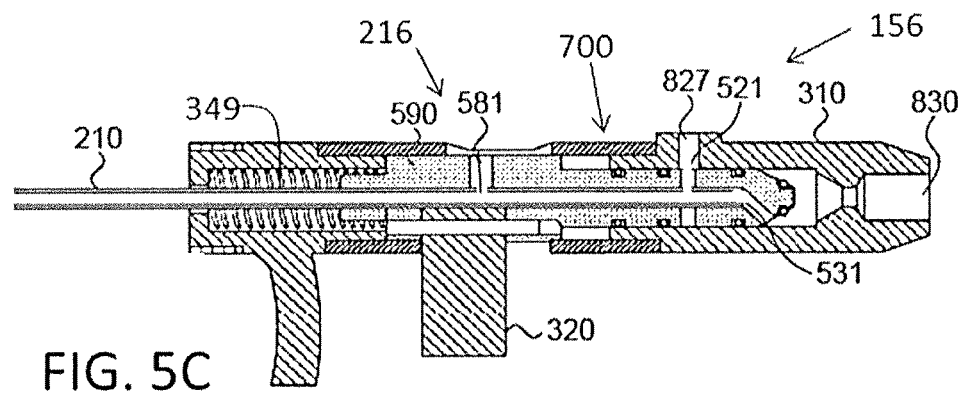

Reference is now made to FIGS. 5A-C, which are schematic illustrations of input module 156 and a portion of main body 210, in accordance with an application of the present invention. FIG. 5A is an isometric view of input module 156 with main body 210 extends distally out of a distal end of the input module. FIGS. 5B and 5C are cross-sectional views of input module 156 and the portion of main body 210. FIGS. 5B and 5C show flow regulator 700 in the first and third activation states, respectively, which are described hereinabove with reference to FIGS. 3 and 4A-C.

In the configuration shown in FIGS. 5B and 5C, input portion 216 of elongated main body 210 is attached to a mediating proximal encasing element 590, to which separators 341, 342, 343, and 344 are fixed. Thus, the sealing elements are indirectly fixed to the outer surface of input portion 216. FIGS. 5B and 5C also show an elastic return force element 349 (e.g., a spring), which sets the resting, default state of flow regulator 700 to be the first activation state.

Reference is now made to FIGS. 6A-B, which are schematic illustrations of input module 156 and a portion of main body 210, in accordance with an application of the present invention. FIGS. 6A-B illustrate an alternative mechanism for causing axial motion of catheter main body 210 relative to input module housing 310. In the configuration shown in FIGS. 4A-C, mechanical user control element 320 is pushed parallel to the axial motion of catheter main body 210. In contrast, in the configuration shown in FIGS. 6A-B, mechanical user control element 320 comprises a user control handle 718, which is configured to undergo rotational motion around an axis 720. A lever 711, which is rigidly connected to mechanical user control element 320, imparts a force having a component in catheter main body 210 axial direction onto axial-motion element 318, which may comprise, for example, a pin 730 rigidly connected to catheter main body 210. As a result, although the motion of mechanical user control element 320 includes a substantial component perpendicular to the catheter axial direction (in user control handle 718), mechanical user control element 320 nevertheless imparts an axial force onto axial-motion element 318 (e.g., pin 730), which causes axial motion of catheter main body 210 relative to input module housing 310. In other words, mechanical user control element 320 translates the movement of user control handle 718 into axial motion of axial motion element 318. In this configuration, the larger arc motion of user control handle 718 relative to the smaller motion of pin 730 and catheter main body 210 may facilitate easier human handling. This configuration may also provide a more natural human interface similar to the hand lever of bicycle brakes, which facilitates holding and activation by the human hand.

This configuration of mechanical user control element 320 may be used with any of the configurations of input module 156 described herein. In particular, in order to integrate this control arrangement into the configurations described herein, pin 730 of this configuration is substituted for mechanical user control element 320 in the other configurations, and the other elements of this configuration are added to the other configurations. Alternative configurations of mechanical user control element 320 for effecting axial motion of axial motion element 318 will be evident to those skilled in the art who have read the present patent application, and are within the scope of the present invention. For example, mechanical user control element 320 may comprise a knob that assumes three different rotational configuration (e.g., spatial positions) that cause axial motion element 318 to assume three different corresponding axial positions.

In the configurations of input module 156 described herein, the states of the flow regulator are generally effected by linear axial motion of catheter main body 210 with respect to housing 310. This linear motion may be triggered by the user's linearly moving mechanical user control element 320, or by the user's rotationally moving mechanical user control element 320, as described with reference to FIGS. 6A-B), in order to cause linear motion of the catheter main body. However, applications of the present invention are not limited to such linear motion. The same principles may be employed to activate a rotational motion of mechanical switching of fluid communication between the ports of housing 310 and the lumen inlets of the catheter main body.

Figure 7A:
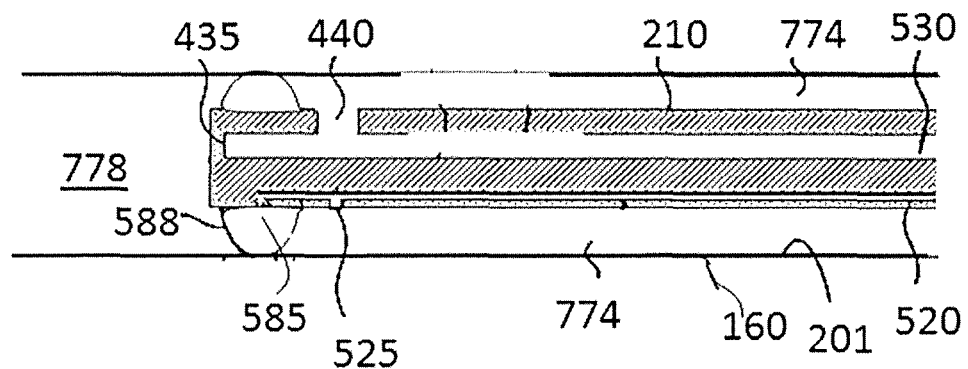
FIGS. 7A and 7B are schematic illustrations of a distal portion of a main body of the cleaning system of FIGS. 1A-C inserted into a ventilation tube, in accordance with an application of the present invention.
Figure 7B:
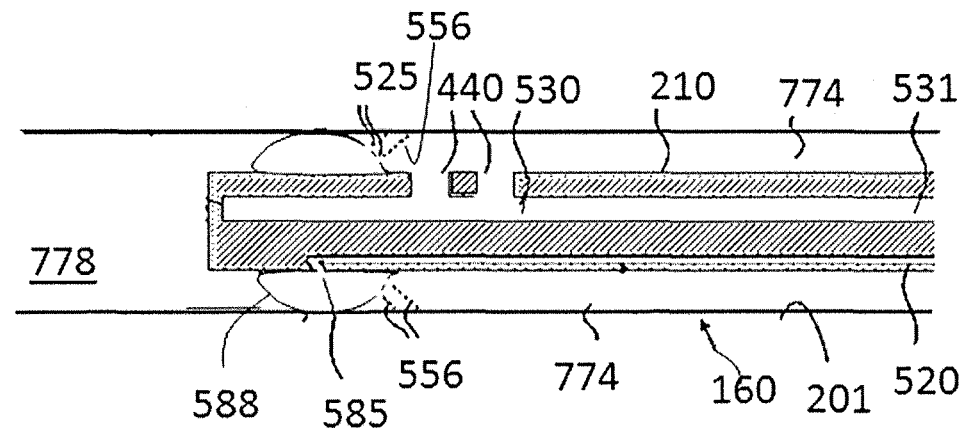

Reference is now made to FIGS. 7A and 7B, which are schematic illustrations of distal portion 212 of cleaning catheter 200 inserted into ventilation tube 160, in accordance with an application of the present invention. The configurations illustrated in FIGS. 7A and 7B may be used with any of the configurations of cleaning system 100 described herein, including with reference to FIGS. 1A-D, 3, 4A-C, 5A-C, 6A-B, 8 and 9A-C, 10 and 11A-C, 12 and 13A-B, 14 and 15A-B, 16A-C, 17A-C, 18A-C, 19A-C, 20, 21A-B and 22A-C, and 23 and 24A-C. In the configurations illustrated in FIGS. 7A and 7B, expandable element 588 comprises an inflatable element, and at least one of one or more fluid-delivery lumens 520 is in fluid communication with an interior of expandable element 588. Inflatable element 588 is inflated by fluid pressure provided from the same source as the fluid delivered to one or more fluid-delivery lumens 520, namely fluid source 602.

In the configurations shown in both FIGS. 7A and 7B, one or more fluid-delivery orifices 525 are in fluid communication with the interior of inflatable element 588. Inflatable element 588 is inflated by fluid communication with the at least one of one or more fluid-delivery lumens 520 via one or more inflation outlets 585 defined by distal portion 212 of cleaning catheter 200. Fluid is ejected from one or more fluid-delivery orifices 525 that are also in fluid communication with one or more fluid-delivery lumens 520.

In the configuration shown in FIG. 7A, a wall of main body 210 at distal portion 212 of cleaning catheter 200 is shaped so as to define fluid-delivery orifices 525. In the configuration shown in FIG. 7B, the wall of inflatable element 588 defines one or more fluid-delivery orifices 525, typically on a surface of inflatable element 588 that faces proximally. Fluid sprayed from these orifices is symbolically illustrated as fluid streams 556. Alternatively, a portion of fluid-delivery orifices 525 are defined by the wall of main body 210, and another portion of fluid-delivery orifices 525 are defined by the wall of inflatable element 588 (configuration not shown).

Generally, one or more suction lumens 530 facilitate fluid communication between its proximal suction inlet 531 and distal suction orifices 440, and one or more fluid-delivery lumens 520 facilitate fluid communication between its proximal suction inlet 531 and distal fluid delivery to fluid-delivery orifices 525. Inflation of inflatable element 588 (i.e., fluid communication to its inner surface) is facilitated either via a dedicated inflation lumen 580 or via one or more of fluid-delivery lumens 520.

Upon inflation of inflatable element 588 when the inflatable element is positioned within ventilation tube 160, the inflated inflatable element forms a sliding boundary which obstructs (i.e., significantly hinders) fluid flow to between: (a) a more proximal portion 774 of an interstitial region outside of main body 210 and within ventilation tube 160 and (b) locations 778 within the ventilation tube 160 that are distal to the slidable boundary formed and delineated by the inflatable element 588.

In some applications of the present invention, catheter main body 210 comprises at least two separate suction lumens: (a) at least a first suction lumen 530 which is in fluid communication with one or more distal suction orifices 440 proximal to expandable element 588, but no suction orifices located distal to the expandable element, and (b) at least a second suction lumen which is in fluid communication with one or more suction orifices located distal to the expandable element. Preferably, the second suction lumen is not in fluid communication with any distal suction orifices proximal to the expandable element.

Such dual suction lumen configuration has the advantage of enabling selective performance of suction either exclusively proximal to the expandable element, or exclusively distal to the expandable element, or both. Also, this configuration enables more gradual control of the suction forces applied distal and proximal to the expandable element. For example, in at least one operating state suction force delivered to the one or more suction orifices distal to the expandable element is weaker than 20% of the suction force applied through the largest orifice 440 proximal to the expandable element, and in at least one other operating state suction force delivered to the one or more suction orifices distal to the expandable element is stronger than 20% of the suction force applied through the largest orifice 440 proximal to the expandable element.

Reference is now made to FIG. 8, which is a schematic illustration of a portion of proximal portion 214 of main body 210, in accordance with an application of the present invention. FIG. 8 (and FIGS. 9A-C) illustrate configurations of proximal portion 214 of main body 210 appropriate for use with either of the configurations of distal portion 212 of cleaning catheter 200 described hereinabove with reference to FIGS. 7A and 7B. In these configuration, expandable element 588 is inflated via fluid communication to pressurized fluid in at least one of one or more fluid-delivery lumens 520, e.g., exactly one fluid-delivery lumen 520, which are in fluid communication with an interior of expandable element 588. There is thus no need to provide separate inflation lumen 580 to the expandable element (such as described hereinabove with reference to FIGS. 3 and 4A-C), because the expandable element is inflated via one or more inflation outlets 585 from the at least one of the one or more fluid-delivery lumens 520 itself. Alternatively, expandable element 588 is inflated via dedicated inflation lumen 580 which is in fluid communication directly with one or more fluid-delivery lumens 520, or with the same source 602 of pressurized fluid with which one or more fluid-delivery lumens 520 are in fluid communication (configuration not shown).

In the particular configuration shown in FIG. 8 (and FIGS. 9A-C), main body 210 is shaped so as to define at least two lumens: one or more fluid-delivery lumens 520 (e.g., exactly one fluid-delivery lumen 520), and one or more suction lumens 530 (e.g., exactly one suction lumen 530), and respective at least one proximal fluid-delivery inlet 521 (e.g., exactly one proximal fluid-delivery inlet 521), and at least one proximal suction inlet 531 (e.g., exactly one proximal suction inlet 531). In this particular configuration, main body 210 is not shaped so as to define inflation lumen 580 or inflation inlet 581, described hereinabove with reference to FIGS. 3 and 4A-C. In this particular configuration, expandable element 588 comprises an inflatable element 588, such as a balloon.

FIG. 8 shows one or more fluid-delivery lumens 520 and one or more suction lumens 530, which have been omitted from FIGS. 9A-B for clarity of illustration. For some applications, proximal suction inlet 531 is located proximal to proximal fluid-delivery inlet 521. For some applications, as shown, proximal suction inlet 531 is defined by a lateral wall of main body 210, while for other applications, proximal suction inlet 531 is defined by a proximal end of main body 210, such as shown in FIGS. 5B-C, 17A-C, and 18A-C.

Reference is made to FIGS. 9A-C, which are schematic illustrations of several states of a flow regulator 710 of input module 156, in accordance with an application of the present invention. Except as described as follows, input module 156 is configured as described hereinabove with reference to FIGS. 4A-C. Except as described as follows, flow regulator 710 is generally similar to flow regulator 700, described hereinabove with reference to FIGS. 4A-C. As mentioned above, in some applications input portion 216 of proximal portion of main body 210 is configured to be inserted into and axially slidable with respect to input module 156. Input module 156 has a plurality of ports for connection with various fluid sources, including at least suction source 601 and pressurized fluid source 602. In this configuration, input module 156 includes fluid port 827, which is coupleable in fluid communication with pressurized fluid source 602, and suction port 830, which is coupleable in fluid communication with suction source 601, but does not include inflation port 832, described hereinabove with reference to FIGS. 4A-C. In addition, inflation source 603 is not provided.

As mentioned above, input module 156 is configured to assume a plurality of activation states. Mechanical control unit 320 is typically configured to mechanically and non-electrically set the states of flow regulator 710. Input module 156 is configured to set the activation states enabling or blocking fluid communication between the various lumen inlets and the external fluid sources via respective ports. For some applications, transitions between states are effected by shifts in alignment of the lumen inlets with respect to various chambers of input module 156, which chambers are or are not in fluid communication with respective ports. The shifts in alignment are typically effected via axial motion of input portion 216 of catheter main body 210 within input module housing 310, along the longitudinal axes of input portion 216 and input module 156.

In this configuration, flow regulator 710 is configured to have three principal activation states, typically associated with three configurations (e.g., spatial positions) of mechanical user control element 320. In the configuration illustrated in FIGS. 9A-C, the three states are actuated by axial motion of proximal portion 214 of elongated main body 210 relative to input module housing 310:

- as shown in FIG. 9A, a first activation state, in which flow regulator 710 blocks fluid communication (a) between suction port 830 and proximal suction inlet 531, and thus one or more suction lumens 530 and (b) between fluid port 827 and proximal fluid-delivery inlet 521, and thus one or more fluid-delivery lumens 520; as a result, fluid communication is blocked to both fluid-delivery orifices 525 and the interior of inflatable element 588 (this configuration can be used with either the configuration described with reference to FIG. 7A or that described with reference to FIG. 7B). For some applications, this first activation state may be considered to be a base, default activation state, which optionally is set by an elastic return force element, such as described hereinbelow with reference to FIGS. 5B-C;
- as shown in FIG. 9B, a second activation state, in which flow regulator 710 effects suction fluid communication between suction port 830 and one or more suction lumens 530 via proximal suction inlet 531, and blocks flow of fluid between fluid port 827 and one or more fluid-delivery lumens 520; and
- as shown in FIG. 9C, a third activation state, in which flow regulator 710 effects both (a) suction fluid communication between suction port 830 and one or more suction lumens 530 via proximal suction inlet 531, and (b) fluid communication between fluid port 827 and one or more fluid-delivery lumens 520 via proximal fluid-delivery inlet 521; as a result, fluid communication is provided to both fluid-delivery orifices 525 and the interior of inflatable element 588.

As mentioned above, mechanical user control element 320 is configured to mechanically and non-electrically set the states of flow regulator 710. Typically, mechanical user control element 320 has at least first, second and third configurations (e.g., spatial positions), and, typically, is configured to transition between the first and the third configuration (e.g., spatial positions) via the second configuration (e.g., spatial position). For example, mechanical user control element 320 is shown in FIG. 9A in its first configuration (e.g., spatial position) (right-most position), in FIG. 9B in its second configuration (e.g., spatial position) (center position), and in FIG. 9C in its third configuration (e.g., spatial position) (left-most position). Input module 156 is configured such that:

- when user control element 320 is in the first configuration (e.g., spatial position), flow regulator 710 is in the first activation state, as described above;
- when user control element 320 is in the second configuration (e.g., spatial position), flow regulator 710 is in the second activation state, as described above; and
- when user control element 320 is in the third configuration (e.g., spatial position), flow regulator 710 is in the third activation state, as described above.

As mentioned, FIG. 9A shows flow regulator 710 in the first (blocked) state. Input portion 216 of main body 210 is encased, yet movable, within housing 310 of input module 156. Catheter main body 210 is slidable through a distal wall 314 of housing 310. Housing 310 is shaped so as to define suction port 830 and cleaning fluid port 827 (main body 210 does not define these ports).

As main body 210 moves within the inner compartment of housing 310, transverse sealing separators 341, 342, 343, and 344 delineate distinct chambers within the housing. When flow regulator 710 is in the first activation state, as shown in FIG. 9A, separators 342 and 343 and the outer surface of elongated main body 210 delineate first chamber 350 around proximal fluid-delivery inlet 521, and thereby block direct fluid communication within housing 310 between proximal fluid-delivery inlet 521 and proximal suction inlet 531. The separators are attached to the main body and snugly pressed against the inner surface of housing 310, so that the insulated chamber around proximal fluid-delivery inlet 521 is maintained even as the main body slides a certain distance along the longitudinal axis thereof with respect the housing.

Also as shown in FIG. 9A, in the first activation state, elongated main body 210 is positioned in its closest position to a proximal end 360 of housing 310, proximal-most separator 344 creates a seal which prevents direct fluid communication between suction port 830 of housing 310 and proximal suction inlet 531 of elongated main body 210. In this base position, cleaning fluid flow is blocked within a second sealed chamber 352 delineated by separators 341 and 342 and the outer surface of elongated main body 210.

When flow regulator 710 is in the second activation state, as shown in FIG. 9B, fluid communication is established between suction port 830 of housing 310 and proximal suction inlet 531 and into one or more suction lumens 530 in elongated main body 210, yet cleaning fluid flow remains blocked within second sealed chamber 352 delineated by separators 341 and 342 and the outer surface of elongated main body 210. This activation is achieved by sliding elongated main body 210 distally along the axial direction by a limited distance such that separator 342 does not yet cross into the space of cleaning fluid port 827. Typically, this sliding motion is induced by distally pushing on mechanical user control element 320, which is coupled to elongated main body 210 and passes through a slit 312 in housing 310 which allows axial motion of mechanical user control element 320.

When flow regulator 710 is in the third activation state, as shown in FIG. 9C, fluid communication is established in first chamber 350 between cleaning fluid port 827 of housing 310 and proximal fluid-delivery inlet 521 and one or more fluid-delivery lumens 520 in elongated main body 210. Suction port 830 of housing 310 remains in fluid communication with proximal suction inlet 531 and into one or more suction lumens 530 in elongated main body 210. Therefore, in this third activation state, flow regulator 710 effects both (a) cleaning fluid flow into one or more fluid-delivery lumens 520 and (b) suction in one or more suction lumens 530 of elongated main body 210. This activation is achieved by sliding elongated main body 210 more distally along the axial direction by a limited distance such that separator 342 crosses into or passes across the space of cleaning fluid port 827. Typically, the sliding motion is induced by distally pushing on mechanical user control element 320, which is coupled to elongated main body 210 and passes through slit 312 in housing 310.

Thus, three activation states can be actuated, typically associated with three configurations (e.g., spatial positions) of mechanical user control element 320. In the configuration illustrated in FIGS. 9A-C, the three states are actuated by axial motion of input portion 216 of elongated main body 210 relative to input module housing 310:

the first activation state, in which suction flow and cleaning fluid flow is blocked;

the second activation state, in which suction flow is enabled between one or more suction lumens 530 and suction port 830 via proximal suction inlet 531 into one or more suction lumens 530, but cleaning fluid flow into one or more fluid-delivery lumens 520 remains blocked; and the third activation state, in which suction flow is enabled both between one or more suction lumens 530 and suction port 830 via proximal suction inlet 531 into one or more suction lumens 530, and cleaning fluid flow into one or more fluid-delivery lumens 520 from fluid port 827 of housing 310 via proximal fluid-delivery inlet 521, thereby both providing fluid to fluid-delivery orifices 525 and the interior of inflatable element 588, so as to inflate the inflatable element.

Operational safely is inherent because there is no activation state in which cleaning fluid flow is enabled without suction also being activated.

For some applications, expandable element 588 is emptied by suction via the same suction source 601 which is connected to suction port 830. This can be enabled, for example, by establishing fluid communication between the lumen which is in fluid communication with expandable element (at least one of one or more fluid-delivery lumens 520 or inflation lumen 580). For some applications, expandable element 588 can be both inflated via pressurized delivery fluid in communication with one or more fluid-delivery lumens 520 and be deflated by suction provided by the same source 601 connected to one or more suction lumens 530. Examples of such configurations are described hereinbelow with reference to FIGS. 10 and 11A-C, FIGS. 12A-B and 13A-B, FIGS. 14 and 15A-B, and FIGS. 16A-C.

Figure 10:
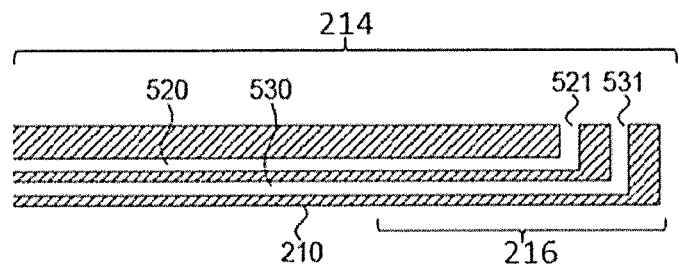
FIG. 10 is a schematic illustration of a portion of a proximal portion of a main body of the cleaning system of FIGS. 1A-C, in accordance with an application of the present invention.

Reference is now made to FIG. 10, which is a schematic illustration of a portion of proximal portion 214 of main body 210, in accordance with an application of the present invention. FIG. 10 shows one or more fluid-delivery lumens 520 and one or more suction lumens 530, which have been omitted from FIGS. 11A-C for clarity of illustration. FIG. 10 (and FIGS. 11A-C) illustrate configurations of proximal portion 214 of main body 210 appropriate for use with either of the configurations of distal portion 212 of cleaning catheter 200 described hereinabove with reference to FIGS. 7A and 7B. In these configuration, expandable element 588 is inflated via fluid communication to pressurized fluid in at least one of one or more fluid-delivery lumens 520, e.g., exactly one fluid-delivery lumen 520, which are in fluid communication with an interior of expandable element 588. There is thus no need to provide separate inflation lumen 580 to the expandable element, because the expandable element is inflated via one or more inflation outlets 585 from the at least one of the one or more fluid-delivery lumens 520 itself. Alternatively, expandable element 588 is inflated via dedicated inflation lumen 580 which is in fluid communication directly with one or more fluid-delivery lumens 520, or with the same source 602 of pressurized fluid with which one or more fluid-delivery lumens 520 are in fluid communication (configuration not shown). The configuration shown in FIG. 10 is the same as that shown in FIG. 8, described hereinabove.

Figure 11A:
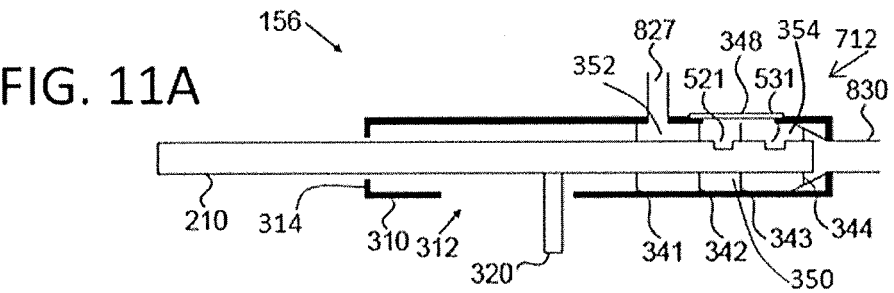
FIGS. 11A-C are schematic illustrations of several states of a flow regulator of a input module of the cleaning system of FIGS. 1A-C, in accordance with an application of the present invention.
Figure 11B:
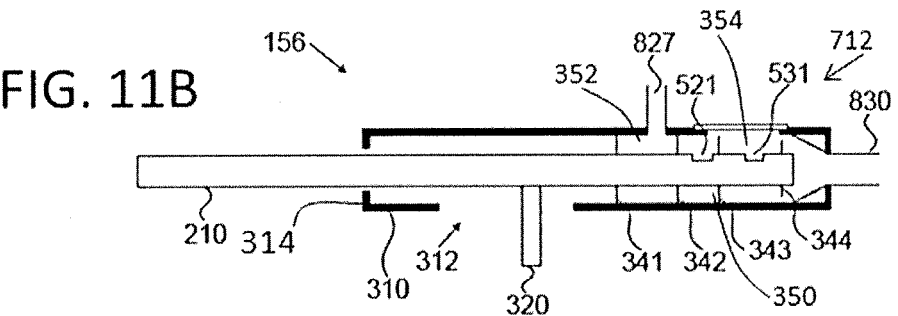
Figure 11C:
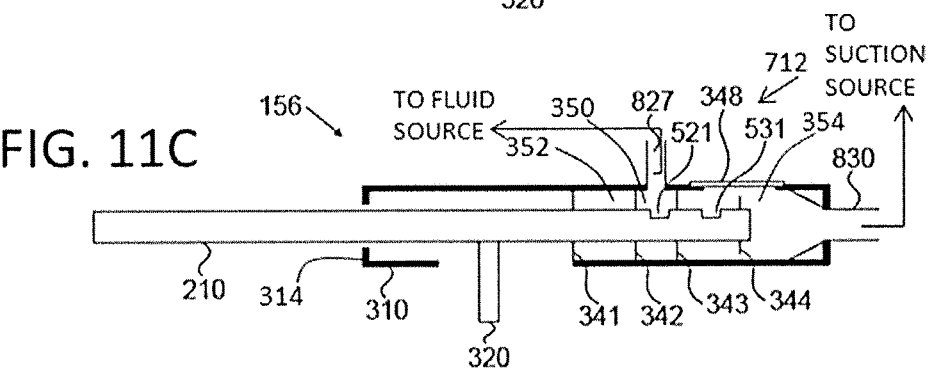

Reference is made to FIGS. 11A-C, which are schematic illustrations of several states of a flow regulator 712 of input module 156, in accordance with an application of the present invention. Except as described as follows, input module 156 is configured as described hereinabove with reference to FIGS. 4A-C and 9A-C. Except as described as follows, flow regulator 712 is generally similar to flow regulator 710, described hereinabove with reference to FIGS. 9A-C. As mentioned above, in some applications input portion 216 of proximal portion of main body 210 is configured to be inserted into and axially slidable with respect to input module 156. Input module 156 has a plurality of ports for connection with various fluid sources, including at least suction source 601 and pressurized fluid source 602. In this configuration, input module 156 includes fluid port 827, which is coupleable in fluid communication with pressurized fluid source 602, and suction port 830, which is coupleable in fluid communication with suction source 601, but does not include inflation port 832, described hereinabove with reference to FIGS. 4A-C. In addition, inflation source 603 is not provided.

As mentioned above, input module 156 is configured to assume a plurality of activation states. Mechanical control unit 320 is typically configured to mechanically and non-electrically set the states of flow regulator 712. Input module 156 is configured to set the activation states enabling or blocking fluid communication between the various lumen inlets and the external fluid sources via respective ports. For some applications, transitions between states are effected by shifts in alignment of the lumen inlets with respect to various chambers of input module 156, which chambers are or are not in fluid communication with respective ports. The shifts in alignment are typically effected via axial motion of input portion 216 of catheter main body 210 within input module housing 310, along the longitudinal axes of input portion 216 and input module 156.

In this configuration, flow regulator 712 is configured to have three principal activation states, typically associated with three configurations (e.g., spatial positions) of mechanical user control element 320. In the configuration illustrated in FIGS. 11A-C, the three states are actuated by axial motion of proximal portion 214 of elongated main body 210 relative to input module housing 310:

as shown in FIG. 11A, a first activation state, in which flow regulator 712 blocks fluid communication (a) between suction port 830 and proximal suction inlet 531, and thus one or more suction lumens 530 and (b) between fluid port 827 and proximal fluid-delivery inlet 521, and thus one or more fluid-delivery lumens 520; as a result, fluid communication is blocked to both fluid-delivery orifices 525 and the interior of inflatable element 588 (this configuration can be used with either the configuration described with reference to FIG. 7A or that described with reference to FIG. 7B). For some applications, this first activation state may be considered to be a base, default activation state, which optionally is set by an elastic return force element, such as described hereinbelow with reference to FIGS. 5B-C;

as shown in FIG. 11B, a second activation state, in which flow regulator 712 (a) effects suction fluid communication between suction port 830 and one or more suction lumens 530 via proximal suction inlet 531, (b) effects suction fluid communication between suction port 830 and one or more fluid-delivery lumens 520 via proximal fluid-delivery inlet 521 (thereby deflating inflatable element 588), and (c) blocks flow of fluid between fluid port 827 and one or more fluid-delivery lumens 520. In this second activation state, flow regulator typically does not effect the fluid communication between suction source 601 and distal orifices 440; and as shown in FIG. 11C, a third activation state, in which flow regulator 712 effects both (a) suction fluid communication between suction port 830 and one or more suction lumens 530 via proximal suction inlet 531, and (b) fluid communication between fluid port 827 and one or more fluid-delivery lumens 520 via proximal fluid-delivery inlet 521; as a result, fluid communication is provided to both fluid-delivery orifices 525 and the interior of inflatable element 588, thereby inflating the inflatable element. (In this third activation state, flow regulator 712 does not effect the fluid communication between suction source 601 and the interior of inflatable element 588.)

As mentioned above, mechanical user control element 320 is configured to mechanically and non-electrically set the states of flow regulator 712. Typically, mechanical user control element 320 has at least first, second and third configurations (e.g., spatial positions), and, typically, is configured to transition between the first and the third configuration (e.g., spatial positions) via the second configuration (e.g., spatial position). For example, mechanical user control element 320 is shown in FIG. 11A in its first configuration (e.g., spatial position) (right-most position), in FIG. 11B in its second configuration (e.g., spatial position) (center position), and in FIG. 11C in its third configuration (e.g., spatial position) (left-most position). Input module 156 is configured such that:

when user control element 320 is in the first configuration (e.g., spatial position), flow regulator 712 is in the first activation state, as described above;

when user control element 320 is in the second configuration (e.g., spatial position), flow regulator 712 is in the second activation state, as described above; and when user control element 320 is in the third configuration (e.g., spatial position), flow regulator 712 is in the third activation state, as described above.

As mentioned, FIG. 11A shows flow regulator 712 in the first (blocked) state. Input portion 216 of main body 210 is encased, yet movable, within housing 310 of input module 156. Catheter main body 210 is slidable through a distal wall 314 of housing 310. Housing 310 is shaped so as to define suction port 830 and cleaning fluid port 827 (main body 210 does not define these ports).

As main body 210 moves within the inner compartment of housing 310, transverse sealing separators 341, 342, 343, and 344 delineate distinct chambers within the housing. When flow regulator 712 is in the first activation state, as shown in FIG. 11A, separators 342 and 343 and the outer surface of elongated main body 210 delineate first chamber 350 around proximal fluid-delivery inlet 521, and thereby block direct fluid communication within housing 310 between proximal fluid-delivery inlet 521 and proximal suction inlet 531. The separators are attached to the main body and snugly pressed against the inner surface of housing 310, so that the insulated chamber around proximal fluid-delivery inlet 521 is maintained even as the main body slides a certain distance along the longitudinal axis thereof with respect the housing.

However, the insulating capability of separator 343 between proximal fluid-delivery inlet 521 and proximal suction inlet 531 also depends on the full engagement of the separator with the inner wall of housing 310. A widening 348 of the encasing inner wall of housing 310, shown in FIGS. 11A-C, creates a path of fluid communication between proximal fluid-delivery inlet 521 and proximal suction inlet 531 around the separator 343 edge, i.e., between first chamber 350 and a third chamber 354 defined by separators 343 and 344 and the outer surface of elongated main body 210.

Also as shown in FIG. 11A, in the first activation state, elongated main body 210 is positioned in its closest position to a proximal end 360 of housing 310, proximal-most separator 344 creates a seal which prevents direct fluid communication between suction port 830 of housing 310 and proximal suction inlet 531 of elongated main body 210. In this base position, cleaning fluid flow is blocked within a second sealed chamber 352 delineated by separators 341 and 342 and the outer surface of elongated main body 210.

When flow regulator 712 is in the second activation state, as shown in FIG. 11B, fluid communication is established between suction port 830 of housing 310 and proximal suction inlet 531 and into one or more suction lumens 530 in elongated main body 210, yet cleaning fluid flow remains blocked within second sealed chamber 352 delineated by separators 341 and 342 and the outer surface of elongated main body 210. This activation is achieved by sliding elongated main body 210 distally along the axial direction by a limited distance such that separator 342 does not yet cross into the space of cleaning fluid port 827. Typically, this sliding motion is induced by distally pushing on mechanical user control element 320, which is coupled to elongated main body 210 and passes through a slit 312 in housing 310 which allows axial motion of mechanical user control element 320.

In addition, in this second activation state, fluid communication is established between proximal fluid-delivery inlet 521 and proximal suction inlet 531 (e.g., around the outermost edge of separator 343 via widening 348 in the wall of housing 310). Thus, in the second activation state, the suction force acts both on one or more suction lumens 530 and on expandable element 588 (e.g., communicated via one or more fluid-delivery lumens 520).

When flow regulator 712 is in the third activation state, as shown in FIG. 11C, fluid communication is established in first chamber 350 between cleaning fluid port 827 of housing 310 and proximal fluid-delivery inlet 521 and one or more fluid-delivery lumens 520 in elongated main body 210. Suction port 830 of housing 310 remains in fluid communication with proximal suction inlet 531 and into one or more suction lumens 530 in elongated main body 210. Therefore, in this third activation state, flow regulator 712 effects both (a) cleaning fluid flow into one or more fluid-delivery lumens 520 and (b) suction in one or more suction lumens 530 of elongated main body 210. This activation is achieved by sliding elongated main body 210 more distally along the axial direction by a limited distance such that separator 342 crosses into or passes across the space of cleaning fluid port 827. Typically, the sliding motion is induced by distally pushing on mechanical user control element 320, which is coupled to elongated main body 210 and passes through slit 312 in housing 310.

In addition, in this third activation state, the path of fluid communication between proximal fluid-delivery inlet 521 and proximal suction inlet 531 is blocked (e.g., because full engagement of separator 343 with the bounding wall of encasing housing 310 is established, because separator 343 is no longer axially aligned with widening 348). Thus, in the third activation state, suction force is blocked from expandable element 588 and acts only on one or more suction lumens 530. Additional arrangements for achieving fluid communication between first and third chambers 350 and 354 in the second activation state but not the third activation state will be evident to those skilled in the art who have read the present patent application, and are within the scope of the present invention.

Thus, three activation states can be actuated, typically associated with three configurations (e.g., spatial positions) of mechanical user control element 320. In the configuration illustrated in FIGS. 11A-C, the three states are actuated by axial motion of input portion 216 of elongated main body 210 relative to input module housing 310:

the first activation state, in which suction flow and cleaning fluid flow is blocked;

the second activation state, in which suction flow is enabled between one or more suction lumens 530 and suction port 830 via proximal suction inlet 531 into one or more suction lumens 530, and suction flow is also enabled between suction port 830 and the interior of inflatable element 588 via one or more fluid-delivery lumens 520 (thereby deflating the inflatable element), but cleaning fluid flow into one or more fluid-delivery lumens 520 remains blocked; and the third activation state, in which suction flow is enabled both between one or more suction lumens 530 and suction port 830 via proximal suction inlet 531 into one or more suction lumens 530, and cleaning fluid flow into one or more fluid-delivery lumens 520 from fluid port 827 of housing 310 via proximal fluid-delivery inlet 521, thereby both providing fluid to fluid-delivery orifices 525 and the interior of inflatable element 588, so as to inflate the inflatable element.

For some applications:

flow regulator 712, when in the second activation state, effects fluid communication between suction source 601 and an interior of the inflatable element 588 via at least one of one or more fluid-delivery lumens 520, thereby deflating inflatable element 588, and flow regulator 712, when in the third activation state, effects fluid communication between suction source 601 and distal suction orifices 440 via one or more suction lumens 530, and does not effect the fluid communication between suction source 601 and the interior of inflatable element 588.

Operational safely is inherent because there is no activation state in which cleaning fluid flow is enabled without suction also being activated.

Figure 12:
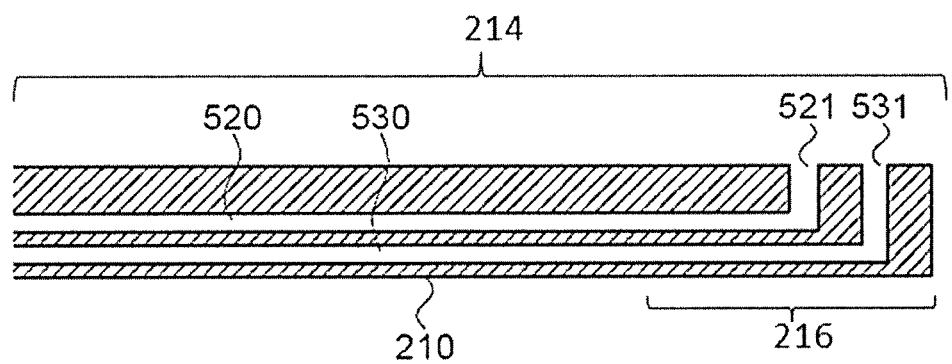
FIG. 12 is a schematic illustration of a portion of a proximal portion of a main body of the cleaning system of FIGS. 1A-C, in accordance with an application of the present invention.

Reference is now made to FIG. 12, which is a schematic illustration of a portion of proximal portion 214 of main body 210, in accordance with an application of the present invention. FIG. 12 shows one or more fluid-delivery lumens 520 and one or more suction lumens 530, which have been omitted from FIGS. 13A-B for clarity of illustration. FIG. 12 (and FIGS. 13A-B) illustrate configurations of proximal portion 214 of main body 210 appropriate for use with either of the configurations of distal portion 212 of cleaning catheter 200 described hereinabove with reference to FIGS. 7A and 7B. In these configurations, expandable element 588 is inflated via fluid communication to pressurized fluid in at least one of one or more fluid-delivery lumens 520, e.g., exactly one fluid-delivery lumen 520, which are in fluid communication with an interior of expandable element 588. There is thus no need to provide separate inflation lumen 580 to the expandable element (such as described hereinabove with reference to FIGS. 3 and 4A-C), because the expandable element is inflated via one or more inflation outlets 585 from the at least one of the one or more fluid-delivery lumens 520 itself. Alternatively, expandable element 588 is inflated via dedicated inflation lumen 580 which is in fluid communication directly with one or more fluid-delivery lumens 520, or with the same source 602 of pressurized fluid with which one or more fluid-delivery lumens 520 are in fluid communication (configuration not shown). The configuration shown in FIG. 12 is the same as that shown in FIGS. 8 and 10, described hereinabove.

Figure 13A:
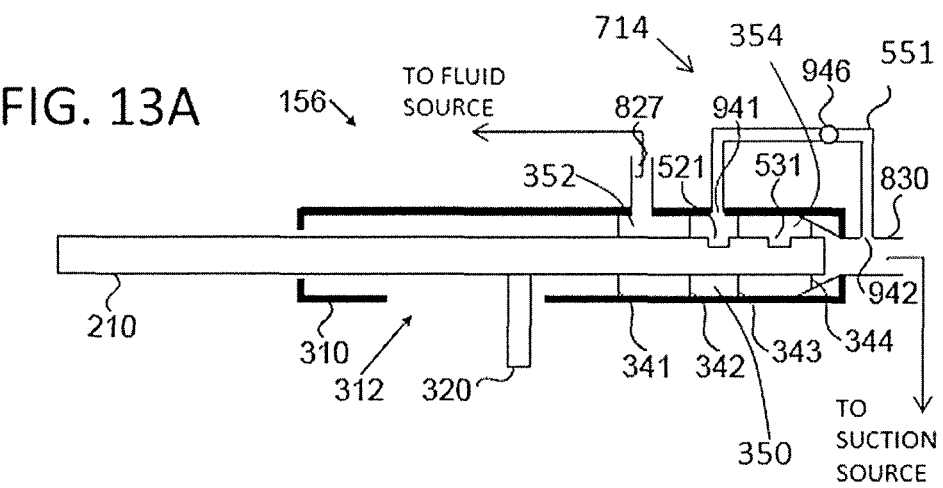
FIGS. 13A-B are schematic illustrations of several states of a flow regulator of a input module of the cleaning system of FIGS. 1A-C, in accordance with an application of the present invention.
Figure 13B:
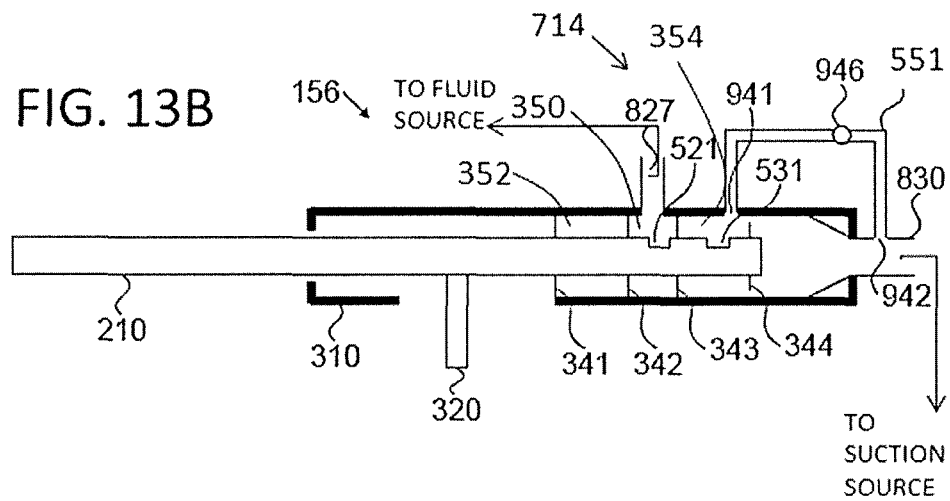

Reference is made to FIGS. 13A-B, which are schematic illustrations of several states of a flow regulator 714 of input module 156, in accordance with an application of the present invention. Except as described as follows, input module 156 is configured as described hereinabove with reference to FIGS. 9A-C and 11A-C. Except as described as follows, flow regulator 714 is generally similar to flow regulator 712, described hereinabove with reference to FIGS. 11A-C. As mentioned above, in some applications input portion 216 of proximal portion of main body 210 is configured to be inserted into and axially slidable with respect to input module 156. Input module 156 has a plurality of ports for connection with various fluid sources, including at least suction source 601 and pressurized fluid source 602. In this configuration, input module 156 includes fluid port 827, which is coupleable in fluid communication with pressurized fluid source 602, and suction port 830, which is coupleable in fluid communication with suction source 601, but does not include inflation port 832, described hereinabove with reference to FIGS. 4A-C. In addition, inflation source 603 is not provided.

As mentioned above, input module 156 is configured to assume a plurality of activation states. Mechanical control unit 320, together with a valve 946 if provided, are typically configured to mechanically and non-electrically set the states of flow regulator 714. Input module 156 is configured to set the activation states enabling or blocking fluid communication between the various lumen inlets and the external fluid sources via respective ports. For some applications, transitions between states are effected in part by shifts in alignment of the lumen inlets with respect to various chambers of input module 156, which chambers are or are not in fluid communication with respective ports. The shifts in alignment are typically effected via axial motion of input portion 216 of catheter main body 210 within input module housing 310, along the longitudinal axes of input portion 216 and input module 156.

In addition, flow regulator 714 optionally comprises a fluid communication suction channel 551, having distal and proximal inlets 941 and 942. For some applications, fluid communication suction channel 551 is disposed external to housing 310; for example, channel 551 may be provided by a separate tube, such as shown in FIGS. 13A-B. Suction channel proximal inlet 942 is in fluid communication with suction source 601; for example, proximal inlet 942 may be in fluid communication with suction port 830, such as shown in FIG. 13A. Suction channel distal inlet 941 is coupled in fluid communication with housing 310 such that, when flow regulator 714 is in the first activation state shown in FIG. 13A, distal inlet 941 is in fluid communication with an interior of expandable element 588, e.g., via fluid-delivery inlet 521 and at least one of one or more fluid-delivery lumens 520, as shown in FIG. 13A, or via an inflation inlet 581 and inflation lumen 580 in the alternative configuration described hereinbelow with reference to FIG. 15A. As a result, suction can be delivered to expandable element 588 via the at least one of the one or more fluid-delivery lumens 520 or inflation lumen 580, even at a time when no suction is delivered to one or more suction lumens 530, in the first position shown FIG. 13A.

For some applications, flow regulator 714 further comprises a valve 946, which is in fluid communication with suction port 830, and which is arranged to regulate fluid flow through suction channel 551. Valve 946 is switchable between closed and open fluid communication states between distal inlet 941 and proximal inlet 942 of suction channel 551.

In this configuration, flow regulator 714 enables independent control over the suction communication to expandable element 588 for deflation thereof. Flow regulator 714 is configured to have up to four principal activation states, typically associated with three configurations (e.g., spatial positions) of mechanical user control element 320. In the configuration illustrated in FIGS. 13A-B, the states are actuated by axial motion of proximal portion 214 of elongated main body 210 relative to input module housing 310 and, optionally by setting the state of valve 946:

as shown in FIG. 13A, a primary first activation state, in which valve 946 is in the open state. In this state flow regulator 714 blocks fluid communication (a) between suction port 830 and proximal suction inlet 531, and thus one or more suction lumens 530; as a result, fluid communication is blocked to fluid-delivery orifices 525 (this configuration can be used with either the configuration described with reference to FIG. 7A or that described with reference to FIG. 7B). In addition, in this state flow regulator 714 effects suction fluid communication between suction port 830 and the interior of inflatable element 588 via (a) suction channel 551, (b) proximal fluid-delivery inlet 521, and (c) one or more fluid-delivery lumens 520, thereby deflating inflatable element 588. For some applications, this primary first activation state may be considered to be a primary base, default activation state, which optionally is set in part by an elastic return force element, such as described hereinbelow with reference to FIGS. 5B-C;

also as shown in FIG. 13A, a secondary activation state, in which valve 946 is in the open state, and proximal portion 214 of elongated main body 210 is in the same relative axial position with respect to input module housing 310 as in the primary first activation state. In this secondary activation state, flow regulator 714 blocks fluid communication (a) between suction port 830 and proximal suction inlet 531, and thus one or more suction lumens 530 and (b) between fluid port 827 and proximal fluid-delivery inlet 521 (because valve 946 blocks suction channel 551), and thus one or more fluid-delivery lumens 520; as a result, fluid communication is blocked to both fluid-delivery orifices 525 and the interior of inflatable element 588. For some applications, this secondary first activation state may be considered to be a secondary base, default activation state;

a second activation state, in which flow regulator 714 effects suction fluid communication between suction port 830 and one or more suction lumens 530 via proximal suction inlet 531, and blocks flow of fluid between fluid port 827 and one or more fluid-delivery lumens 520. This second activation state is not shown in FIGS. 13A-B, but is typically identical to the state show in FIG. 9B, except for the difference in flow regulator 714 described above. In this state, suction channel 551 typically has no effect on the state of fluid flow; and as shown in FIG. 13C, a third activation state, in which flow regulator 714 effects both (a) suction fluid communication between suction port 830 and one or more suction lumens 530 via proximal suction inlet 531, and (b) fluid communication between fluid port 827 and one or more fluid-delivery lumens 520 via proximal fluid-delivery inlet 521; as a result, fluid communication is provided to both fluid-delivery orifices 525 and the interior of inflatable element 588, thereby inflating the inflatable element. (In this third activation state, flow regulator 714 does not effect the fluid communication between suction source 601 and the interior of inflatable element 588.)

As mentioned above, mechanical user control element 320 and valve 946 if provided are configured to mechanically and non-electrically set the states of flow regulator 714. Typically, mechanical user control element 320 has at least first, second and third configurations (e.g., spatial positions), and, typically, is configured to transition between the first and the third configuration (e.g., spatial positions) via the second configuration (e.g., spatial position). For example, mechanical user control element 320 is shown in FIG. 13A in its first configuration (e.g., spatial position) (right-most position) and in FIG. 13C in its third configuration (e.g., spatial position) (left-most position). Input module 156 is configured such that:

when user control element 320 is in the first configuration (e.g., spatial position), flow regulator 714 is in the primary or second first activation state (depending on the state of valve 946), as described above;

when user control element 320 is in the second configuration (e.g., spatial position), flow regulator 714 is in the second activation state, as described above; and when user control element 320 is in the third configuration (e.g., spatial position), flow regulator 714 is in the third activation state, as described above.

Thus, four activation states can be actuated (three mandatory and one optional), typically associated with three configurations (e.g., spatial positions) of mechanical user control element 320 and, optionally, two states of valve 946. In the configuration illustrated in FIGS. 13A-B, the four states are actuated by axial motion of input portion 216 of elongated main body 210 relative to input module housing 310, as well as by the state of valve 946:

the primary first activation state, in which suction flow to one or more suction lumens 530 and cleaning fluid flow is blocked, and inflatable element 588 is deflated by active suction (via open suction channel 551 flow);

the secondary first activation state, in which suction flow to one or more suction lumens 530 is blocked and cleaning fluid flow is blocked, and also suction flow to inflatable element 588 is blocked (because valve 946 blocks flow through suction channel 551);

the second activation state, in which suction flow is enabled between one or more suction lumens 530 and suction port 830 via proximal suction inlet 531 into one or more suction lumens 530, but cleaning fluid flow into one or more fluid-delivery lumens 520 remains blocked; and the third activation state, in which suction flow is enabled both between one or more suction lumens 530 and suction port 830 via proximal suction inlet 531 into one or more suction lumens 530, and cleaning fluid flow into one or more fluid-delivery lumens 520 from fluid port 827 of housing 310 via proximal fluid-delivery inlet 521, thereby both providing fluid to fluid-delivery orifices 525 and the interior of inflatable element 588, so as to inflate the inflatable element.

Operational safely is inherent because there is no activation state in which cleaning fluid flow is enabled without suction also being activated.

Figure 14:
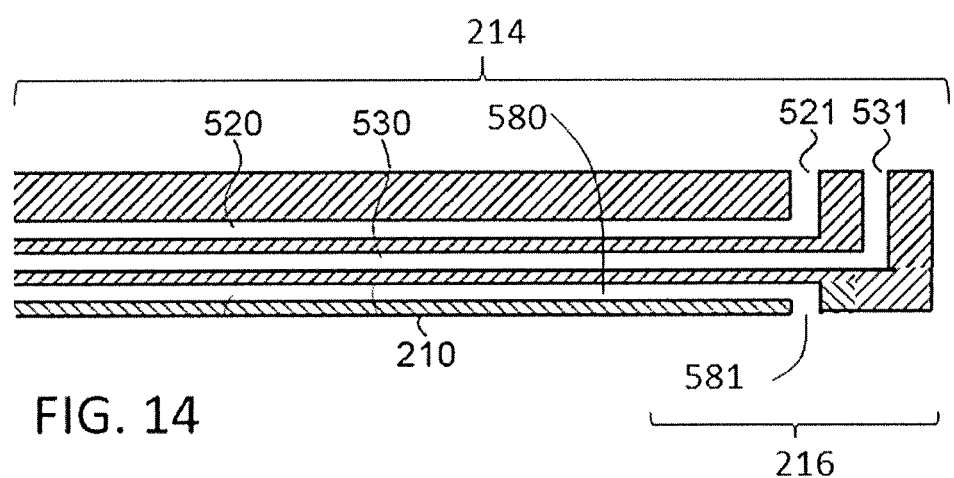
FIG. 14 is a schematic illustration of a portion of a proximal portion of a main body of the cleaning system of FIGS. 1A-C, in accordance with an application of the present invention.
Figure 15A:
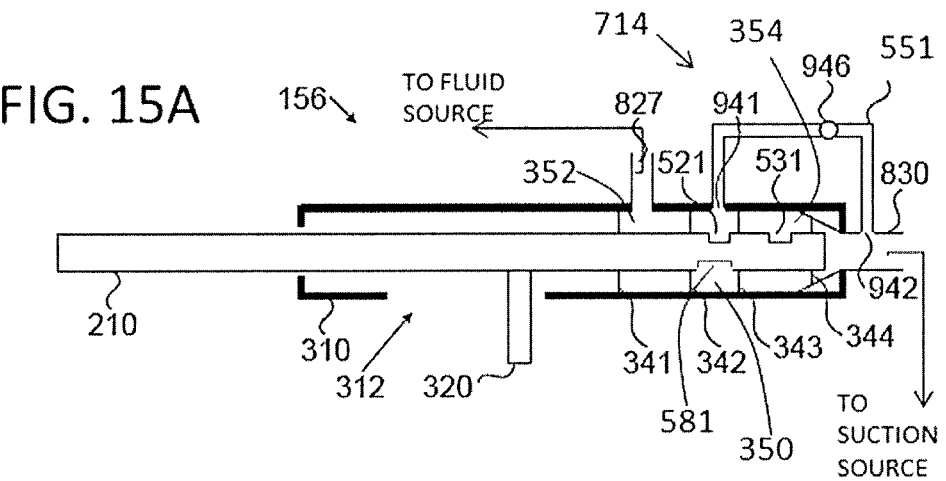
FIGS. 15A-B are schematic illustrations of several states of a flow regulator of a input module of the cleaning system of FIGS. 1A-C, in accordance with an application of the present invention.
Figure 15B:
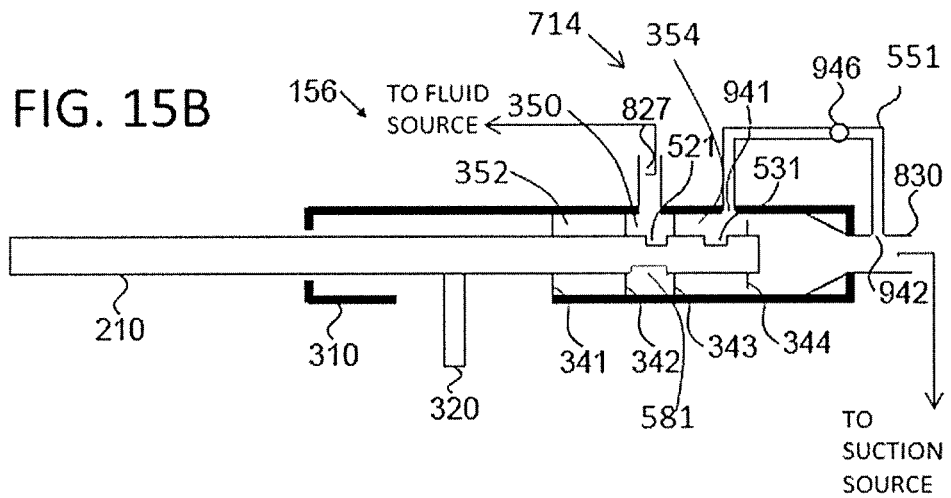

Reference is now made to FIG. 14, which is a schematic illustration of a portion of proximal portion 214 of main body 210, in accordance with an application of the present invention, and FIGS. 15A-B, which are schematic illustrations of several states of a flow regulator 714 of input module 156, in accordance with an application of the present invention. Except as described hereinbelow, the configuration shown in FIGS. 14 and 15A-B is identical to the configuration described hereinabove with reference to FIGS. 12 and 13A-B, and achieves the same activation states.

In this configuration, catheter main body 210, in addition to one or more fluid-delivery lumens 520 and one or more suction lumens 530, comprises independent inflation lumen 580 in fluid communication with an interior of expandable element 588. In order to achieve the same dual activation as in the configuration of FIGS. 12 and 13A-B, input portion 216 of elongated main body 210 is shaped so as define inflation inlet 581 to inflation lumen 580 at about the same axial position along main body 210 as proximal fluid-delivery inlet 521 to one or more fluid-delivery lumens 520. As a result, inflation lumen 580 and one or more fluid-delivery lumens 520 are commonly in fluid communication with one another (e.g., in the flow regulator), and therefore receive fluid delivery or suction actions essentially simultaneously. In other words, the fluid communication to expandable element 588 can be provided either via dedicated lumen 580, as shown in FIGS. 14 and 15A-B, or via one or more shared fluid-delivery lumens 520, as shown in FIGS. 12 and 13A-B. One difference between the configuration of FIGS. 12 and 13A-B and the configuration of FIGS. 14 and 15A-B is that, in the configuration of FIGS. 12 and 13A-B, unlike in the configuration of FIGS. 14 and 15A-B, the interior of expandable element 588 is in fluid communication with fluid-delivery orifices 525.

For some applications (although this feature is typically not implemented), if the suction flow out of the expandable element is relatively weak compared with the fluid flow into the expandable element, it may be possible to maintain the expandable element inflated even if both pressurized fluid and weak suction is simultaneously communicated to it.

Figure 16A:
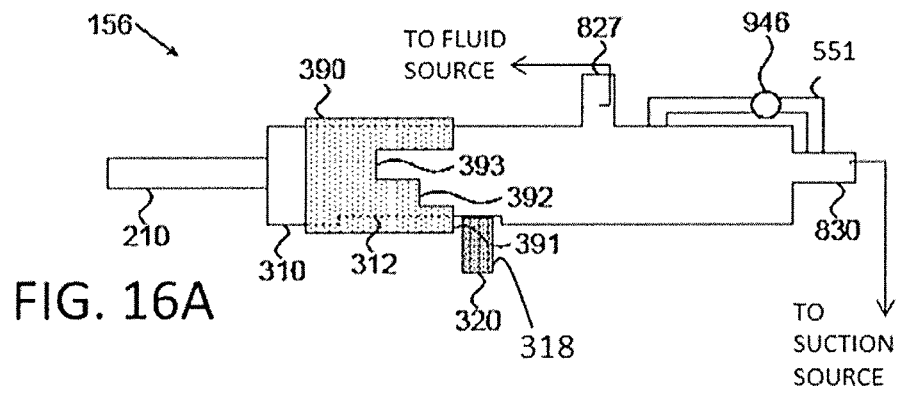
FIGS. 16A-C are schematic illustrations of a configuration of an input module of the cleaning system of FIGS. 1A-C comprising a state protective selector, in accordance with an application of the present invention.
Figure 16B:
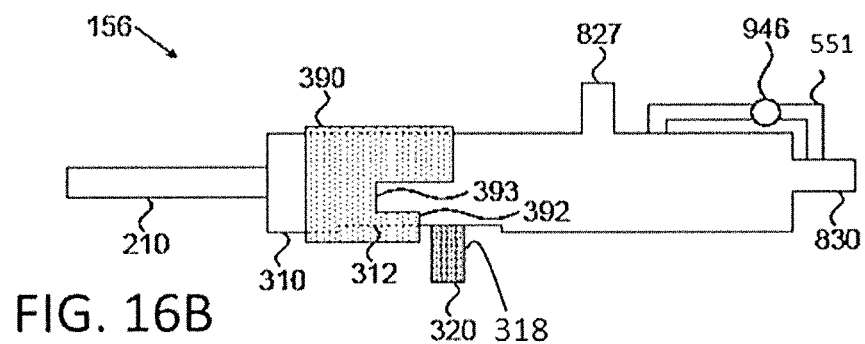
Figure 16C:
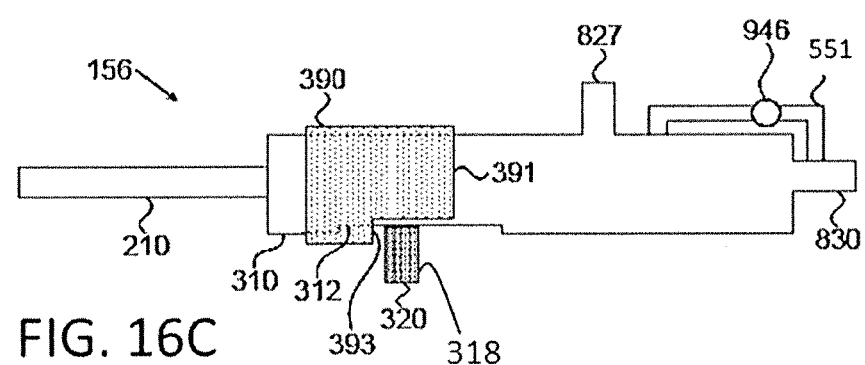

Reference is now made to FIGS. 16A-C, which are schematic illustrations of a configuration of input module 156 comprising a state protective selector 390, in accordance with an application of the present invention. Although the configuration of input module 156 shown generally corresponds to the configurations described hereinabove with reference to FIGS. 12 and 13A-B and FIGS. 14 and 15A-B, state protective selector 390 may also be provided for the other configurations described herein.

State protective selector 390 provides a plurality of protective states, each of which prevents certain movements of mechanical user control element 320, while allowing other movements of element 320. In a protective selector first state 391, shown in FIG. 16A, movement of mechanical user control element 320 is limited such that it is locked in the first configuration (e.g., spatial position), corresponding to the first activation state of the flow regulator. In a protective selector second state 392, shown in FIG. 16B, movement of mechanical user control element 320 is limited such that it can move only between the first configuration (e.g., spatial position) and the second configuration (e.g., spatial position), corresponding to the second activation state. In a protective selector third state 393, movement of mechanical user control element 320 is enabled to reach all three of the first, second, and third configuration (e.g., spatial positions), corresponding to all three activation states, respectively.

Therefore, as illustrated in FIGS. 16A-C, at least activation states can be actuated (three mandatory, and one optional), typically associated with three configuration (e.g., spatial positions) of mechanical user control element 320, and an optional independent control valve state of suction flow to the expandable element. In the configuration illustrated in FIGS. 16A-C, the activation states are actuated by axial motion of elongated main body 210 relative to input module housing 310, as well as by the state of valve 946:

a first activation state, in which both suction flow to one or more suction lumens 530 and cleaning fluid flow are blocked, and inflatable element 588 is deflated by active suction (via open suction channel 551 flow);

a second activation state, in which suction flow is enabled between one or more suction lumens 530 and suction port 830 via proximal suction inlet 531 into one or more suction lumens 530, inflatable element 588 is deflated by active suction (via open suction channel 551 flow), but cleaning fluid flow into one or more fluid-delivery lumens 520 remains blocked; and a third activation state, in which suction flow is enabled both between one or more suction lumens 530 and suction port 830 via proximal suction inlet 531 into one or more suction lumens 530, and cleaning fluid flow into one or more fluid-delivery lumens 520 from fluid port 827 of housing 310 via proximal fluid-delivery inlet 521, and inflatable element 588 is inflated.

Alternatively, similar to the configuration described hereinabove with reference to FIGS. 12 and 13A-B, valve 946 is implemented on suction channel 551. In such a configuration, the first activation state includes primary and secondary activation states, as described hereinabove with reference to FIGS. 12 and 13A-B.

Figure 17C:
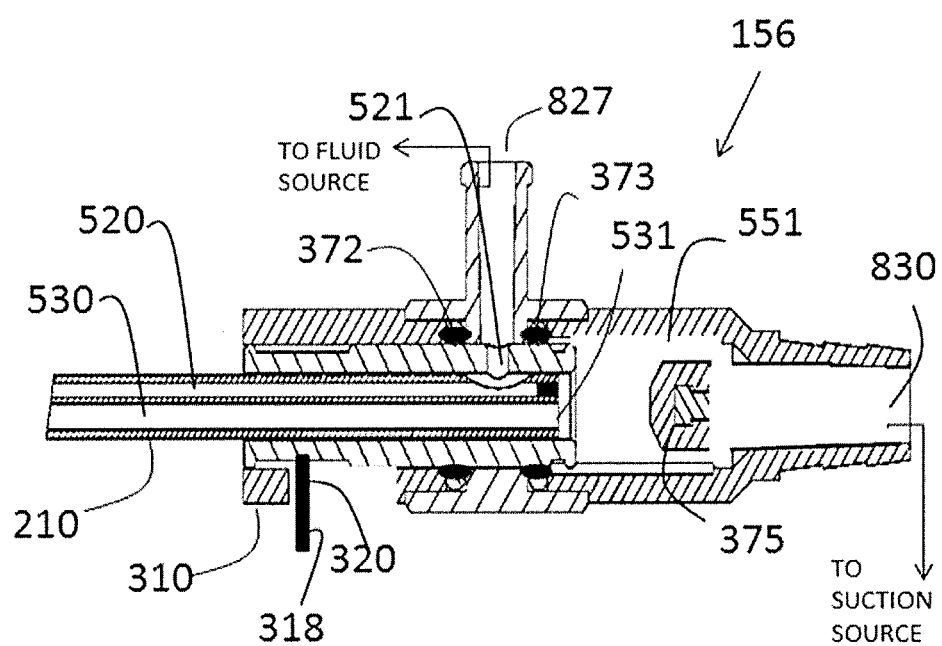

Reference is now made to FIGS. 17A-C, which are schematic illustrations of another configuration of input module 156, in accordance with an application of the present invention. In this configuration, the sealing separators are fixed with respect to housing 310 (and slidable with respect to the catheter main body). Optionally, main body 210 is shaped so as to define proximal suction inlet 531 at a proximal end of the main body. In the configuration shown in FIGS. 17A-C, one or more fluid-delivery lumens 520 are in fluid communication with inflatable element 588, such as described hereinabove with reference to FIG. 7A or with reference to FIG. 7B.

In this configuration, input module 156 comprises a sealing separator 373, such as an o-ring, which is fixed with respect to housing 310. Sealing separator 373 sealingly separates between fluid port 827 and suction port 830. Catheter main body 210 is slidable with respect to sealing separator 373. Thus, fluid communication to one or more fluid-delivery lumens 520 (and optionally also to inflation lumen 580) is switchable from suction communication to fluid delivery communication by axial motion of catheter main body 210. As a result, activation of fluid delivery to fluid-delivery orifices 525 and inflation of inflatable element 588 is activated by switching and enabling fluid communication to the same fluid-delivery-pressure source 602. The activation of the switching is done by axial motion of catheter main body 210 with respect to housing 310, to which the suction connectors and fluid delivery connectors are coupled. On the other hand, inflatable element 588 is deflated by cessation of fluid delivery to one or more fluid-delivery lumens 520 and then switching and enabling fluid communication of the inflatable element 588 to the same suction source 601 connected to suction connector 830 (e.g., via channel 551 as illustrated in FIG. 17A).

Proximal suction inlet 531 is configured to sealingly engage a suction sealer 375. The suction sealer 375 is fixed with respect to housing 310. When proximal suction inlet 531 is sealingly engaged with suction sealer 375 (as shown in FIG. 17A), fluid communication is blocked between proximal suction inlet 531 and suction port 830, thereby blocking fluid communication between suction source 601 and lumen 530 in the first activation state. When proximal suction inlet 531 is disengaged from suction sealer 375 (as shown in FIG. 17B), fluid communication is enabled between proximal suction inlet 531 and suction port 830. This engaging/disengaging is preferably actuated by axial motion of catheter main body 210 with respect to suction sealer 375.

As shown in FIG. 17A, at least one suction channel 551 facilitates fluid communication to suction port 830 around the suction sealer 375. Therefore, when proximal fluid-delivery inlet 521 is in fluid communication with suction channel 551, suction is communicated to one or more fluid-delivery lumens 520, while suction remains blocked by suction sealer 375 from communication to one or more suction lumens 530.

For example, in applications in which inflatable element 588 is in fluid communication with at least one of one or more fluid-delivery lumens 520, suction deflation of the inflatable element is effected while no suction is communicated to distal suction orifices 440 of the catheter main body.

Figure 18A:
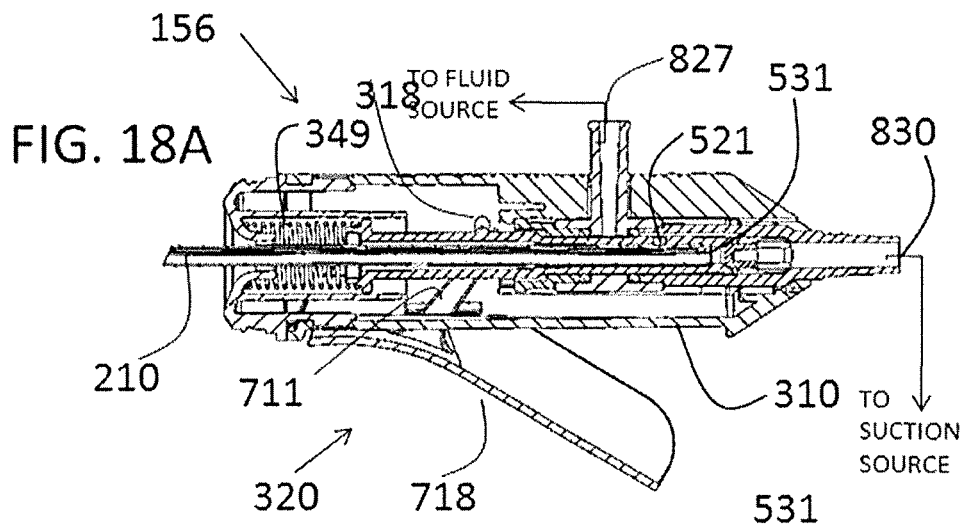
FIGS. 18A-C are schematic illustrations of yet another configuration of an input module of the cleaning system of FIGS. 1A-C, in accordance with an application of the present invention.
Figure 18B:
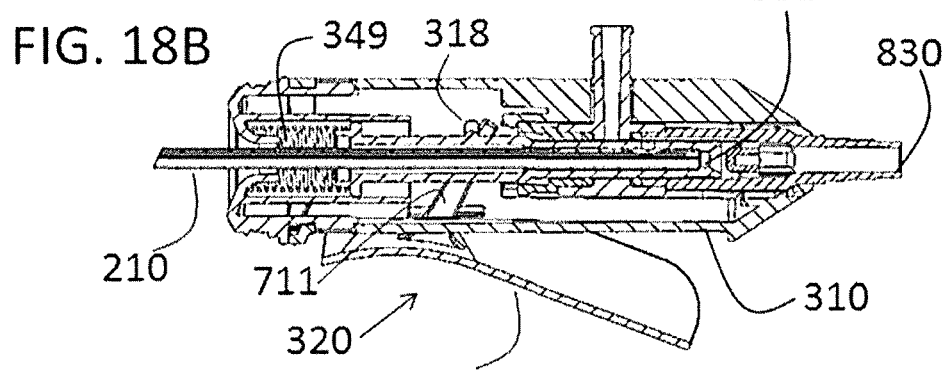
Figure 18C:
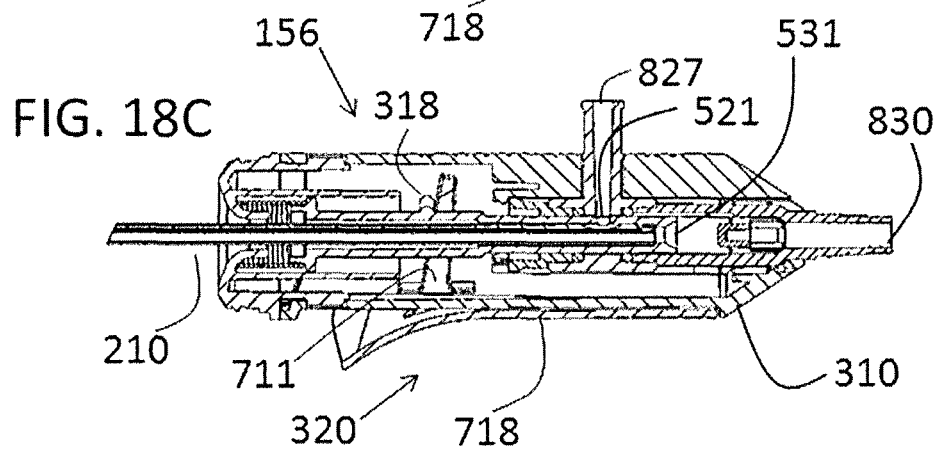

Reference is now made to FIGS. 18A-C, which are schematic illustrations of yet another configuration of input module 156, in accordance with an application of the present invention. This configuration is similar to that described hereinabove with reference to FIGS. 17A-C, except that mechanical user control element 320 comprises user control handle 718, the movement of which includes a component perpendicular to the associated axial motion of catheter main body 210, similar to the configuration of mechanical user control element 320 described hereinabove with reference to FIGS. 6A-B. Mechanical user control element 320 translates the movement of user control handle 718 into axial motion of axial motion element 318.

Reference is now made to FIGS. 19A-C, which are schematic illustrations of an input module 356, in accordance with an application of the present invention. Input module 356 is generally similar to input module 156, described hereinabove, except that input module 356 comprises a mechanical user control element 420 that comprises at least first and second buttons 321 and 322. First button 321 controls the activation of suction into one or more suction lumens 530, and second button 322 controls the activation of fluid delivery into one or more fluid-delivery lumens 520, such as using the techniques described hereinbelow with reference to FIGS. 19D-F.

For some applications, mechanical user control element 420 further comprises a button joining element 324, which is fixed to first button 321, and arranged to allow depression of first button 321 only to a certain extent independently of depression of second button 322. Button joining element 324 allows the depression of first button 321 and/or button joining element 324 from the state of depression of first button 321 shown in FIG. 19A to the greater state of depression of first button 321 shown in FIG. 19B, without also depressing second button 322. However, further depression of first button 321 and/or button joining element 324 causes the simultaneous depression of second button 322, as shown in FIG. 19C.

Typically, the activation states of the configuration described with reference to FIGS. 19A-C correspond with those described hereinabove with reference to FIGS. 18A-C.

FIGS. 19D-F are schematic illustrations of the operation of buttons 321 and 322, in accordance with an application of the present invention. In particular, it is noted that the operation of switching between activation states in this configuration does not involve motion of catheter main body 210 (e.g., no motion relative to suction inlet 830). The states shown in FIGS. 19D, 19E, and 19F correspond to the states shown in FIGS. 19A, 19B, and 19C, respectively.

As illustrated in FIG. 19D, suction lumen 530 is intermitted by a gate area 327 traversed by suction control button 321, and fluid-delivery lumen 520 is intermitted by a gate area 328 traversed by suction control button 322. Thus, in this configuration, the fluid communication is blocked in lumen 530 across gate 327 and blocked in fluid-delivery lumen 520 across gate 328.

FIG. 19D, when understood to show a sub-detail of FIG. 19A, illustrates the main principle of the button press mechanism in which fluid communication between suction port 830 and the distal end of the main body 210 is interrupted by button gate 321. By way of non-limiting example, FIG. 19D illustrates such interruption as taking place on a portion of lumen 530 in main body 210 itself. The scope of the present invention includes other configuration. For example, the same principles of this mechanism can be realized by the button interrupting the fluid communication between suction port 830 and inlet 531 to lumen 530. Similarly, the same principles of this mechanism of button action is applicable to button 322 interrupting the fluid communication between fluid port 827 and proximal fluid-delivery inlet 521 to the fluid-delivery lumen 520.

As illustrated in FIG. 19E, the control button 321 has a hole passage 325. When the button 321 is partially depressed to the level that hole passage 325 overlaps with the lumen 530 cross-section, fluid communication is enabled in suction lumen 530 across the gate 327. Yet, at this button 321 depression level, there is no change in button 322 depression level, and therefore fluid communication remains blocked in fluid-delivery lumen 520 across the gate 328 in this second activation state.

As illustrated in FIG. 19F, the control button 322 has a hole passage 326. When button 321 is further depressed such that also the button 322 is depressed to the level that hole passage 326 overlaps with the fluid-delivery lumen 520 cross-section, fluid communication is enabled in fluid-delivery lumen 520 across gate 328. Therefore, fluid communication is enabled across both fluid-delivery lumen 520 and suction lumen 530 in this button control configuration for the third activation state.

Figure 20:
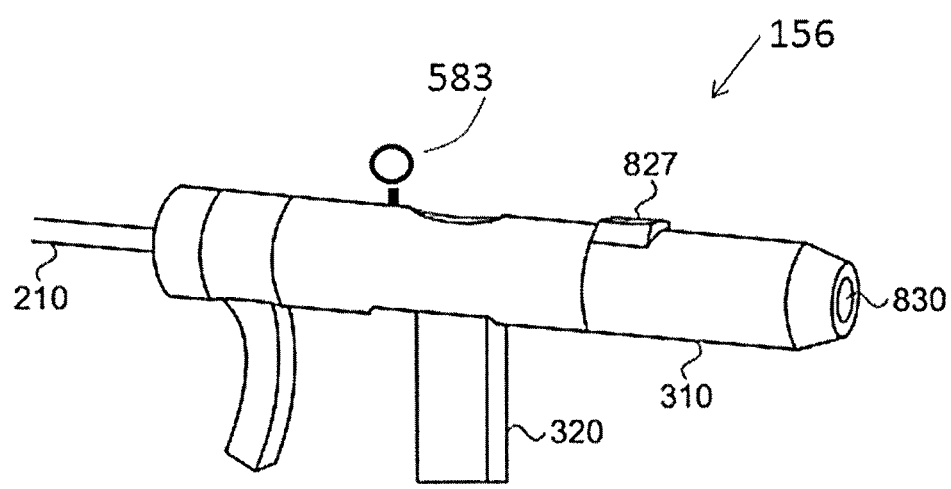
FIG. 20 is a schematic illustration of an input module of the cleaning system of FIGS. 1A-C, in accordance with an application of the present invention.

Reference is now made to FIG. 20, which is a schematic illustration of input module 156, in accordance with an application of the present invention. This configuration may be implemented in conjunction with any of the configurations of input module 156 described herein in which expandable element 588 is inflatable. In this configuration, input module 156 comprises an external inflation indicator 583, which indicates inflation/deflation state of expandable element 588. For some applications, inflation indicator 583 comprises pilot balloon. Pilot balloon 583 is in fluid communication with the lumen in fluid communication with inflatable element 588, such that the inflation pressures of the pilot balloon and the inflatable element are correlated (though likely not identical due to a pressure drop in the lumen in fluid communication with inflatable element 588).

Figure 21A:
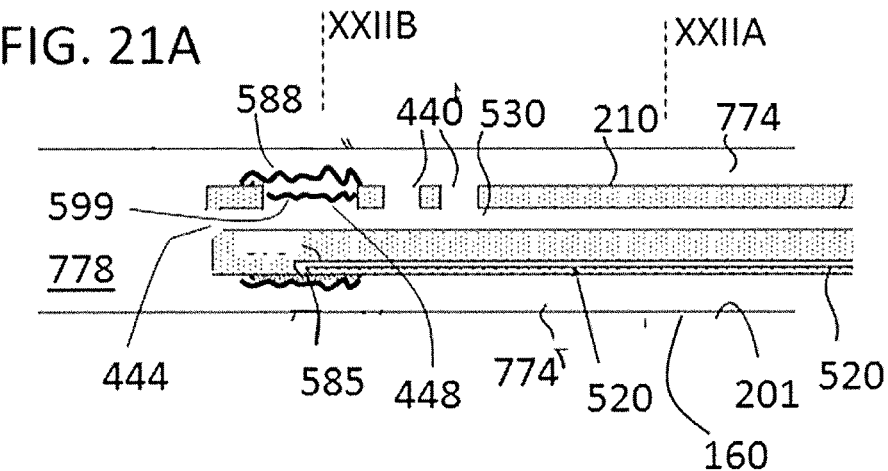
FIGS. 21A-B and 22A-C are schematic illustrations of a distal portion of a main body of the cleaning system of FIGS. 1A-C inserted into a ventilation tube, in accordance with an application of the present invention.
Figure 21B:
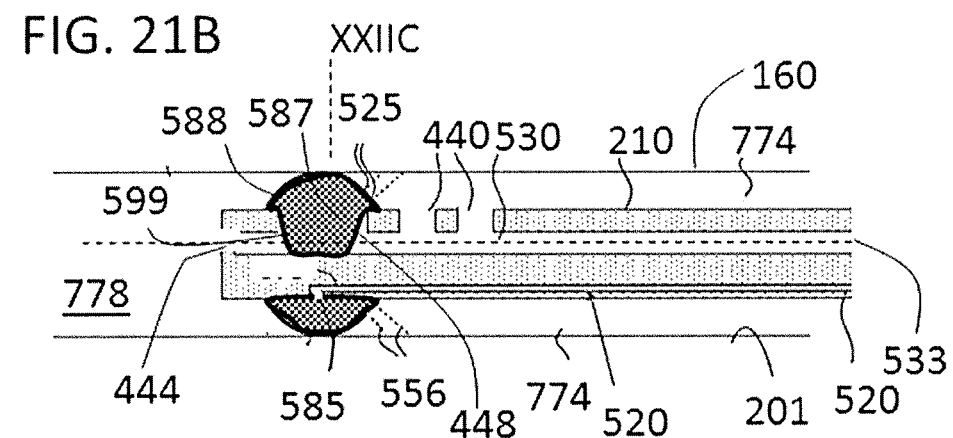
Figures 22A, 22B, 22C:
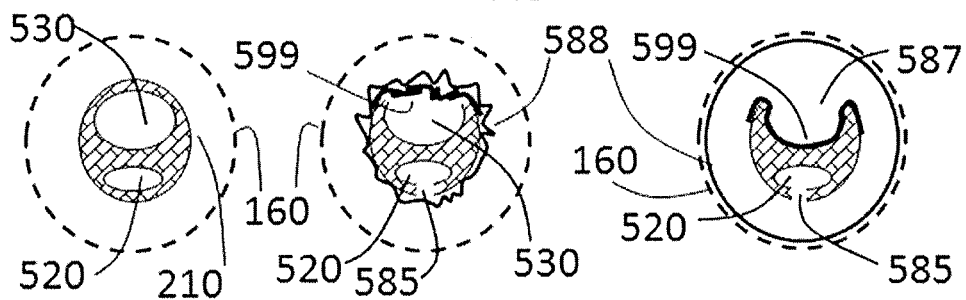

Reference is now made to FIGS. 21A-B and 22A-C, which are schematic illustrations of distal portion 212 of cleaning catheter 200 inserted into ventilation tube 160, in accordance with an application of the present invention. FIGS. 21A and 21B are side view of expandable element 588 in uninflated and inflated states, respectively. FIGS. 22A, 22B, and 22C are cross-sectional views of distal portion 212 of cleaning catheter 200 taken along lines at an axial location proximal to the proximal-most suction orifices 440 in FIG. 21A, at inflatable element 588 in FIG. 21A, and at inflatable element 588 in 21B, respectively. In this configuration, expandable element 588 comprises an inflatable element, such as a balloon. The configuration described with reference to FIGS. 21A-B and 22A-C may be used in combination with any of the other configurations of cleaning system 100 described hereinabove, mutatis mutandis. For some applications, one or more suction lumens 530 comprise exactly one suction lumen 530, while for other applications, one or more suction lumens 530 comprise a plurality of suction lumens 530.

In this configuration, one or more distal suction orifices 440 comprise one or more lateral suction orifices 440 located along distal portion 212 at one or more respective locations proximal to inflatable element 588. In addition to lateral suction orifices 440, catheter main body 210 is shaped so as to define a distal-most suction orifice 444 at a distal end of distal portion 212 of cleaning catheter 200, distal to inflatable element 588. Distal-most suction orifice 444 is in fluid communication with a distal portion of suction lumen 530. For some applications, distal-most suction orifice 444 is defined by a distal tip of the cleaning catheter (as shown), while for other applications distal-most suction orifice 444 is defined by a lateral wall of the cleaning catheter distal to inflatable element 588 (configuration not shown). Distal-most suction orifice 444 enables cleaning system 100 to selectively apply suction to the trachea. The techniques of FIGS. 21A-B and 22A-C allow cleaning system 100 to modulate suction provided from distal-most suction orifice 444 distal to inflatable element 588, relative to the suction provided to the distal suction orifices 440. The techniques include modulating occlusion of suction lumen 530, at an axial location 446 at which location 446 inflatable element 588 is positioned. Axial location 446 is proximal to distal-most suction orifice 444, and longitudinally between distal-most suction port orifice and one or more distal suction orifices 440 (in typically configurations in which distal suction orifices 440 are provided).

For some applications, this occlusion of suction lumen 530 at axial location 446 is achieved using a collapsible membrane 599 at least partially positioned along an opening 448 extending through the outer wall of main body 210 into suction lumen 530, at axial location 446. Inflatable element 558 is mounted to main body 210 at least partially along opening 448. The collapsible membrane is positioned within an interior of inflatable element 588, such that an inflatable chamber 587 is defined between the wall of inflatable element 588 and collapsible membrane 599. The collapsible membrane typically forms a fluid-tight seal with the wall of suction lumen 530 around opening 448.

When inflatable element 588 is inflated via inflation port 825, as shown in FIGS. 21B and 22C, the inflation also causes inflation and expansion of inflatable chamber 587 and of collapsible membrane 599 into suction lumen 530, so as to at least partially occlude the passage between distal-most suction orifice 444 (distal to inflatable element 588) and distal suction orifices 440 (proximal to the inflatable element), thereby modulating a level of suction delivered to distal-most suction orifice 444 via suction lumen 530. For good occlusion, collapsible membrane 599 typically penetrates deep enough into suction lumen 530 across a central longitudinal axis 533 of suction lumen 530. The occlusion is reversible, as illustrated in FIGS. 21A and 22B. Upon deflation of inflatable element 588, the deflation collapses membrane 599 towards the wall of inflatable element 588, out of the suction lumen, preferably so that collapsed membrane 599 is in a collapsed configuration which does not cross axis 533 of suction lumen 530. Typically, membrane 599 comprises a material that is thinner than a material of the wall of inflatable element 588, such as less than 70%, e.g., less than 50%, such as less than 30%, of a thickness of the material of the wall of inflatable element 588. For some applications, the membrane and the inflatable element comprise an elastic material such as polyurethane, silicone, or PCV. The membrane and the inflatable element may comprise the same material or different materials.

For some applications, cleaning catheter 100, configured as described with reference to FIGS. 21A-B and 22A-C is used to modulate relative levels of suction delivered by suction lumen 530 to (a) the distal-most suction orifice 444 and (b) the one or more lateral suction orifices 440 between at least two levels that include:

a relatively low distal-most level, in which a level of suction delivered to the distal-most suction orifice 444 is less than 25% of a level of suction delivered to one of the one or more lateral suction orifices 440 having a greatest cross-sectional area, and a relatively high distal-most level, in which the level of suction delivered to the distal-most suction orifice 444 is greater than 25% of the level of suction delivered to the one of the one or more lateral suction orifices 440 having the greatest cross-sectional area.

For some applications, in the relatively low distal-most level, the level of suction delivered to the distal-most suction orifice 444 is less than 10% of the level of suction delivered to the one of the one or more lateral suction orifices 440 having the greatest cross-sectional area, and, in the relatively high distal-most level, the level of suction delivered to the distal-most suction orifice 444 is greater than 10% of the level of suction delivered to the one of the one or more lateral suction orifices 440 having the greatest cross-sectional area. For some applications, in the relatively low distal-most level, substantially no suction is delivered to the distal-most suction orifice 444.

For some applications, inflatable element 588 and inflatable chamber 587 are inflated via one or more fluid-delivery lumens 520, as shown in FIGS. 21A-B. For other applications, inflatable element 588 and inflatable chamber 587 are inflated via inflation lumen 580, described hereinbelow with reference to FIG. 2 (configuration not shown).

For some applications, an alternative configuration is provided in which membrane 599 and inflatable element 588 are positioned at different axial locations along main body 210. In this configuration, membrane 599 defines inflatable chamber 587 with an inner surface of one of the one or more fluid-delivery lumens 520, rather than with inflatable element 588. Typically, inflatable chamber 587 and inflatable element 588 are inflated via the same lumen. Alternatively, they are inflated via different lumens, which may or may not be in fluid communication either along main body 210 and/or in a flow regulator 700.

For some applications, a method, which optionally uses the configuration of cleaning catheter 200 described hereinabove with reference to FIGS. 21A-B and 22A-C comprises:

providing cleaning catheter 200, which includes (a) main body 210, which is shaped so as to define distal-most suction orifice 444 and one or more lateral suction orifices 440, and (b) inflatable element 588, which is mounted to main body 210 axially between (i) distal-most suction orifice 444 and (ii) one or more lateral suction orifices 440; and modulating relative levels of suction delivered by suction source 601 to (a) distal-most suction orifice 444 and (b) one or more lateral suction orifices 440.

For some applications, modulating comprises modulating the relative levels of suction between at least two levels that include:

a relatively low distal-most level, in which a level of suction delivered to the distal-most suction orifice 444 is less than 25% of a level of suction delivered to one of the one or more lateral suction orifices 440 having a greatest cross-sectional area, and a relatively high distal-most level, in which the level of suction delivered to the distal-most suction orifice 444 is greater than 25% of the level of suction delivered to the one of the one or more lateral suction orifices 440 having the greatest cross-sectional area.

For some applications, modulating comprises modulating the relative levels of suction between the at least two levels that include:

the relatively low distal-most level, in which the level of suction delivered to the distal-most suction orifice 444 is less than 10% of the level of suction delivered to the one of the one or more lateral suction orifices 440 having a greatest cross-sectional area, and the relatively high distal-most level, in which the level of suction delivered to the distal-most suction orifice 444 is greater than 10% of the level of suction delivered to the one of the one or more lateral suction orifices 440 having the greatest cross-sectional area.

For some applications, modulating the relative levels of suction comprises reversibly modulating a level of occlusion of at least one of the one or more suction lumens 530 at a portion thereof axially between (x) the distal-most suction orifice 444 and (y) the one or more lateral suction orifices 440.

For some applications, cleaning catheter 200 further includes suction lumen 530 arranged along main body 210, in fluid communication with distal-most suction orifice 444 and lateral suction orifices 440, and modulating the relative levels of suction comprises reversibly modulating a level of occlusion of suction lumen 530 at a portion thereof axially between (a) distal-most suction orifice 444 and (b) one or more lateral suction orifices 440.

For some applications, providing cleaning catheter 200 comprises providing cleaning catheter 200 further including exactly one suction lumen 530 arranged along main body 210, in fluid communication with distal-most suction orifice 444 and lateral suction orifices 440.

For some applications, providing cleaning catheter 200 comprises providing cleaning catheter 200 further including a plurality of suction lumens 530 arranged along main body 210, in fluid communication with one another and with distal-most suction orifice 444 and lateral suction orifices 440.

For some applications, further comprising, before modulating the relative levels of suction, inserting distal portion 212 of cleaning catheter 200 into ventilation tube 160 inserted in a trachea of a patient.

Reference is now made to FIG. 23, which is a schematic illustration of a portion of proximal portion 214 of main body 210, in accordance with an application of the present invention. FIG. 8 shows one or more fluid-delivery lumens 520 and one or more suction lumens 530, which have been omitted from FIGS. 24A-C for clarity of illustration. FIG. 23 (and FIGS. 24A-C) illustrate configurations of proximal portion 214 of main body 210 appropriate for use with either of the configurations of distal portion 212 of cleaning catheter 200 described hereinabove with reference to FIGS. 7A and 7B. In these configuration, expandable element 588 is inflated via fluid communication to pressurized fluid in at least one of one or more fluid-delivery lumens 520, e.g., exactly one fluid-delivery lumen 520, which are in fluid communication with an interior of expandable element 588. There is thus no need to provide separate inflation lumen 580 to the expandable element (such as described hereinabove with reference to FIGS. 3 and 4A-C), because the expandable element is inflated via one or more inflation outlets 585 from the at least one of the one or more fluid-delivery lumens 520 itself. Alternatively, expandable element 588 is inflated via dedicated inflation lumen 580 which is in fluid communication directly with one or more fluid-delivery lumens 520, or with the same source 602 of pressurized fluid with which one or more fluid-delivery lumens 520 are in fluid communication (configuration not shown).

In the particular configuration shown in FIG. 23 (and FIGS. 24A-C), main body 210 is shaped so as to define at least two lumens: one or more fluid-delivery lumens 520 (e.g., exactly one fluid-delivery lumen 520), and one or more suction lumens 530 (e.g., exactly one suction lumen 530), and respective at least one proximal fluid-delivery inlet 521 (e.g., exactly one proximal fluid-delivery inlet 521), and at least one proximal suction inlet 531 (e.g., exactly one proximal suction inlet 531). In this particular configuration, main body 210 is not shaped so as to define inflation lumen 580 or inflation inlet 581, described hereinabove with reference to FIGS. 3 and 4A-C. In this particular configuration, expandable element 588 comprises an inflatable element 588, such as a balloon.

FIG. 23 shows one or more fluid-delivery lumens 520 and one or more suction lumens 530, which have been omitted from FIGS. 24A-B for clarity of illustration. For some applications, proximal suction inlet 531 is located distal to proximal fluid-delivery inlet 521. This axial arrangement of inlets 521 and 531 is the reverse of the configurations described hereinabove in the other configurations, which affects the order of fluid delivery states, as described below. The techniques of this configuration may be implemented using any of the configurations described hereinabove for inflating and deflating inflatable element 588, mutatis mutandis. For some applications, as shown, proximal fluid-delivery inlet 521 is defined by a lateral wall of main body 210, while for other applications, proximal fluid-delivery inlet 521 is defined by a proximal end of main body 210, such as shown in FIGS. 5B-C, 17A-C, and 18A-C for proximal suction inlet 531.

Reference is made to FIGS. 24A-C, which are schematic illustrations of several states of a flow regulator 1000 of input module 156, in accordance with an application of the present invention. Except as described as follows, input module 156 is configured as described hereinabove with reference to FIGS. 9A-C. Except as described as follows, flow regulator 1000 is generally similar to flow regulator 710, described hereinabove with reference to FIGS. 9A-C. As mentioned above, in some applications input portion 216 of proximal portion of main body 210 is configured to be inserted into and axially slidable with respect to input module 156. Input module 156 has a plurality of ports for connection with various fluid sources, including at least suction source 601 and pressurized fluid source 602. In this configuration, input module 156 includes fluid port 827, which is coupleable in fluid communication with pressurized fluid source 602, and suction port 830, which is coupleable in fluid communication with suction source 601, but does not include inflation port 832, described hereinabove with reference to FIGS. 4A-C. In this configuration, the locations fluid port 827 and suction port 830 along housing 310 are reversed with respect to the locations in the other configurations described herein. In addition, inflation source 603 is not provided.

As mentioned above, input module 156 is configured to assume a plurality of activation states. Mechanical control unit 320 is typically configured to mechanically and non-electrically set the states of flow regulator 1000. Input module 156 is configured to set the activation states enabling or blocking fluid communication between the various lumen inlets and the external fluid sources via respective ports. For some applications, transitions between states are effected by shifts in alignment of the lumen inlets with respect to various chambers of input module 156, which chambers are or are not in fluid communication with respective ports. The shifts in alignment are typically effected via axial motion of input portion 216 of catheter main body 210 within input module housing 310, along the longitudinal axes of input portion 216 and input module 156.

In this configuration, flow regulator 1000 is configured to have three principal activation states, typically associated with three configurations (e.g., spatial positions) of mechanical user control element 320. In the configuration illustrated in FIGS. 24A-C, the three states are actuated by axial motion of proximal portion 214 of elongated main body 210 relative to input module housing 310:

as shown in FIG. 24A, a first activation state, in which flow regulator 1000 blocks fluid communication (a) between suction port 830 and proximal suction inlet 531, and thus one or more suction lumens 530 and (b) between fluid port 827 and proximal fluid-delivery inlet 521, and thus one or more fluid-delivery lumens 520; as a result, fluid communication is blocked to both fluid-delivery orifices 525 and the interior of inflatable element 588 (this configuration can be used with either the configuration described with reference to FIG. 7A or that described with reference to FIG. 7B). For some applications, this first activation state may be considered to be a base, default activation state, which optionally is set by an elastic return force element, such as described hereinbelow with reference to FIGS. 5B-C;

as shown in FIG. 24B, a second activation state, in which flow regulator 1000 effects fluid communication between fluid port 827 and one or more fluid-delivery lumens 520 via proximal fluid-delivery inlet 521, and blocks the fluid communication between suction port 830 and one or more suction lumens 530; and as shown in FIG. 24C, a third activation state, in which flow regulator 1000 effects both (a) suction fluid communication between suction port 830 and one or more suction lumens 530 via proximal suction inlet 531, and (b) fluid communication between fluid port 827 and one or more fluid-delivery lumens 520 via proximal fluid-delivery inlet 521; as a result, fluid communication is provided to both fluid-delivery orifices 525 and the interior of inflatable element 588.

As mentioned above, mechanical user control element 320 is configured to mechanically and non-electrically set the states of flow regulator 1000. Typically, mechanical user control element 320 has at least first, second and third configurations (e.g., spatial positions), and, typically, is configured to transition between the first and the third configuration (e.g., spatial positions) via the second configuration (e.g., spatial position). For example, mechanical user control element 320 is shown in FIG. 24A in its first configuration (e.g., spatial position) (right-most position), in FIG. 24B in its second configuration (e.g., spatial position) (center position), and in FIG. 24C in its third configuration (e.g., spatial position) (left-most position). Input module 156 is configured such that:

when user control element 320 is in the first configuration (e.g., spatial position), flow regulator 1000 is in the first activation state, as described above;

when user control element 320 is in the second configuration (e.g., spatial position), flow regulator 1000 is in the second activation state, as described above; and when user control element 320 is in the third configuration (e.g., spatial position), flow regulator 1000 is in the third activation state, as described above.

As mentioned, FIG. 24A shows flow regulator 1000 in the first (blocked) state. Input portion 216 of main body 210 is encased, yet movable, within housing 310 of input module 156. Catheter main body 210 is slidable through a distal wall 314 of housing 310. Housing 310 is shaped so as to define suction port 830 and cleaning fluid port 827 (main body 210 does not define these ports).

As main body 210 moves within the inner compartment of housing 310, transverse sealing separators 341, 342, 343, and 344 delineate distinct chambers within the housing. When flow regulator 1000 is in the first activation state, as shown in FIG. 24A, separators 342 and 343 and the outer surface of elongated main body 210 delineate first chamber 350 around proximal suction inlet 531, and thereby block direct fluid communication within housing 310 between proximal fluid-delivery inlet 521 and proximal suction inlet 531. The separators are attached to the main body and snugly pressed against the inner surface of housing 310, so that the insulated chamber around proximal suction inlet 531 is maintained even as the main body slides a certain distance along the longitudinal axis thereof with respect to the housing.

Also as shown in FIG. 24A, in the first activation state, elongated main body 210 is positioned in its closest position to a proximal end 360 of housing 310, proximal-most separator 344 creates a seal which prevents direct fluid communication between fluid port 827 of housing 310 and proximal fluid-delivery inlet 521 of elongated main body 210. In this base position, suction fluid flow is blocked within a second sealed chamber 352 delineated by separators 341 and 342 and the outer surface of elongated main body 210.

When flow regulator 1000 is in the second activation state, as shown in FIG. 24B, fluid communication is established between fluid port 827 of housing 310 and proximal fluid-delivery inlet 521 and into one or more fluid-delivery lumens 520 in elongated main body 210, yet suction remains blocked within second sealed chamber 352 delineated by separators 341 and 342 and the outer surface of elongated main body 210. This activation is achieved by sliding elongated main body 210 distally along the axial direction by a limited distance such that separator 342 does not yet cross into the space of cleaning suction port 830. Typically, this sliding motion is induced by distally pushing on mechanical user control element 320, which is coupled to elongated main body 210 and passes through a slit 312 in housing 310 which allows axial motion of mechanical user control element 320.

When flow regulator 1000 is in the third activation state, as shown in FIG. 24C, fluid communication is established in first chamber 350 between suction port 830 of housing 310 and proximal suction inlet 531 and one or more suction lumens 530 in elongated main body 210. Cleaning fluid port 827 of housing 310 remains in fluid communication with proximal fluid-delivery inlet 521 and into one or more fluid-delivery lumens 520 in elongated main body 210. Therefore, in this third activation state, flow regulator 1000 effects both (a) cleaning fluid flow into one or more fluid-delivery lumens 520 and (b) suction in one or more suction lumens 530 of elongated main body 210. This activation is achieved by sliding elongated main body 210 more distally along the axial direction by a limited distance such that separator 342 crosses into or passes across the space of suction port 830. Typically, the sliding motion is induced by distally pushing on mechanical user control element 320, which is coupled to elongated main body 210 and passes through slit 312 in housing 310.

Thus, three activation states can be actuated, typically associated with three configurations (e.g., spatial positions) of mechanical user control element 320. In the configuration illustrated in FIGS. 24A-C, the three states are actuated by axial motion of input portion 216 of elongated main body 210 relative to input module housing 310:

the first activation state, in which suction flow and cleaning fluid flow is blocked;

the second activation state, in fluid communication is enabled between fluid port 827 and one or more fluid-delivery lumens 520 via proximal fluid-delivery inlet 521, but suction flow to one or more suction lumens 530 is remains blocked; and the third activation state, in which suction flow is enabled both between one or more suction lumens 530 and suction port 830 via proximal suction inlet 531 into one or more suction lumens 530, and cleaning fluid flow into one or more fluid-delivery lumens 520 from fluid port 827 of housing 310 via proximal fluid-delivery inlet 521, thereby both providing fluid to fluid-delivery orifices 525 and the interior of inflatable element 588, so as to inflate the inflatable element.

For some applications, expandable element 588 is emptied by suction via the same suction source 601 which is connected to suction port 830. This can be enabled, for example, by establishing fluid communication between the lumen which is in fluid communication with expandable element (at least one of one or more fluid-delivery lumens 520 or inflation lumen 580). For some applications, expandable element 588 can be both inflated via pressurized delivery fluid in communication with one or more fluid-delivery lumens 520 and be deflated by suction provided by the same source 601 connected to one or more suction lumens 530. Examples of such configurations are described hereinabove with reference to FIGS. 10 and 11A-C, FIGS. 12A-B and 13A-B, FIGS. 14 and 15A-B, and FIGS. 16A-C.

Although the activation states of input module 156 are sometimes characterized hereinabove as "first," "second," or "third," these ordinal numbers do not necessarily imply a particular order of activation during use of cleaning system 100 unless explicitly stated. In addition, input module 156 may have activation states in addition to those described herein, which may be activated before, after, or temporarily between the states described herein, including before any states characterized as "base" states herein. The ordinal numbers of the states recited in claims do not necessarily correspond to the ordinal numbers of the states described hereinabove in the specification.

The specifications of cleaning fluids/inflatable element inflation/suction fluids and lumens should not be taken as limiting. It is self-evident that other fluids can be delivered in catheter lumens for various purposes.

In the description and claims of the present application, each of the verbs, "comprise," "include" and "have," and conjugates thereof, are used to indicate that the object or objects of the verb are not necessarily a complete listing of members, components, elements or parts of the subject or subjects of the verb. The articles "a" and "an" are used herein to refer to one or to more than one (i.e., to at least one) of the grammatical object of the article. By way of example, "an element" means one element or more than one element. The term "including" is used herein to mean, and is used interchangeably with, the phrase "including but not limited to." The term "or" is used herein to mean, and is used interchangeably with, the term "and/or," unless context clearly indicates otherwise. The term "such as" is used herein to mean, and is used interchangeably, with the phrase "such as but not limited to."

All publications, patent applications, patents, and other references mentioned herein are incorporated by reference in their entirety. In case of conflict, the present patent specification, including definitions, will prevail. In addition, the materials, methods, and examples are illustrative only and not intended to be limiting.

For brevity, some explicit combinations of various features are not explicitly illustrated in the figures and/or described. It is now disclosed that any combination of the method or device features disclosed herein can be combined in any manner—including any combination of features—any combination of features can be included in any embodiment and/or omitted from any embodiments.

The scope of the present invention includes embodiments described in the following applications, which are assigned to the assignee of the present application and are incorporated herein by reference. In an embodiment, techniques and apparatus described in one or more of the following applications are combined with techniques and apparatus described herein. It is noted that the phrase "activation state" used herein may, for some applications, correspond in some respects to the phrases "mode," "activation mode," and/or "operating mode" referred to in the following applications (although many of the configurations of these states described herein differ in at least some respects from the configurations of the modes described in the following applications). It is also noted that the phrase "mechanical user control element" used herein may, for some applications, correspond in some respects to the word "switch," referred to in the following applications (although many of the configurations of these states described herein differ in at least some respects from the configurations of the modes described in the following applications):

International Application PCT/IB2012/051532, filed Mar. 29, 2012, which published as PCT Publication WO 2012/131626;

UK Application GB 1116735.0, filed Sep. 28, 2011, which published as GB 2482618 A to Einav et al.;

UK Application GB 1119794.4, filed Nov. 16, 2011;

U.S. Provisional Application 61/468,990, filed Mar. 29, 2011;

U.S. Provisional Application 61/473,790, filed Apr. 10, 2011;

U.S. Provisional Application 61/483,699, filed May 8, 2011;

U.S. Provisional Application 61/496,019, filed Jun. 12, 2011;

U.S. Provisional Application 61/527,658, filed Aug. 26, 2011;

U.S. Provisional Application 61/539,998, filed Sep. 28, 2011;

U.S. Provisional Application 61/560,385, filed Nov. 16, 2011;

U.S. Provisional Application 61/603,340, filed Feb. 26, 2012;

U.S. Provisional Application 61/603,344, filed Feb. 26, 2012;

U.S. Provisional Application 61/609,763, filed Mar. 12, 2012;

U.S. Provisional Application 61/613,408, filed Mar. 20, 2012;

U.S. Provisional Application 61/635,360, filed Apr. 19, 2012;

U.S. Provisional Application 61/655,801, filed Jun. 5, 2012;

U.S. Provisional Application 61/660,832, filed Jun. 18, 2012; and

U.S. Provisional Application 61/673,744, filed Jul. 20, 2012.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with a tracheal ventilation tube and a suction source, the method comprising:

coupling, in fluid communication with the suction source, a suction port of a flow regulator of an input module;

inserting a cleaning catheter into the ventilation tube inserted in a trachea of a patient, which cleaning catheter (a) is coupled to the input module, (b) is shaped so as to define one or more distal suction orifices, and (c) includes (i) an elongate, flexible, tubular main body, (ii) one or more fluid-delivery lumens arranged along the main body, (iii) one or more suction lumens arranged along the main body, and (iv) an inflatable element, which is mounted to the main body at a location within 3 cm of at least one of the one or more distal suction orifices;

activating the flow regulator to assume a first activation state, in which the flow regulator effects fluid communication between the suction source and an interior of the inflatable element via at least one of the one or more fluid-delivery lumens, thereby deflating the inflatable element; and activating the flow regulator to assume a second activation state, in which the flow regulator effects fluid communication between the suction source and the distal suction orifices via the one or more suction lumens, and does not effect the fluid communication between the suction source and the interior of the inflatable element.

* * * * *